(12) United States Patent
Steinke et al.

(10) Patent No.: US 12,383,745 B2
(45) Date of Patent: Aug. 12, 2025

(54) MANAGEMENT OF COMPLIANCE VOLTAGE FOR A STIMULATOR DEVICE

(71) Applicant: Boston Scientific Neuromodulation Corporation, Valencia, CA (US)

(72) Inventors: G. Karl Steinke, Valencia, CA (US); Adam T. Featherstone, Meridian, ID (US); Mary Kotchevar, Minneapolis, MN (US); Emanuel Feldman, Simi Valley, CA (US); Goran N. Marnfeldt, Valencia, CA (US); Kenneth Hermann, Santa Clara, CA (US); Chirag Shah, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 600 days.

(21) Appl. No.: 17/753,135

(22) PCT Filed: Sep. 2, 2020

(86) PCT No.: PCT/US2020/049054
§ 371 (c)(1),
(2) Date: Feb. 21, 2022

(87) PCT Pub. No.: WO2021/046120
PCT Pub. Date: Mar. 11, 2021

(65) Prior Publication Data
US 2022/0273953 A1    Sep. 1, 2022

Related U.S. Application Data

(60) Provisional application No. 62/897,060, filed on Sep. 6, 2019.

(51) Int. Cl.
*A61N 1/36* (2006.01)
*A61N 1/372* (2006.01)

(52) U.S. Cl.
CPC ..... *A61N 1/36153* (2013.01); *A61N 1/36125* (2013.01); *A61N 1/37247* (2013.01)

(58) Field of Classification Search
CPC ............ A61N 1/36153; A61N 1/36125; A61N 1/37247; A61N 1/36; A61N 1/37; A61N 1/3925
See application file for complete search history.

(56) References Cited

U.S. PATENT DOCUMENTS 3,646,940 A   3/1972   Timm et al.
3,724,467 A   4/1973   Avery et al.
(Continued)

FOREIGN PATENT DOCUMENTS

EP        1686692        8/2006
WO    1999/052163      10/1999
(Continued)

OTHER PUBLICATIONS

Ki, Wing-Hung, et al., "Analysis and Design Strategy of On-Chip Charge Pumps for Micro-Power Energy Harvesting Applications," IFIP/IEEE International Conference on Very Large Scale Integration—System on a Chip, vol. 379, pp. 158-186 (2011).
(Continued)

*Primary Examiner* — Ankit D Tejani
*Assistant Examiner* — Joshua Brendon Solomon
(74) *Attorney, Agent, or Firm* — Lewis & Reese, PLLC

(57) ABSTRACT

A compliance voltage management algorithm is disclosed for managing the compliance voltage, VH, that powers the DAC circuitry in a stimulator device. A user can use a user interface associated with an external programming device to define a time-varying stimulation waveform to be programmed into the stimulator device. The algorithm analyzes the prescribed waveform and determines a number of groups of pulses that will be treated similarly from a VH manage- (Continued)

ment standpoint. Optimal compliance voltages are determined for each group, as are the rise and fall rates at which VH is able to change at transitions between groups. These rise or fall rates in VH are then used to set when the compliance voltage should increase or decrease. For example, the algorithm will automatically set VH to start rising in advance of a transition so that it is at the proper higher value when the transition occurs.

20 Claims, 55 Drawing Sheets

(56) References Cited

U.S. PATENT DOCUMENTS

| | | |
|---|---|---|
| 3,733,498 A | 5/1973 | Watson |
| 3,822,708 A | 7/1974 | Zilber |
| 4,050,004 A | 9/1977 | Greatbatch |
| 4,134,408 A | 1/1979 | Brownlee et al. |
| 4,197,850 A | 4/1980 | Schulman |
| 4,231,027 A | 10/1980 | Mann |
| 4,232,679 A | 11/1980 | Schulman |
| 4,324,251 A | 4/1982 | Mann |
| 4,532,930 A | 8/1985 | Crosby |
| 4,793,353 A | 12/1988 | Borkan |
| 5,193,539 A | 3/1993 | Schulman et al. |
| 5,193,540 A | 3/1993 | Schulman et al. |
| 5,312,439 A | 5/1994 | Loeb |
| 5,405,367 A | 4/1995 | Schulman et al. |
| 5,433,737 A | 7/1995 | Aimone |
| 5,643,330 A | 7/1997 | Holsheimer |
| 5,723,969 A | 3/1998 | Archer et al. |
| 5,733,313 A | 3/1998 | Barreras et al. |
| 5,757,167 A | 5/1998 | Arora et al. |
| 5,814,089 A | 9/1998 | Stokes et al. |
| 5,818,703 A | 10/1998 | Jacobson |
| 5,836,981 A | 11/1998 | Chang et al. |
| 5,847,551 A | 12/1998 | Arora et al. |
| 5,959,371 A | 9/1999 | Dooley |
| 6,035,235 A | 3/2000 | Perttu et al. |
| 6,035,237 A | 3/2000 | Schulman et al. |
| 6,051,017 A | 4/2000 | Loeb et al. |
| 6,061,596 A | 5/2000 | Richmond et al. |
| 6,076,018 A | 6/2000 | Sturman |
| 6,164,284 A | 12/2000 | Schulman et al. |
| 6,175,764 B1 | 1/2001 | Loeb et al. |
| 6,181,965 B1 | 1/2001 | Loeb et al. |
| 6,181,969 B1 | 1/2001 | Gord |
| 6,185,452 B1 | 2/2001 | Schulman |
| 6,185,455 B1 | 2/2001 | Loeb et al. |
| 6,201,234 B1 | 3/2001 | Chow et al. |
| 6,208,894 B1 | 3/2001 | Schulman et al. |
| 6,208,896 B1 | 3/2001 | Mulhauser |
| 6,214,032 B1 | 4/2001 | Loeb et al. |
| 6,289,246 B1 | 9/2001 | Money |
| 6,315,721 B2 | 11/2001 | Schulman et al. |
| 6,317,628 B1 | 11/2001 | Linder et al. |
| 6,324,426 B1 | 11/2001 | Thompson |
| 6,355,990 B1 | 3/2002 | Mitchell |
| 6,363,277 B1 | 3/2002 | Dooley et al. |
| 6,370,046 B1 | 4/2002 | Nebrigic et al. |
| 6,392,580 B1 | 5/2002 | Swanson |
| 6,429,632 B1 | 8/2002 | Forbes et al. |
| 6,442,422 B1 | 8/2002 | Duckert |
| 6,516,227 B1 | 2/2003 | Meadows et al. |
| 6,525,949 B1 | 2/2003 | Johnson et al. |
| 6,553,263 B1 | 4/2003 | Meadows et al. |
| 6,597,950 B2 | 7/2003 | Linder |
| 6,609,029 B1 | 8/2003 | Mann |
| 6,631,296 B1 | 10/2003 | Parramon et al. |
| 6,668,193 B2 | 12/2003 | Ware et al. |
| 6,690,974 B2 | 2/2004 | Archer |
| 6,704,597 B1 | 3/2004 | Ware et al. |
| 6,741,892 B1 | 5/2004 | Meadows |
| 6,745,077 B1 | 6/2004 | Griffith et al. |
| 6,756,772 B2 | 6/2004 | McGinnis |
| 6,799,070 B2 | 9/2004 | Wolfe et al. |
| 6,826,430 B2 | 11/2004 | Faltys et al. |
| 6,856,838 B2 | 2/2005 | Parramon et al. |
| 6,871,090 B1 | 3/2005 | He et al. |
| 6,873,874 B2 | 3/2005 | Ware et al. |
| 6,909,915 B2 | 6/2005 | Greatbatch et al. |
| 6,934,584 B1 | 8/2005 | Wong et al. |
| 7,009,313 B1 | 3/2006 | Parramon et al. |
| 7,079,900 B2 | 7/2006 | Greenburg et al. |
| 7,127,298 B1 | 10/2006 | He et al. |
| 7,151,963 B2 | 12/2006 | Havel et al. |
| 7,177,698 B2 | 2/2007 | Klosterman et al. |
| 7,200,434 B2 | 4/2007 | Havel et al. |
| 7,203,539 B2 | 4/2007 | Ware et al. |
| 7,203,549 B2 | 4/2007 | Schommer et al. |
| 7,235,050 B2 | 6/2007 | Schulman et al. |
| 7,263,406 B2 | 8/2007 | Toy et al. |
| 7,272,445 B2 | 9/2007 | Phillips et al. |
| 7,304,871 B2 | 12/2007 | Ito et al. |
| 7,307,385 B2 | 12/2007 | Yamamoto et al. |
| 7,400,283 B1 | 7/2008 | Zhu |
| 7,444,181 B2 | 10/2008 | Shi et al. |
| 7,483,748 B2 | 1/2009 | Torgerson et al. |
| 7,519,428 B1 | 4/2009 | Palmer |
| 7,539,538 B2 | 5/2009 | Parramon et al. |
| 7,623,916 B2 | 11/2009 | Julian |
| 7,801,600 B1 | 9/2010 | Carbunaru et al. |
| 7,801,602 B2 | 9/2010 | McClure et al. |
| 7,805,189 B2 | 9/2010 | Stein et al. |
| 7,872,884 B2 | 1/2011 | Parramon et al. |
| 7,881,803 B2 | 2/2011 | Parramon et al. |
| 7,890,182 B2 | 2/2011 | Parramon et al. |
| 7,949,393 B2 | 5/2011 | Varrachio et al. |
| 8,131,377 B2 | 3/2012 | Shi et al. |
| 8,175,719 B2 | 5/2012 | Shi et al. |
| 8,219,196 B2 | 7/2012 | Torgerson |
| 8,538,548 B2 | 9/2013 | Shi et al. |
| 8,606,362 B2 | 12/2013 | He et al. |
| 8,620,436 B2 | 12/2013 | Parramon et al. |
| 8,649,858 B2 | 2/2014 | Griffith et al. |
| 8,768,453 B2 | 7/2014 | Parramon et al. |
| 8,781,598 B2 | 7/2014 | Shi et al. |
| 9,002,465 B2 | 4/2015 | Ranu |
| 9,008,790 B2 | 4/2015 | Griffith et al. |
| 9,014,813 B2 | 4/2015 | Foutz et al. |
| 9,037,241 B2 | 5/2015 | Lamont et al. |
| 9,061,140 B2 | 6/2015 | Shi et al. |
| 9,155,891 B2 | 10/2015 | Archer |
| 9,174,051 B2 | 11/2015 | Marnfeldt et al. |
| 9,220,901 B2 | 12/2015 | Gururaj et al. |
| 9,233,254 B2 | 1/2016 | Nimmagadda et al. |
| 9,259,574 B2 | 2/2016 | Aghassian et al. |
| 9,308,373 B2 | 4/2016 | Lee |
| 9,314,632 B2 | 4/2016 | Marnfeldt et al. |
| 9,327,135 B2 | 5/2016 | Vansickle et al. |
| 9,352,162 B2 | 5/2016 | Lamont et al. |
| 9,397,639 B2 | 7/2016 | Feldman et al. |
| 9,616,233 B2 | 4/2017 | Shi et al. |
| 9,731,116 B2 | 8/2017 | Chen |
| 9,750,938 B2 | 9/2017 | Ternes et al. |
| 9,872,995 B2 | 1/2018 | Nimmagadda et al. |
| 10,420,935 B2 | 9/2019 | Illegems et al. |
| 10,525,252 B2 | 1/2020 | Feldman et al. |
| 2002/0072770 A1 | 6/2002 | Pless |
| 2002/0077670 A1 | 6/2002 | Archer et al. |
| 2002/0087196 A1 | 7/2002 | Ware et al. |
| 2003/0074037 A1 | 4/2003 | Moore et al. |
| 2003/0125773 A1 | 7/2003 | Havel et al. |
| 2003/0187484 A1 | 10/2003 | Davis et al. |
| 2003/0204224 A1 | 10/2003 | Torgerson et al. |
| 2003/0234631 A1 | 12/2003 | Schulman et al. |
| 2004/0059392 A1 | 3/2004 | Parramon et al. |
| 2004/0111123 A1 | 6/2004 | Ware et al. |
| 2004/0167407 A1 | 8/2004 | Roberts |
| 2004/0183607 A1 | 9/2004 | Moore |
| 2005/0021108 A1 | 1/2005 | Klosterman et al. |
| 2005/0027318 A1 | 2/2005 | Ware et al. |

(56) References Cited

U.S. PATENT DOCUMENTS

| | | |
|---|---|---|
| 2005/0057905 A1 | 3/2005 | He et al. |
| 2005/0075684 A1 | 4/2005 | Phillips et al. |
| 2005/0075685 A1 | 4/2005 | Forsberg et al. |
| 2005/0075686 A1 | 4/2005 | Phillips et al. |
| 2005/0075688 A1 | 4/2005 | Toy et al. |
| 2005/0075689 A1 | 4/2005 | Toy et al. |
| 2005/0075690 A1 | 4/2005 | Toy et al. |
| 2005/0075691 A1 | 4/2005 | Phillips et al. |
| 2005/0075692 A1 | 4/2005 | Schommer et al. |
| 2005/0165451 A1 | 7/2005 | Ware et al. |
| 2005/0212501 A1 | 9/2005 | Acatrinei |
| 2005/0226019 A1 | 10/2005 | Nastase |
| 2005/0228453 A1 | 10/2005 | Havel et al. |
| 2005/0270812 A1 | 12/2005 | Vinciarelli |
| 2005/0275382 A1 | 12/2005 | Stessman et al. |
| 2006/0066379 A1 | 3/2006 | Hopsecger |
| 2006/0173493 A1 | 8/2006 | Armstrong et al. |
| 2006/0276857 A1 | 12/2006 | Forsberg et al. |
| 2007/0016263 A1 | 1/2007 | Armstrong et al. |
| 2007/0038250 A1 | 2/2007 | He et al. |
| 2007/0097719 A1 | 5/2007 | Parramon et al. |
| 2007/0100399 A1 | 5/2007 | Parramon et al. |
| 2007/0135868 A1 | 6/2007 | Shi et al. |
| 2007/0146020 A1 | 6/2007 | Williams |
| 2007/0208261 A1 | 9/2007 | Maniak et al. |
| 2007/0212596 A1 | 9/2007 | Nebrigic et al. |
| 2007/0276450 A1 | 11/2007 | Meadows et al. |
| 2007/0288068 A1 | 12/2007 | Toy et al. |
| 2008/0015657 A1 | 1/2008 | Haefner |
| 2008/0048729 A1 | 2/2008 | Ehrenreich |
| 2008/0114231 A1 | 5/2008 | Dai et al. |
| 2008/0127478 A1 | 6/2008 | Phillips et al. |
| 2008/0136386 A1 | 6/2008 | Nastase |
| 2008/0319497 A1 | 12/2008 | Griffith et al. |
| 2008/0319514 A1 | 12/2008 | Shi et al. |
| 2009/0018618 A1 | 1/2009 | Parramon et al. |
| 2009/0024187 A1 | 1/2009 | Erickson et al. |
| 2009/0043244 A1 | 2/2009 | Inan |
| 2009/0062883 A1 | 3/2009 | Meadows et al. |
| 2009/0316743 A1 | 12/2009 | Alfrey |
| 2010/0164579 A1 | 7/2010 | Acatrinei |
| 2010/0211132 A1 | 8/2010 | Nimmagadda et al. |
| 2010/0256712 A1 | 10/2010 | Varrichio et al. |
| 2010/0268309 A1 | 10/2010 | Parramon et al. |
| 2011/0110127 A1 | 5/2011 | Lee |
| 2011/0121801 A1 | 5/2011 | Scaldaferri et al. |
| 2012/0095529 A1 | 4/2012 | Parramon et al. |
| 2012/0239108 A1 | 9/2012 | Foutz |
| 2013/0023943 A1 | 1/2013 | Parramon et al. |
| 2013/0073008 A1 | 3/2013 | Ternes et al. |
| 2013/0184794 A1 | 7/2013 | Feldman et al. |
| 2013/0289661 A1 | 10/2013 | Griffith et al. |
| 2013/0289665 A1 | 10/2013 | Marnfeldt et al. |
| 2013/0310897 A1 | 11/2013 | Marnfeldt et al. |
| 2013/0338732 A1 | 12/2013 | Foutz |
| 2014/0018883 A1 | 1/2014 | Shi et al. |
| 2014/0266375 A1 | 9/2014 | Feldman et al. |
| 2015/0066108 A1 | 3/2015 | Shi et al. |
| 2015/0134029 A1 | 5/2015 | Ozawa et al. |
| 2015/0144183 A1 | 5/2015 | Yang et al. |
| 2015/0157861 A1 | 6/2015 | Aghassian |
| 2015/0360038 A1 | 12/2015 | Zottola et al. |
| 2016/0051825 A1 | 2/2016 | Ter-Petrosyan et al. |
| 2017/0095667 A1* | 4/2017 | Yakovlev ............. A61B 5/0022 |
| 2018/0071511 A1 | 3/2018 | Marnfeldt et al. |
| 2018/0071512 A1 | 3/2018 | Feldman et al. |
| 2018/0071513 A1 | 3/2018 | Weiss et al. |
| 2018/0071520 A1 | 3/2018 | Weerakoon et al. |
| 2018/0071527 A1 | 3/2018 | Feldman et al. |
| 2019/0038899 A1* | 2/2019 | Lo ........................ A61N 1/0551 |
| 2019/0083796 A1 | 3/2019 | Weerakoon et al. |
| 2020/0346019 A1 | 11/2020 | Weiss et al. |

FOREIGN PATENT DOCUMENTS

| | | |
|---|---|---|
| WO | 2000/000251 | 1/2000 |
| WO | 2000/021607 | 4/2000 |
| WO | 2002/009808 | 2/2002 |
| WO | 2003/047685 | 6/2003 |
| WO | 2005/042087 | 5/2005 |
| WO | 2005/042092 | 5/2005 |
| WO | 2005/042093 | 5/2005 |
| WO | 2005/042094 | 5/2005 |
| WO | 2005/042095 | 5/2005 |
| WO | 2005/042096 | 5/2005 |
| WO | 2005/042097 | 5/2005 |
| WO | 2005/042098 | 5/2005 |
| WO | 2007/070727 | 6/2007 |
| WO | 2010/096131 | 8/2010 |
| WO | 2011/033489 | 3/2011 |

OTHER PUBLICATIONS

Document # IPCOM000016848D, published at www.ip.com (Jul. 18, 2003).

Document # IPCOM000007552D, published at www.ip.com (Apr. 4, 2002).

M. Ghovanloo, et al., "A Compact Large Voltage-Compliance High Output-Impedance Programmable Current Source for Implantable Microstimulators," IEEE Transactions on Biomedical Engineering, vol. 52, No. 1, Jan. 2005.

M. Sivaprakasam et al., "A Variable Range Bi-Phasic Current Stimulus Driver Circuitry for an Implantable Retinal Prosthetic Device," IEEE Journal of Solid-State Circuits, vol. 40, No. 3, Mar. 2005.

A. Uranga, et al., "Special Section of Functional Electrical Stimulation: An Integrated Implantable Electrical Sacral Root Stimulator for Bladder Control," International Neuromodulation Society, Neuromodulation, vol. 5, No. 4, 2002.

Emilia Noorsal, et al., "A Neural Stimulator Frontend With High-Voltage Compliance and Programmable Pulse Shape for Epiretinal Implants", IEEE Journal of Solid-State Circuits, IEEE Service Center, Piscataway, NJ, USA, vol. 47, No. I, Jan. 1, 2012.

Pylarinos, Louie, "Charge Pumps: An Overview" in *Proceedings of the IEEE International Symposium on Circuits and Systems*, 2003.

Chebli, Robert, et al., "A Wide Tuning Range Voltage-Controlled Ring Oscillator Dedicated to Ultrasound Transmitter", presented at International Conference on Microelectronics, Dec. 2004.

Sun, et al, "Power Management in a Bio-telemetry Application", Power Electronics Specialists Conference 2005, ISBN: 978-0-7803-9033-1, pp. 1182-1190, Jan. 1, 2005.

International Search Report and Written Opinion regarding corresponding PCT Application No. PCT/US2020/049054, mailed Nov. 13, 2020.

* cited by examiner

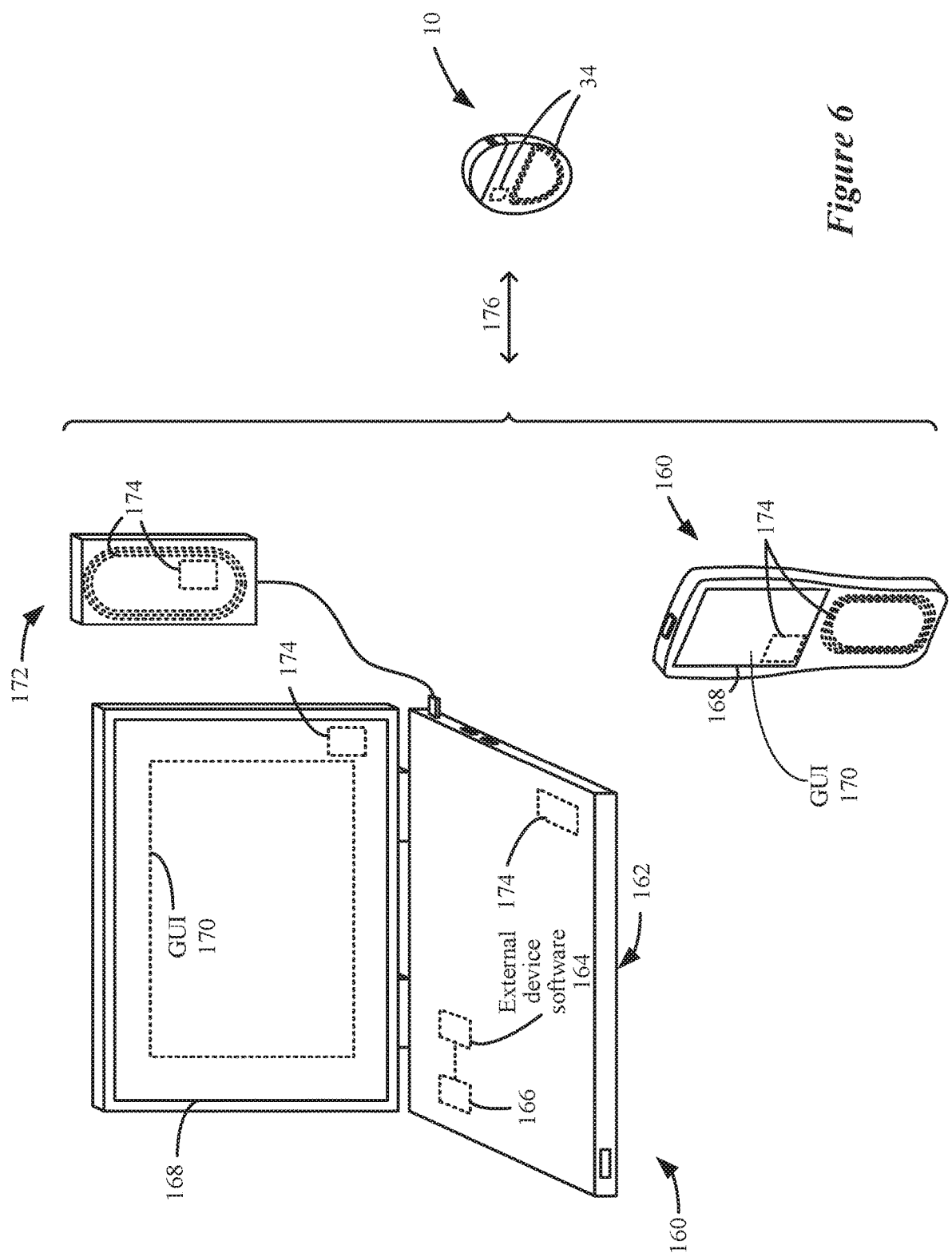

*Pulse Program I (A = 4.0 mA)*

| Memory Location | 20 | 19 | 18 | 17 | 16 | 15 | 14 | 13 | 12 | 11 | 10 | 9 | 8 | 7 | 6 | 5 | 4 | 3 | 2 | 1 | 0 |
|---|---|---|---|---|---|---|---|---|---|---|---|---|---|---|---|---|---|---|---|---|---|
| X | N | AR | | 0 | N | | D1 | | | | | | | | 0 | | | | | | |
| X+1 | N | S | | 0 | N | | D2 | | | | | | | | 4 mA | | | | | | |
| X+2 | N | AD | | 0 | | 0 | | | | | | | Y | N | N | | D3 | | | | |
| X+3 | N | AR | | 0 | N | | D4 | | | | | | | | 4 mA | | | | | | |
| X+4 | N | Del | | - | N | - | - | - | N | N | Y | | D5 | | | | | | | | |
| X+5 | N | Del | | - | Y | - | - | - | N | N | N | | D6 | | | | | | | | |

*Pulse Program J*
A = 2.0 mA

*Pulse Program K*
A = 6.0 mA

*Pulse Program L*
A = 3.8 mA

*Pulse Program M*
A = 4.2 mA

*Pulse Program N*
A = 1.0 mA

*Steering Program A*

| Memory Location | | | | | | | | | | |
|---|---|---|---|---|---|---|---|---|---|---|
| Y | - | E4=0% | - | E3=0% | C | E2=100% | A | E1=100% | | |
| Y+1 | - | E8=0% | - | E7=0% | - | E6=0% | - | E5=0% | | |

*Aggregate Program 1*

| | INTERRUPT | NUMBER OF REPEATS | STEERING PROGRAM | PULSE PROGRAM |
|---|---|---|---|---|
| Memory Location | 20 | 19 18 17 16 15 14 13 12 | 11 10 9 8 | 7 6 5 4 3 2 1 0 |
| Z | N | 10 | A | I |
| Z+1 | N | 20 | A | J |
| Z+2 | N | 5 | A | K |
| Z+3 | N | 10 | A | J |
| Z+4 | N | 10 | A | I |
| Z+5 | N | 10 | A | J |
| Z+6 | N | 10 | A | I |
| Z+7 | N | 10 | A | L |
| Z+8 | N | 10 | A | M |
| Z+9 | N | 3 | A | N |
| Z+10 | N | 10 | A | I |

*Figure 7C*

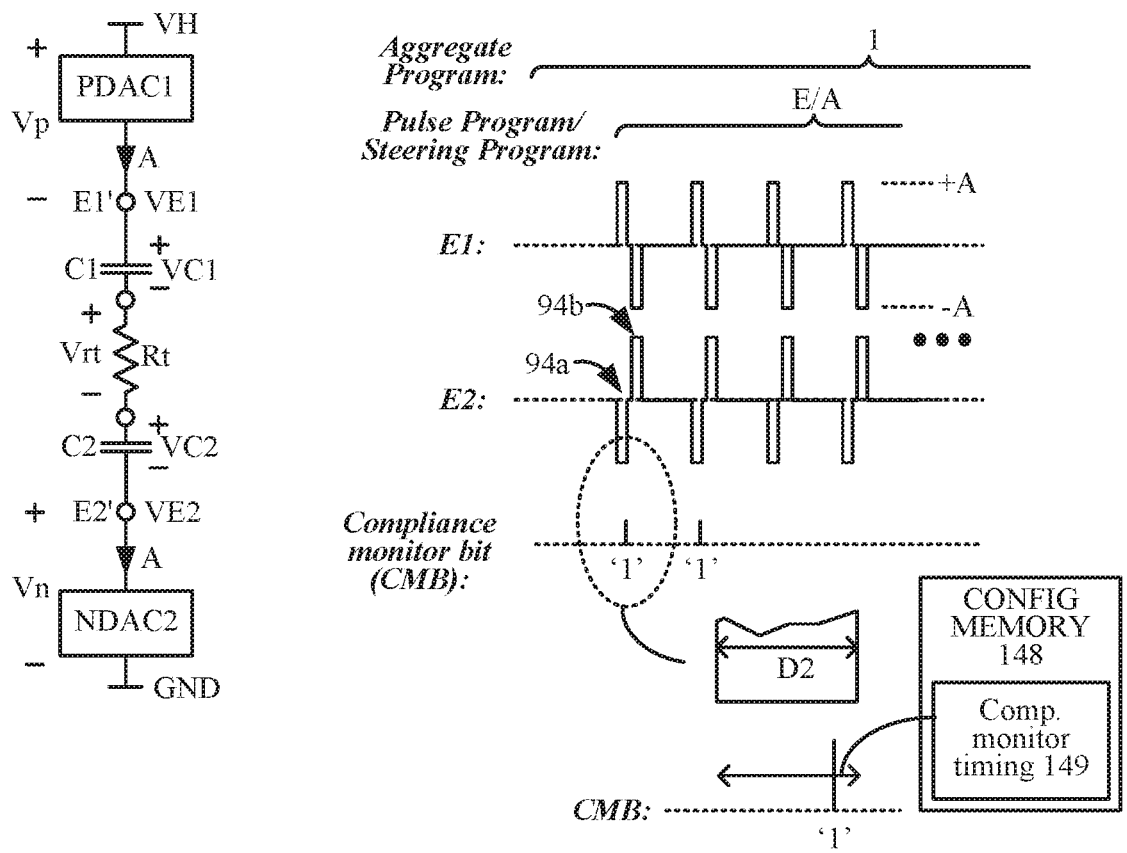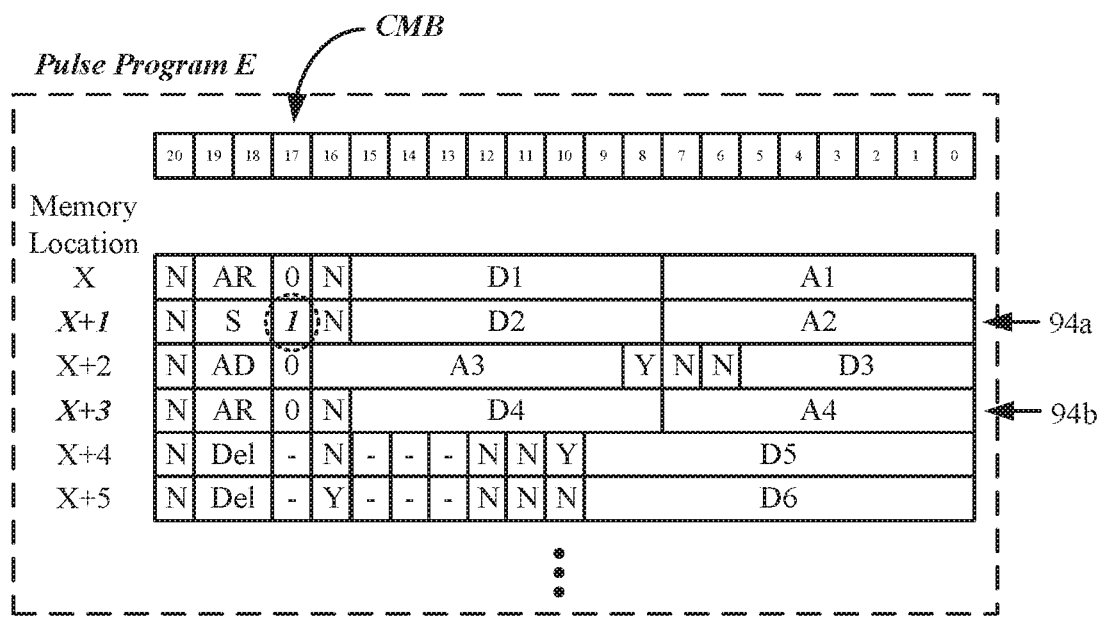
*Figure 8A*

VH gain table 232

| Gain | VH | Switch Configuration (<S>) | |
|---|---|---|---|
| | | φ1 | φ2 |
| 1 | Vbat | <S1_1> | <S1_2> |
| 5/4 (1.25) | 1.25*Vbat | <S2_1> | <S2_2> |
| 4/3 (1.33) | 1.33*Vbat | <S3_1> | <S3_2> |
| 7/5 (1.4) | 1.4*Vbat | | |
| 3/2 (1.5) | 1.5*Vbat | ... | ... |
| 8/5 (1.6) | 1.6*Vbat | | |
| 5/3 (1.67) | 1.67*Vbat | | |
| 7/4 (1.75) | 1.75*Vbat | | |
| 2 | 2*Vbat | | |
| 7/3 (2.33) | 2.33*Vbat | | |
| 5/2 (2.5) | 2.5*Vbat | | |
| 8/9 (2.67) | 2.67*Vbat | | |
| 3 | 3*Vbat | | |
| 7/2 (3.5) | 3.5*Vbat | <S14_1> | <S14_2> |
| 4 | 4*Vbat | | |
| 5 | 5*Vbat | <S16_1> | <S16_2> |
| 6 | 6*Vbat | ... | ... |
| 7 | 7*Vbat | | |
| 8 | 8*Vbat | <S19_1> | <S19_2> |

| Block | Block Duration (ms) | # pulses | Pulse program | Amp (mA) |
|---|---|---|---|---|
| 1 | 100 | 10 | I | 4.0 |
| 2 | 200 | 20 | J | 2.0 |
| 3 | 50 | 5 | K | 6.0 |
| 4 | 100 | 10 | J | 2.0 |
| 5 | 100 | 10 | I | 4.0 |
| 6 | 100 | 10 | J | 2.0 |
| 7 | 100 | 10 | I | 4.0 |
| 8 | 100 | 10 | L | 3.8 |
| 9 | 100 | 10 | M | 4.2 |
| 10 | 30 | 3 | N | 1.0 |
| 11 | 100 | 10 | I | 4.0 |

*Figure 11B*

VH management algorithm 250

Set VH(opt) for 'b' groups to VH(opt) of next group, and consolidate next group into preceding 'b' group for compliance voltage purposes (Fig. 17C); leave VH(opt) for 'a' groups to its original value.

↓

340

Fig. 18: Compile programming for IPG (e.g., aggregate program and related pulse and steering programs). Pulse programs may already have been determined upon waveform definition (Fig. 7C), or they may be determined using information from table 313 or from the waveform 299 itself.

342: Include VH adjustment instructions (e.g., set INT(VH_adj) in relevant aggregate instructions) where VH must change.

344: include VH(opt) values in the programming instructions (e.g., in the aggregate instructions), or compile a VH(opt) table 360.

346: Include VH measurements instructions (See Fig. 12C)

Waveform 1:   Number of Blocks = 11   Number of VH groups: 9

| Group 6 / Block 6 | Block 7 | Block 8 | Block 9 | Group 8 / Block 10 |
|---|---|---|---|---|
| Pulse Prog J | Pulse Prog I | Pulse Prog L | Pulse Prog M | Pulse Prog N |
| Steering Prog A | Steering Prog A | Steering Prog A | Steering Prog A | Steering Prog A |
| Anode(s): E1 (100%) | Anode(s): E1 (100%) | Anode(s): E1 (100%) | Anode(s): E1 (100%) | Anode(s): E1 (100%) |
| Cathode(s): E2 (100%) | Cathode(s): E2 (100%) | Cathode(s): E2 (100%) | Cathode(s): E2 (100%) | Cathode(s): E2 (100%) |
| Amp: 2 mA | Amp: 4 mA | Amp: 3.8 mA | Amp: 4.2 mA | Amp: 1 mA |
| Amp Scale: 100% | Amp Scale: 100% | Amp Scale: 100% | Amp Scale: 100% | Amp Scale: 100% |
| Freq: 100 Hz | Freq: 100 Hz | Freq: 100 Hz | Freq: 100 Hz | Freq: 100 Hz |
| Pulse Period: 10 ms | Pulse Period: 10 ms | Pulse Period: 10 ms | Pulse Period: 10 ms | Pulse Period: 10 ms |
| # Pulses: 10 | # Pulses: 10 | # Pulses: 10 | # Pulses: 10 | # Pulses: 3 |
| Block Duration: 100 ms | Block Duration: 100 ms | Block Duration: 100 ms | Block Duration: 100 ms | Block Duration: 30 ms |
| Func: n/a | Func: n/a | Func: n/a | Func: n/a | Func: n/a |
| VH(opt): x V | VH(opt): n/a | VH(opt): n/a | VH(opt): n/a | VH(opt): x V |

Group 7
Group duration: 300 ms
VH(opt): x V

— 196

GUI 170

*Figure 13C*

| Group | Group Duration (ms) | Block | Block Duration (ms) | # pulses | Pulse program | Amp (mA) |
|---|---|---|---|---|---|---|
| 1 | 100 | 1 | 100 | 10 | I | 4.0 |
| 2 | 200 | 2 | 200 | 20 | J | 2.0 |
| 3 | 50 | 3 | 50 | 5 | K | 6.0 |
| 4 | 100 | 4 | 100 | 10 | J | 2.0 |
| 5 | 100 | 5 | 100 | 10 | I | 4.0 |
| 6 | 100 | 6 | 100 | 10 | J | 2.0 |
| 7 | 300 | 7 | 100 | 10 | I | 4.0 |
|  |  | 8 | 100 | 10 | L | 3.8 |
|  |  | 9 | 100 | 10 | M | 4.2 |
| 8 | 30 | 10 | 30 | 3 | N | 1.0 |
| 9 | 100 | 11 | 100 | 10 | I | 4.0 |

*Figure 13D*

| Group | Group Duration (ms) | VH(opt) (V) | tr (ms) | tf (ms) | Block | Block Duration (ms) | # pulses | Pulse program | Amp (mA) |
|---|---|---|---|---|---|---|---|---|---|
| 1 | 100 | VH_G1=7.5 | n/a | n/a | 1 | 100 | 10 | I | 4.0 |
| 2 | 200 | VH_G2=6 | n/a | tf1_2=40 | 2 | 200 | 20 | J | 2.0 |
| 3 | 50 | VH_G3=9 | tr2_3=48 | n/a | 3 | 50 | 5 | K | 6.0 |
| 4 | 100 | VH_G4=6 | n/a | tf3_4=50 | 4 | 100 | 10 | J | 2.0 |
| 5 | 100 | VH_G5=7.5 | tr4_5=25 | n/a | 5 | 100 | 10 | I | 4.0 |
| 6 | 100 | VH_G6=6 | n/a | tf5_6=40 | 6 | 100 | 10 | J | 2.0 |
| 7 | 300 | VH_G7=8 | tr6_7=30 | n/a | 7 | 100 | 10 | I | 4.0 |
| | | | | | 8 | 100 | 10 | L | 3.8 |
| | | | | | 9 | 100 | 10 | M | 4.2 |
| 8 | 30 | VH_G8=5 | n/a | tf7_8=100 | 10 | 30 | 3 | N | 1.0 |
| 9 | 100 | VH_G9=7.5 | tr8_9=65 | n/a | 11 | 100 | 10 | I | 4.0 |

*Figure 14C*

| Group | Group Duration (ms) | VH(opt) (V) | tr (ms) | tf (ms) | Block | Block Duration (ms) | # pulses | Pulse program | Amp (mA) |
|---|---|---|---|---|---|---|---|---|---|
| 1 | 100 | VH_G1=7.5 | n/a | n/a | 1 | 100 | 10 | I | 4.0 |
| 2 | 200 | VH_G2=6 | n/a | tf1_2=40 | 2 | 200 | 20 | J | 2.0 |
| 3 | 50 | VH_G3=9 | tr2_3=48 | n/a | 3 | 50 | 5 | K | 6.0 |
| 4 | 100 | VH_G4=6 | n/a | tf3_4=50 | 4 | 100 | 10 | J | 2.0 |
| 5 | 100 | VH_G5=7.5 | tr4_5=25 | n/a | 5 | 100 | 10 | I | 4.0 |
| 6 | 100 | VH_G6=6 | n/a | tf5_6=40 | 6 | 100 | 10 | J | 2.0 |
| 7 | 300 | VH_G7=8 | tr6_7=30 | n/a | 7 | 100 | 10 | I | 4.0 |
| | | | | | 8 | 100 | 10 | L | 3.8 |
| | | | | | 9 | 100 | 10 | M | 4.2 |
| 8 | 30 | VH_G8=5 | tr8_9=65 | tf7_8=100 | 10 | 30 | 3 | N | 1.0 |
| 9 | 100 | VH_G9=7.5 | n/a | n/a | 11 | 100 | 10 | I | 4.0 |

*Figure 15A*

| Group | Group Duration (ms) | VH(opt) (V) | tr (ms) | tf (ms) | Block | Block Duration (ms) | # pulses | Pulse program | Amp (mA) |
|---|---|---|---|---|---|---|---|---|---|
| 1 | 100 | VH_G1=7.5 | n/a | tf7_1=10 | 1 | 100 | 10 | I | 4.0 |
| 2 | 200 | VH_G2=6 | n/a | tf1_2=40 | 2 | 200 | 20 | J | 2.0 |
| 3 | 50 | VH_G3=9 | tr2_3=48 | n/a | 3 | 50 | 5 | K | 6.0 |
| 4 | 100 | VH_G4=6 | n/a | tf3_4=50 | 4 | 100 | 10 | J | 2.0 |
| 5 | 100 | VH_G5=7.5 | tr4_5=25 | n/a | 5 | 100 | 10 | I | 4.0 |
| 6 | 100 | VH_G6=6 | n/a | tf5_6=40 | 6 | 100 | 10 | J | 2.0 |
| 7 | 430 | VH_G7=8 | tr6_7=30 | n/a | 7 | 100 | 10 | I | 4.0 |
|   |   |   |   |   | 8 | 100 | 10 | L | 3.8 |
|   |   |   |   |   | 9 | 100 | 10 | M | 4.2 |
|   |   |   |   |   | 10 | 30 | 3 | N | 1.0 |
|   |   |   |   |   | 11 | 100 | 10 | I | 4.0 |

*Figure 16A*

| Group | Group Duration (ms) | VH(opt) (V) | tr (ms) | tf (ms) | Block | Block Duration (ms) | # pulses | Pulse program | Amp (mA) |
|---|---|---|---|---|---|---|---|---|---|
| 1 | 100 | VH_G1=7.5 | n/a | tf7_1=10 | 1 | 100 | 10 | I | 4.0 |
| 2a | 150 | VH_G2a=6 | n/a | tf1_2a=40 | 2 | 150 | 15 | J | 2.0 |
| 2b | 50 | VH_G2b=6 | n/a | n/a | 2 | 50 | 5 | J | 2.0 |
| 3 | 50 | VH_G3=9 | tr2b_3=48 | n/a | 3 | 50 | 5 | K | 6.0 |
| 4a | 70 | VH_G4a=6 | n/a | tf3_4a=50 | 4 | 70 | 7 | J | 2.0 |
| 4b | 30 | VH_G4b=6 | n/a | n/a | 4 | 30 | 3 | J | 2.0 |
| 5 | 100 | VH_G5=7.5 | tr4b_5=25 | n/a | 5 | 100 | 10 | I | 4.0 |
| 6a | 70 | VH_G6a=6 | n/a | tf5_6a=40 | 6 | 70 | 7 | J | 2.0 |
| 6b | 30 | VH_G6b=6 | n/a | n/a | 6 | 30 | 3 | J | 2.0 |
| 7 | 430 | VH_G7=8 | tr6b_7=30 | n/a | 7 | 100 | 10 | I | 4.0 |
| | | | | | 8 | 100 | 10 | L | 3.8 |
| | | | | | 9 | 100 | 10 | M | 4.2 |
| | | | | | 10 | 30 | 3 | N | 1.0 |
| | | | | | 11 | 100 | 10 | I | 4.0 |

*Figure 17B*

Aggregate Program 1

| Memory Location | VH(opt) | INTERRUPT INT(VH_adj) | NUMBER OF REPEATS | STEERING PROGRAM | PULSE PROGRAM | Group | Block |
|---|---|---|---|---|---|---|---|
| Z | VH G1=7.5 | Y | 10 | A | I (4.0 mA) | 1 | 1 |
| Z+1 | VH G2a=6 | Y | 15 | A | J (2.0 mA) | 2a | 2 |
| Z+2 | VH G2b=9 | Y | 5 | A | J (2.0 mA) | 2b | 2 |
| Z+3 | | N | 5 | A | K (6.0 mA) (set CMB) | 2b | 3 |
| Z+4 | VH G4a=6 | Y | 7 | A | J (2.0 mA) | 4a | 4 |
| Z+5 | VH G4b=7.5 | Y | 3 | A | J (2.0 mA) | 4b | 4 |
| Z+6 | | N | 10 | A | F' (4.0 mA) (set CMB) | 4b | 5 |
| Z+7 | VH G6a=6 | Y | 7 | A | J (2.0 mA) | 6a | 6 |
| Z+8 | VH G6b=8 | Y | 3 | A | F' (4.0 mA) (set CMB) | 6b | 6 |
| Z+9 | | N | 10 | A | F' (4.0 mA) (set CMB) | 6b | 7 |
| Z+10 | | N | 10 | A | L (3.8 mA) | 6b | 8 |
| Z+11 | | N | 10 | A | M (4.2 mA) (set CMB) | 6b | 9 |
| Z+12 | | N | 3 | A | N (1.0 mA) | 6b | 10 |
| Z+13 | | N | 10 | A | I (4.0 mA) | 6b | 11 |

*Figure 20B*

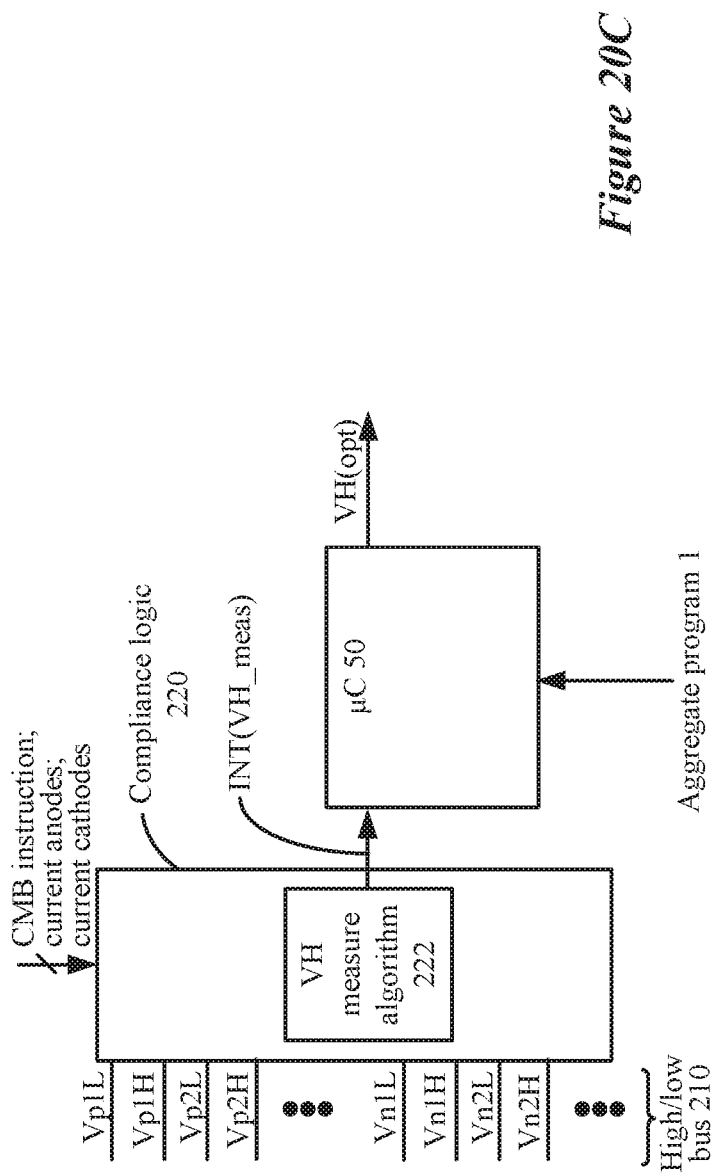

*Aggregate Program 1*

| Memory Location | VH(opt) | INTERRUPT | NUMBER OF REPEATS | STEERING PROGRAM | PULSE PROGRAM | Group | Block |
|---|---|---|---|---|---|---|---|
| Z | VH G1=7.5 | Y | 10 | A | I' (4.0 mA) (set CMB) | 1 | 1 |
| Z+1 | VH G2a=6 | Y | 4 | A | J (2.0 mA) | 2a | 2 |
| Z+2 | | N | 11 | A | J' (2.0 mA) (set CMB) | 2a | 2 |
| Z+3 | VH G2b=9 | Y | 5 | A | J (2.0 mA) | 2b | 2 |
| Z+4 | | N | 5 | A | K (6.0 mA) (set CMB) | 2b | 3 |
| Z+5 | VH G4a=6 | Y | 5 | A | J (2.0 mA) | 4a | 4 |
| Z+6 | | N | 2 | A | J' (2.0 mA) (set CMB) | 4a | 4 |
| Z+7 | VH G4b=7.5 | Y | 3 | A | I' (4.0 mA) (set CMB) | 4b | 4 |
| Z+8 | | N | 10 | A | J' (2.0 mA) (set CMB) | 4b | 5 |
| Z+9 | VH G6a=6 | Y | 4 | A | J (2.0 mA) | 6a | 6 |
| Z+10 | | N | 3 | A | I' (4.0 mA) (set CMB) | 6a | 6 |
| Z+11 | VH G6b=8 | Y | 3 | A | I' (4.0 mA) (set CMB) | 6b | 6 |
| Z+12 | | N | 10 | A | L (3.8 mA) (set CMB) | 6b | 7 |
| Z+13 | | N | 10 | A | M (4.2 mA) (set CMB) | 6b | 8 |
| Z+14 | | N | 3 | A | N (1.0 mA) (set CMB) | 6b | 9 |
| Z+15 | | N | 10 | A | I (4.0 mA) (set CMB) | 6b | 10 |
| Z+16 | | | | | | 6b | 11 |

*Figure 20E*

*Aggregate Program 1*

| Memory Location | VH(opt) INT(VH_adj) | INTERRUPT | NUMBER OF REPEATS | STEERING PROGRAM | PULSE PROGRAM | Group | Block |
|---|---|---|---|---|---|---|---|
| Z | VH G1=7.5 | Y | 10 | A | I (4.0 mA) (set CMB) | 1 | 1 |
| Z+1 | VH G2a=6 | Y | 15 | A | J (2.0 mA) (set CMB) | 2a | 2 |
| Z+2 | VH G2b=9 | Y | 5 | A | J (2.0 mA) (set CMB) | 2b | 2 |
| Z+3 | | N | 5 | A | K (6.0 mA) (set CMB) | | 3 |
| Z+4 | VH G4a=6 | Y | 7 | A | J (2.0 mA) (set CMB) | 4a | 4 |
| Z+5 | VH G4b=7.5 | Y | 3 | A | J (2.0 mA) (set CMB) | 4b | 4 |
| Z+6 | | N | 10 | A | I (4.0 mA) (set CMB) | | 5 |
| Z+7 | VH G6a=6 | Y | 7 | A | J (2.0 mA) (set CMB) | 6a | 6 |
| Z+8 | VH G6b=8 | Y | 3 | A | I (4.0 mA) (set CMB) | 6b | 6 |
| Z+9 | | N | 10 | A | I (4.0 mA) (set CMB) | | 7 |
| Z+10 | | N | 10 | A | L (3.8 mA) (set CMB) | | 8 |
| Z+11 | | N | 10 | A | M (4.2 mA) (set CMB) | | 9 |
| Z+12 | | N | 3 | A | N (1.0 mA) (set CMB) | | 10 |
| Z+13 | | N | 10 | A | I (4.0 mA) (set CMB) | | 11 |

*Figure 21B*

| Memory location | VH(opt) |
|---|---|
| Z | VH_G1=? |
| Z+1 | VH_G2a=? |
| Z+2 | VH_G2b=? |
| Z+4 | VH_G4a=? |
| Z+5 | VH_G4b=? |
| Z+7 | VH_G6a=? |
| Z+8 | VH_G6b=? |

← VH(opt) table 360

⇒

| Memory location | VH(opt) |
|---|---|
| Z | VH_G1=7.5 |
| Z+1 | VH_G2a=6 |
| Z+2 | VH_G2b=9 |
| Z+4 | VH_G4a=6 |
| Z+5 | VH_G4b=7.5 |
| Z+7 | VH_G6a=6 |
| Z+8 | VH_G6b=8 |

← VH(opt) table 360

*Figure 22*

MANAGEMENT OF COMPLIANCE VOLTAGE FOR A STIMULATOR DEVICE

FIELD OF THE INVENTION

The present invention relates generally to implantable medical devices, and more particularly to improved compliance voltage monitoring and adjustment in an implantable pulse generator.

INTRODUCTION

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable medical device system, including a Deep Brain Stimulation (DBS) system.

As shown in FIGS. 1A-1C, an SCS system typically includes an Implantable Pulse Generator (IPG) 10, which includes a biocompatible device case 12 formed of a conductive material such as titanium for example. The case 12 typically holds the circuitry and power source (e.g., battery) 14 (FIG. 1C) necessary for the IPG 10 to function, although IPGs can also be powered via external RF energy and without a battery. The IPG 10 is coupled to electrodes 16 via one or more electrode leads 18, such that the electrodes 16 form an electrode array 20. The electrodes 16 are carried on a flexible body 22, which also houses the individual signal wires 24 coupled to each electrode. In the illustrated embodiment, there are eight electrodes (Ex) on two leads 18 for a total of sixteen electrodes 16, although the number of leads and electrodes is application specific and therefore can vary. The leads 18 couple to the IPG 10 using lead connectors 26, which are fixed in a non-conductive header material 28, which can comprise an epoxy for example.

As shown in the cross-section of FIG. 1C, the IPG 10 typically includes a printed circuit board (PCB) 30, along with various electronic components 32 mounted to the PCB 30, some of which are discussed subsequently. Two antennas are shown in the IPG 10: a telemetry antenna 34 used to transmit/receive data to/from an external communication device (not shown); and a charging coil 36 for charging or recharging the IPG's battery 14 using an external charger (not shown). FIG. 1B shows these aspects in perspective with the case 12 removed for easier viewing. Charging coil 36 preferably comprises a coil, which receives power from an external charger by magnetic induction. Telemetry antenna 34 may also comprise a magnetic-induction coil, or may alternatively comprise a short range RF antenna for wirelessly communicating in accordance with a short-range RF standard such as Bluetooth, WiFi, MICS, Zigbee, etc., as described in U.S. Patent Application Publication 2016/0051825. Telemetry antenna 34 may be located within the case 12, or may be located within the header 28 in other examples.

FIG. 2 shows an architecture for the circuitry in IPG 10, which is disclosed in U.S. Patent Application Publications 2018/0071513 and 2018/0071520. The architecture includes at least one Application Specific Integrated Circuit (ASIC) 60. ASIC 60 includes a microcontroller block 50, which as shown in FIG. 2 can communicate with other functional blocks in the ASIC 60 via internal bus 92. Internal bus 92 can also connect to an external bus 90, and thus other control circuitry, or other circuitry more generally, on the IPG 10's PCB 30. In one example, the microcontroller block 50 can comprise circuitry from an ARM Cortex-M0+ Processor, which may be incorporated into the monolithic integrated circuit of the ASIC 60 by licensing various necessary circuits from the library that comprises that processor. ASIC 60 can comprise a monolithic integrated circuit formed on its own semiconductive substrate ("chip"), and may be contained in its own package and mounted to the IPG 10's PCB 30.

FIG. 2 shows various functional circuit blocks within ASIC 60 in addition to the microcontroller block 150, which are briefly described. As mentioned, ASIC 60 includes an internal bus 92, and each of the functional blocks includes interface circuitry 88 enabling communication on the internal bus 92. Interface circuitry 88 helps each block recognize when microcontroller block 50 is communicating addresses pertaining to that block via bus 92.

ASIC 60 contains several terminals 61 (e.g., pins, bond pads, solder bumps, etc.), such as those necessary to connect to the external bus 90, the battery 14, the antennas 34 and 36, external memory (not shown), etc. ASIC terminals 61 include electrode nodes 61a (E1'-E16' and Ec') which circuit nodes are also present on the PCB 30 (FIG. 1C) inside of the IPG's case 12. The electrode nodes 61a connect to the electrodes 16 (E1-E16) on the lead(s) 18 outside of the case 12 by way of DC-blocking capacitors 55. As is known, DC-blocking capacitors 55 are useful to ensure that DC current isn't inadvertently (e.g., in the event of failure of the ASIC 60's circuitry) injected into the patient's tissue, and hence provide safety to the IPG 10. Such DC-blocking capacitors 55 can be located on or in the IPG 10's PCB 30. See U.S. Patent Application Publication 2015/0157861. Note that there is also an electrode node 61a Ec' which is connected to the case 12 (preferably by a DC-blocking capacitor 55), thus allowing the case 12 to operate as an electrode 16 (Ec). ASIC 60 may support other numbers or types of electrode nodes/electrodes (e.g., thirty-two electrodes E1-E32 plus the case Ec).

Each of the circuit blocks in ASIC 60 performs various functions in IPG 10. Telemetry block 64 couples to the IPG telemetry antenna 34, and includes transceiver circuitry for wirelessly communicating with an external device according to a telemetry protocol. Such protocol may comprise Frequency Shift Keying (FSK), Amplitude Shift Keying (ASK), or various short-range RF standards such as those mentioned above. Charging/protection block 62 couples to the IPG charging coil 36, and contains circuitry for rectifying power wirelessly received at the charging coil 36 from an external charger (not shown), and for charging the battery 14 in a controlled fashion. See U.S. Patent Application Publication 2013/0023943.

Analog-to-Digital (A/D) block 66 digitizes various analog signals for interpretation by the IPG 10, such as the battery voltage Vbat, the compliance voltage VH (discussed in detail below), or voltages appearing at the electrodes, and is coupled to an analog bus 67 containing such voltages. A/D block 66 may further receive signals from a sample and hold block 68. See U.S. Pat. No. 9,061,140 (discussing sample and hold circuitry). For example, sample and hold circuitry 68 may determine a voltage difference between two electrode nodes, which voltage difference may then be digitized at A/D block 66. Knowing the difference in voltage between two electrodes when they pass a constant current allows for a determination of the (tissue) resistance between them, which is useful for a variety of reasons.

Clock generation block 74 can be used to generate a clock for the ASIC 60 and communication on the bus 92. Clock generation block 74 may receive an oscillating signal from an off-chip crystal oscillator 56, or may comprise other forms of clock circuitry located completely on chip, such as a ring oscillator. See U.S. Patent Application Publication 2014/0266375 (disclosing an on-chip circuit that can be used to generate a clock signal on the ASIC 60).

Nonvolatile memory (NOVO) block 78 caches any relevant data in the system (such as log data). Additional memory (not shown) can also be provided off-chip via a serial interface block 84, or can be connected to external bus 90.

ASIC 60 further includes a stimulation circuitry block 70, which includes circuitry for receiving and storing stimulation parameters from the microcontroller block 50 via bus 92. Stimulation parameters define the shape and timing of stimulation pulses to be formed at the electrodes, and can include parameters such as which electrodes E1-E16 or Ec will be active; whether those active electrodes are to act as anodes that source current to a patient's tissue, or cathodes that sink current from the tissue; and the amplitude (A), duration (D), and frequency (f) of the pulses. Amplitude may comprise a voltage or current amplitude. Such stimulation parameters may be stored in registers in the stimulation circuitry block 70. See, e.g., U.S. Patent Application Publications 2013/0289661; 2013/0184794.

Simulation circuitry block 70 also includes current generation circuitry such as Digital-to-Analog Converter (DAC) circuitry 72 for receiving the stimulation parameters from the registers and for forming the prescribed pulses at the selected electrodes. FIG. 3 shows a simple example of DAC circuitry 72 operating to provide current pulses between selected electrodes E1 and E2 and through a patient's tissue, Rt. A more complete description of DAC circuitry 72 is provided later, starting with FIG. 4A. DAC circuitry 72 as shown comprises two portions, denoted as PDAC and NDAC. These portions of DAC circuitry 72 are so named because of the polarity of the transistors used to build them and the polarity of the currents they provide. Thus, the PDAC is formed primarily from P-channel transistors and is used to source a current +I to the patient's tissue Rt via a selected electrode E1 operating as an anode. The NDAC is formed primarily from N-channel transistors and is used to sink current −I from the patient's tissue via a selected electrode E2. The current sourced to the tissue at any given time usually equals that sunk from the tissue to prevent charge from building in the tissue, although more than one anode electrode and more than one cathode electrode may be operable at a given time.

The PDAC and NDAC receive digital control signals from the registers in the stimulation circuitry block 70, generically denoted <Pstim> and <Nstim>, to generate the prescribed pulses with the prescribed timing and amplitude. In the example shown, the PDAC and NDAC comprise current sources, but could comprise voltage sources as well. A PDAC and NDAC pair may be dedicated at each of the electrodes, and thus may be activated only when its associated electrode is selected as an anode or cathode. See, e.g., U.S. Pat. No. 6,181,969. Alternatively, the current produced by one or more PDACs or NDACs may be distributed to selected electrodes by a switch matrix (not shown). Various examples of DAC circuitry 72 are disclosed in U.S. Pat. Nos. 6,181,969, 8,606,362, 8,620,436, and U.S. Patent Application Publications 2018/0071520 and 2019/0083796.

The PDAC and NDAC along with the intervening tissue Rt complete a circuit between a power supply VH, called the compliance voltage, and ground. The compliance voltage VH is preferably adjustable to an optimal level by a compliance voltage generator block 76 (FIG. 2) to ensure that current pulses of a prescribed amplitude can be produced without unnecessarily wasting IPG power. Such adjustment may occur by measuring voltage drops across the PDAC (Vp) and NDAC (Vn) circuitry as they are forming a pulse, as described further below. The measured voltage drops can be used to ensure that the compliance voltage VH produced is optimal for the stimulation current being provided—i.e., VH is not too low to be unable to produce the current required for the stimulation, nor too high so as to waste power in the IPG 10. Compliance voltage generator block 76 includes circuitry for boosting a power supply voltage such as the battery voltage, Vbat, to a proper level for VH. Such boost circuitry (some components of which may be located off chip) can include an inductor-based boost converter or a capacitor-based charge pump.

In the example waveform shown in FIG. 3, the pulses provided at the electrodes are biphasic, meaning that each pulse comprises a first phase 94a of a first polarity, followed by a second phase 94b of an opposite polarity. This is useful as a means of active recovery of charge that may build up on the DC-blocking capacitors 55. Thus, while charge will build up on the capacitors 55 during the first pulse phase 94a, the second pulse phase 94b will actively recover that charge, particularly if the total amount of charge is equal in each phase (i.e., if the area under the first and second pulse phases are equal). Recovery of excess charge on the DC-blocking capacitors 55 is desirable to ensure that the DAC circuitry 72 will operate as intended: if the charge across the DC-blocking capacitors 55 is not zero at the end of each pulse, such remaining charge may impact formation of subsequent pulses, or other problems may occur, as discussed further below.

While active recovery of charge using a biphasic pulse is beneficial, such active recovery may not be perfect, and hence some residual charge may remain on the DC-blocking capacitors 55 (or other capacitances in the current path) even after completion of the second phase 94b of the biphasic pulse. Passive charge recovery may therefore be employed that does not involve use of active currents driven by the DAC circuitry 72. Passive charge recovery is implemented within the stimulation circuitry block 70, and includes use of passive recovery switches (e.g., transistors) 96(x), each connected between one of the electrode nodes (Ex' and Ec') 61a and a common reference voltage. This common reference voltage as shown may comprise the voltage, Vbat, of the battery 14 as (FIG. 1C) as shown, but another reference voltage could also be used. A variable resistor 97 can be connected in series to each of the passive recovery switches 96 between the electrodes nodes 61a and the common reference voltage (e.g., Vbat) to set the rate of passive discharge during periods 98. See U.S. Patent Application Publication 2018/0071527 (discussing passive charge recovery).

SUMMARY

A method is disclosed for programming a stimulator device, the stimulator device comprising a plurality of electrodes and current generation circuitry configured to provide pulses at selected ones of the electrodes, wherein the current generation circuitry is powered by a time-varying compliance voltage produced at an output of a compliance voltage generator. The method may comprise: receiving information defining a waveform comprising a sequence of pulses; determining a plurality of groups of one or more contiguous pulses in the waveform; associating each group with a compliance voltage variable; and determining programming instructions configured to: program the current generation circuitry to produce the groups thereby producing the waveform at the selected ones of the electrodes, and program the compliance voltage generator to produce the time-varying compliance voltage at the output, wherein the compliance voltage generator is programmed with the compliance voltage variable associated with the group being produced by the current generation circuitry.

In one example, the method further comprises determining a compliance voltage value for each compliance voltage variable. In one example, the compliance voltage values are determined by taking measurements in the stimulator device. In one example, each compliance voltage value is determined to be suitable to produce the pulses in their associated group at prescribed amplitudes. In one example, each compliance voltage value is further determined to preserve power in the stimulator device. In one example, the method further comprises use of an external device in communication with the stimulator device, wherein the information defining the waveform is received at the external device, wherein each group is associated with a compliance voltage variable at the external device, and wherein the programming instructions are determined at the external device; and further comprising transmitting the programming instructions from the external device to the stimulator device. In one example, the method further comprising determining a compliance voltage value for each compliance voltage variable at the external device, wherein the programming instructions are configured to program the compliance voltage generator with the compliance voltage values to produce the time-varying compliance voltage at the output, wherein the compliance voltage generator is programmed with the compliance voltage value associated with the group being produced by the current generation circuitry. In one example, the method further comprises determining a compliance voltage value for each compliance voltage variable at the stimulator device, and transmitting the determined compliance voltages values to the external device. In one example, the programming instructions are configured to program the compliance voltage generator with the compliance voltage values to produce the time-varying compliance voltage at the output, wherein the compliance voltage generator is programmed with the compliance voltage value associated with the group being produced by the current generation circuitry. In one example, the compliance voltage values are determined by taking measurements in the stimulator device. In one example, the programming instructions are further configured to cause the stimulator device to determine a compliance voltage value for each compliance voltage variable. In one example, the compliance voltage values are determined by taking measurements in the stimulator device. In one example, the information defining the waveform is received at the stimulator device; and wherein each group is associated with a compliance voltage variable at the stimulator device, and wherein the programming instructions are determined at the stimulator device. In one example, the method comprises determining a compliance voltage value for each compliance voltage variable at the stimulator device. In one example, the compliance voltage values are determined by taking measurements in the stimulator device. In one example, the plurality of groups are automatically determined using a computer-implementable algorithm. In one example, the computer-implementable algorithm is configured to automatically determine the one or more contiguous pulses in each group by applying one or more rules that identify that at least some of the one or more contiguous pulses have similar compliance voltage requirements. In one example, the one or more rules identify that the one or more contiguous pulses have amplitudes that are within a specified range. In one example, the one or more rules identify that the one or more contiguous pulses have energies that are within a specified range. In one example, the method further comprises use of an external device in communication with the stimulator device, wherein at least one of the plurality of groups is determined at least in part based on input received from a user at the external device. In one example, the pulses within one or more of the groups have amplitudes, pulse widths, energies, or shapes that are different. In one example, a first of the groups is produced during a time period comprising a first time period followed by a second time period, wherein the compliance voltage generator is programmed with a first of the compliance voltage variables during the first group. In one example, the first compliance voltage variable is higher than a preceding compliance voltage variable, wherein the time-varying compliance voltage rises over the first time period, and wherein the time-varying compliance voltage equals the first compliance voltage variable during the second time period. In one example, an amplitude, pulse width, or energy of the pulses in the first group is smaller during the first time period than during the second time period. In one example, the first compliance voltage variable is lower than a preceding compliance voltage variable, wherein the time-varying compliance voltage falls over the first time period, and wherein the time-varying compliance voltage equals the first determined compliance voltage during the second time period. In one example, an amplitude or energy of the pulses in the first group is constant during the first and second time periods. In one example, the time-varying compliance voltage rises or falls over time periods when the compliance voltage variables to which the compliance voltage generator is programmed change. In one example, the time periods are used to determine the plurality of groups. In one example, the compliance voltage variables are determined such that the time-varying compliance voltage is always high enough to form the sequence of pulses in the waveform at prescribed amplitudes. In one example, the compliance voltage variables are also determined to minimize the time-varying compliance voltage to preserve power in the stimulator device. In one example, the information defining the waveform comprises a plurality of blocks of the pulses in the sequence, wherein each of the blocks comprise pulses of the same amplitude, pulse width, energy, or shape. In one example, the programming instructions are further configured to program the stimulator device to make measurements to assess the time-varying compliance voltage at different points in time. In one example, the stimulator device is configured to adjust values of the compliance voltage variables using the measurements. In one example, if the measurements indicate during production of a particular group that the time-varying compliance voltage is too low, the stimulator device is configured to adjust the compliance voltage variable associated with that group to a higher value. In one example, if the measurements indicate during production of a particular group that the time-varying compliance voltage is too high, the stimulator device is configured to adjust the compliance voltage variable associated with that group to a lower value.

A method is disclosed for programming a stimulator device, the stimulator device comprising a plurality of electrodes and current generation circuitry configured to provide pulses at selected ones of the electrodes, wherein the current generation circuitry is powered by a time-varying compliance voltage produced at an output of a compliance voltage generator. The method may comprise: receiving information defining a waveform comprising a sequence of pulses; determining a plurality of transitions in the waveform comprising one or more first transitions where the pulses increase in amplitude or energy; determining a time period before each of the first transitions; and determining programming instructions configured to: program the current generation circuitry to produce the waveform at the selected ones of the electrodes, and program the compliance voltage generator to produce the time-varying compliance voltage at the output, wherein the compliance voltage generator is programmed at first times to increase the time-varying compliance voltage at the time periods before each of the one or more first transitions.

In one example, the time period before each transition is determined to allow the time-varying compliance voltage to increase such that compliance voltage will be at a value suitable to form pulses after the first transitions at prescribed amplitudes. In one example, the time period before each transition is determined by determining a rise time at the output of the compliance voltage generator at each first transition. In one example, the rise times are measured at each first transition. In one example, the programming instructions are further configured to program the stimulator device to make measurements to assess the time-varying compliance voltage. In one example, the measurements are made during at least one of the pulses after each of the first transitions. In one example, the stimulator device is configured to adjust programming of the compliance voltage generator using the measurements. In one example, if the stimulator device determines during a given measurement associated with one of the first transitions that the time-varying compliance voltage is too low, or too high, the compliance voltage generator is programmed to respectively further increase, or lower while still increasing, the time-varying compliance voltage at the first time before that first transition. In one example, the compliance voltage generator is programmed at the first times with values, and wherein if the stimulator device determines during a given measurement associated with one of the first transitions that the time-varying compliance voltage is too low, or too high, the compliance voltage generator is programmed to respectively increase, or decrease, the value at the first time before that first transition. In one example, the plurality of transitions further comprise one or more second transitions in the waveform where the pulses decrease in amplitude or energy, and wherein the programming instructions are further configured to program the compliance voltage generator at second times to decrease the compliance voltage at the one or more second transitions. In one example, the method further comprises determining a compliance voltage for each of a group of contiguous ones of the pulses in the waveform, wherein each group comprises pulses between one of the first times and a next second time, or one of the second times and a next first time. In one example, the compliance voltage generator is programmed with the determined compliance voltage associated with the group of pulses being produced by the current generation circuitry. In one example, each compliance voltage is determined to be suitable to produce the pulses in its associated group of pulses at prescribed amplitudes. In one example, each compliance voltage is further determined to preserve power in the stimulator device. In one example, the method further comprises use of an external device in communication with the stimulator device, wherein each compliance voltage is determined at the external device. In one example, at least one of the compliance voltages is determined based on input received from a user at the external device. In one example, each compliance voltage is determined using compliance voltage measurements taken at the stimulator device, and further comprising transmitting the determined compliance voltages to the external device. In one example, each compliance voltage is determined at the stimulator device. In one example, the method further comprises use of an external device in communication with the stimulator device, wherein the information defining the waveform is received at the external device; wherein the plurality of transitions in the waveform are determined at the external device; wherein the time periods before each of the first transitions are determined at the external device; and wherein the programming instructions are provided from the external device to the stimulator device. In one example, the information defining the waveform is received at the stimulator device; wherein the plurality of transitions in the waveform are determined at the stimulator device; and wherein the time periods before each of the first transitions are determined at the stimulator device. In one example, the information defining the waveform comprises a plurality of blocks of the pulses in the sequence, wherein each of the blocks comprise pulses of the same amplitude, pulse width, energy, or shape.

A method is disclosed for programming a stimulator device, the stimulator device comprising a plurality of electrodes and current generation circuitry configured to provide pulses at selected ones of the electrodes, wherein the current generation circuitry is powered by a compliance voltage produced at an output of a compliance voltage generator. The method may comprise: receiving information defining a waveform comprising a sequence of pulses, each of the pulses formed in accordance with stimulation parameters; determining at least one group of one or more contiguous pulses in the waveform, wherein the at least one group comprises a plurality of contiguous blocks of pulses, wherein the stimulation parameters vary between each of blocks, wherein each at least one group is associated with a compliance voltage variable; executing a computer-implementable algorithm to automatically determine one or more first of the plurality of contiguous blocks in each at least one group that will be used to determine the compliance voltage variable for each group; and automatically determining programming instructions configured to: program the current generation circuitry to produce the at least one group thereby producing the waveform at the selected ones of the electrodes, program the compliance voltage generator with the compliance voltage variable associated with the at least one group being produced by the current generation circuitry, and cause the stimulation device to make measurements to assess the compliance voltage during at least one pulse in each of the one or more first blocks in each group.

In one example, the pulses in each group are each provided to a first of the plurality of electrodes. In one example, the pulses in each group are each provided to the first electrodes with a same polarity and a same amplitude percentage. In one example, the method further comprises determining a compliance voltage value for each compliance voltage variable using the measurements. In one example, each compliance voltage value is determined to be suitable to produce the pulses in their associated group at prescribed amplitudes. In one example, each compliance voltage value is further determined to preserve power in the stimulator device. In one example, if the measurements indicate during production of one of the at least one groups that the compliance voltage is too low, the stimulator device is configured to adjust the compliance voltage variable associated with that group to a higher value. In one example, if the measurements indicate during production of one of the at least one groups that the compliance voltage is too high, the stimulator device is configured to adjust the compliance voltage variable associated with that group to a lower value. In one example, the method further comprises use of an external device in communication with the stimulator device, wherein the information defining the waveform is received at the external device, wherein each at least one group is determined at the external device, wherein the computer-implementable algorithm is executed at the external device, and wherein the programming instructions are determined at the external device; and further comprising transmitting the programming instructions from the external device to the stimulator device. In one example, the method further comprises determining a compliance voltage value for each compliance voltage variable at the external device, wherein the programming instructions are configured to program the compliance voltage generator with the compliance voltage values to produce the compliance voltage at the output. In one example, the method further comprises determining a compliance voltage value for each compliance voltage variable at the stimulator device using the measurements, and transmitting the determined compliance voltages values to the external device. In one example, the programming instructions are configured to program the compliance voltage generator with the compliance voltage values to produce the compliance voltage at the output, wherein the compliance voltage generator is programmed with the compliance voltage value associated with the at least one group being produced by the current generation circuitry. In one example, at least one of the at least one groups is determined at least in part based on input received from a user at the external device. In one example, the information defining the waveform is received at the stimulator device, wherein each at least one group is determined at the stimulator device, wherein the computer-implementable algorithm is executed at the stimulator device, and wherein the programming instructions are determined at the external device. In one example, the method further comprises determining a compliance voltage value for each compliance voltage variable at the stimulator device using the measurements. In one example, the computer-implementable algorithm is used to determine the at least one group of one or more contiguous pulses in the waveform. In one example, the one or more first blocks in each at least one group comprise the blocks with the highest-energy pulses in that group. In one example, the one or more first blocks in each at least one group comprise the blocks with the highest-amplitude pulses in that group. In one example, the one or more first blocks in each at least one group comprise the blocks with the highest-pulse width pulses in that group. In one example, the one or more first blocks in each at least one group comprise a block with the highest-amplitude pulses in that group and a block with the highest-pulse width pulses in that group. In one example, the one or more first blocks in each at least one group comprise a block with pulses having a first amplitude and a first pulse width, and a block with pulses having a first amplitude and a first pulse width, wherein the first amplitude is higher than the second amplitude, and wherein the first pulse width is lower than the second pulse width. In one example, the one or more first blocks in each at least one group comprise a block applied to a first of the plurality of electrodes, and a block applied to a second the plurality of electrodes. In one example, the programming instructions are configured to cause the stimulation device to make measurements to assess the compliance voltage during at least a first pulse in each of the one or more first blocks in each group.

BRIEF DESCRIPTION OF THE DRAWINGS

FIG. 6 shows external devices useable to program the IPG, and which may execute a compliance voltage (VH) management algorithm.

FIGS. 7A-7D show examples of a graphical user interface (GUI) that can be executed on an external device to allow a user to form a complex waveform using different blocks of pulses, and shows the compilation of programming instructions for the IPG necessary to form the waveform at the IPG, including the compilation of aggregate, steering, and pulses programs.

FIGS. 8A and 8B show how a compliance measurement instruction (e.g., a CMB) can be included in the IPG's programming instructions, and further shows measurement circuitry responsive to the instruction, which culminates in determining a value VH(opt) used to program a compliance voltage generator that set a value for the compliance voltage VH received by the DAC circuitry.

FIGS. 9A and 9B show circuitry for the compliance voltage generator, which in this example comprises a capacitor-based charge pump.

FIG. 11B shows a table defining relevant aspects of the waveform, which table can be adjusted in subsequent steps of a VH management algorithm.

FIGS. 12A-12C show an example of the VH management algorithm operable in either an external device or in the IPG, to analyze the waveform and determine when the compliance voltage should be adjusted and to what values.

FIGS. 13A-13D show steps in the algorithm for determining groups of pulses in the waveform, where pulses in such groups will be treated similarly by the algorithm for compliance voltage management purposes.

FIG. 14A shows steps in the algorithm for determining optimal compliance voltages VH(opt) for each of the determined groups, while

FIGS. 15A-15C show steps in the algorithm for identifying groups for which compliance voltage management is not practical, and thus consolidating such identified groups into preceding or following groups.

FIGS. 16A and 16B show iterative application of the VH management algorithm, which can lead to still further consolation of the previously-determined groups.

FIGS. 17A-17D shows steps in the algorithm where the rise times determined earlier are considered, which allows VH adjustment instructions to be provided early in time so that VH has time to ramp to a proper higher value.

FIGS. 20A-20E shows how the algorithm can include compliance voltage measurement instructions in the IPG's programming instructions as useful to updating the determined optimal values for VH.

FIGS. 21A-21C show how the algorithm can compile or enable use of a VH adjust algorithm in the IPG that is able to consider appropriate compliance voltage measurements as useful to updating the determined optimal values for VH.

FIG. 22 shows that compliance voltage measurements can be used to determine optimal values for VH, and therefore such values do not need to be specifically determined by the algorithm in advance of waveform execution in the IPG.

DETAILED DESCRIPTION

Before discussing compliance voltage monitoring and adjustment in an IPG system, which are the focus of this disclosure, further details concerning the stimulation circuitry 70 and the current generation circuitry 72 in an IPG are discussed. This is done for completeness, and to show an example implementation in which the compliance voltage management aspects of this disclosure can operate. Note however that implementations of the invention are not limited to the use of any particular stimulation circuitry 70 or current generation circuitry 72.

Figure 4A:
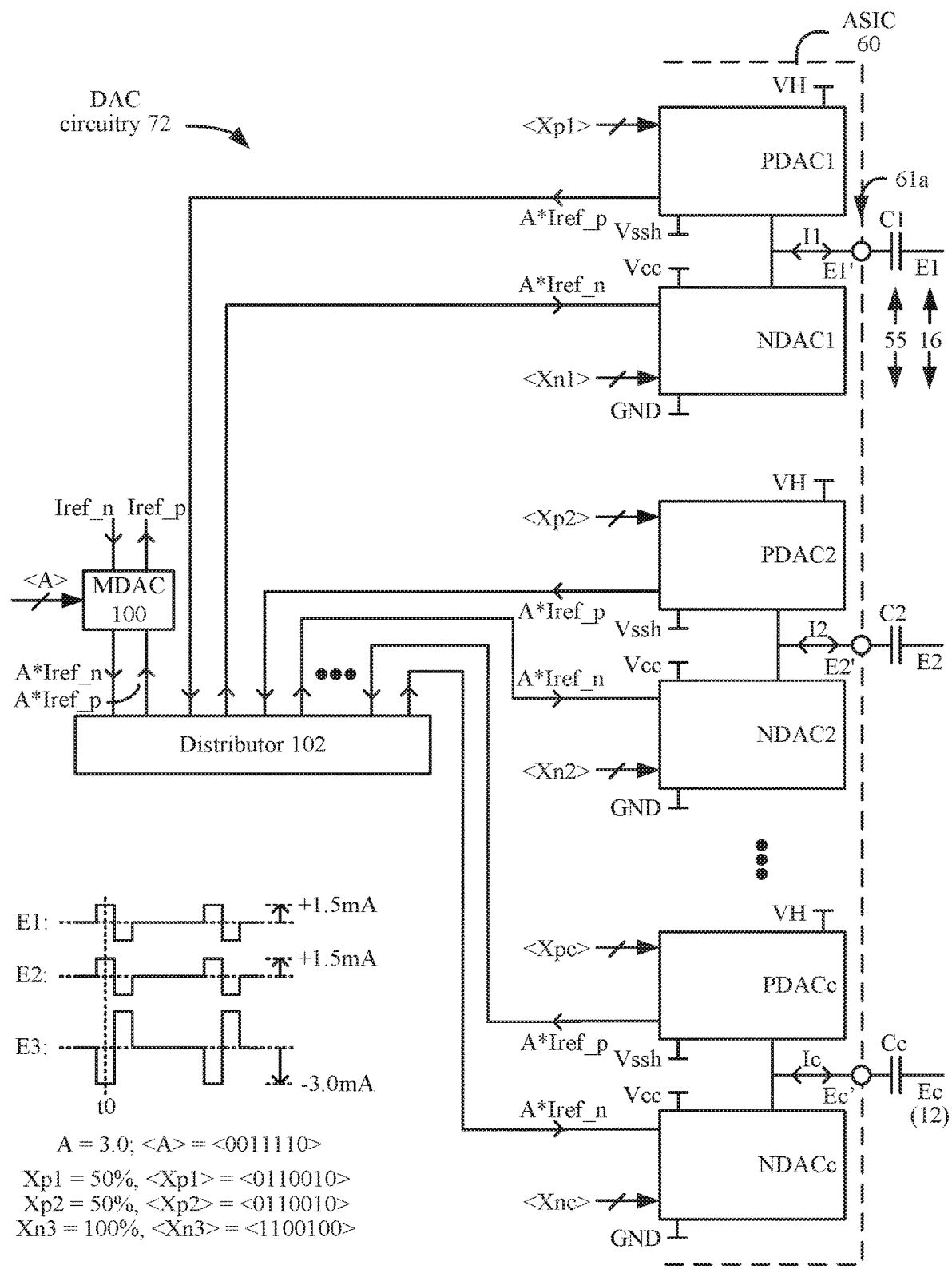
FIGS. 4A-4C show further details of the stimulation circuitry and DAC circuitry.

FIG. 4A shows a simplified version of the current generation circuitry, which may comprise DAC circuitry 72 disclosed in U.S. Patent Application Publication 2019/0083796, with which the reader is assumed familiar. Again, other DAC circuitries such as those mentioned in the Introduction could be used as well. In the example of FIG. 4A, an amplitude A, as reflected in digital control signals <A>, is provided to a master DAC (MDAC) 100. Amplitude A may be specific to a particular timing channel operating in the IPG, as explained further below, and may be indicative of a total anodic and cathodic amplitude to be sourced and sunk during that timing channel at any given time. MDAC 100 receives reference currents Iref_p and Iref_n which are preferably of equal magnitude, but of opposite polarities. The MDAC 100 amplifies these reference currents to provide currents A*Iref_p and A*Iref_n, also of opposite polarities.

Distributor circuitry 102 provides A*Iref_p to various PDACs (PDAC1, PDAC2, etc.), and provides A*Iref_n to various NDACs (NDAC1, NDAC2, etc.). In the example shown, a PDAC/NDAC pair is dedicated to each electrode node. Thus, PDAC1 or NDAC1 can be enabled to source or sink a current I1 to electrode node E1', which is coupled to electrode E1 (e.g., on a lead) via a DC-blocking capacitor C1. PDAC2 and NDAC2 can likewise be enabled to source or sink a current I2 to electrode node E2' and electrode E2 via its DC-blocking capacitor C2. As noted earlier, the conductive case 12 can also operate as an electrode Ec, and thus PDACc and NDACc can likewise be enabled to source or sink a current Ic to electrode node Ec' and to case electrode Ec 12 via DC-blocking capacitor Cc. As mentioned above, DAC circuitry 72 could in other examples use PDACs and NDACs that are not dedicated to particular electrode nodes/electrodes as shown. For example, switching matrices (not shown), could be used to connect the outputs of the PDAC/NDAC pairs to any one of the electrode nodes Ex'.

Also received by each PDAC and each NDAC are digital control signals <X> that inform as to the percentage of the total anodic and cathodic amplitude A that each PDAC or NDAC should produce. Thus, PDAC1 receives percentage control signals <Xp1>, NDAC1 receives <Xn1>, PDAC2 receives <Xp2>, and so forth. The waveforms at the bottom of FIG. 4A show an example at time t0 where an anodic pulse of amplitude +1.5 mA is formed at E1 and E2, and a cathodic pulse of amplitude −3.0 mA is formed at E3, and shows examples of the digital control signals that are used to form these pulses. In this example, the total anodic and cathodic current is 3.0 mA, and <A> is thus digitally set to indicate this value; for example, and assuming <A> increments in 0.1 mA steps, <A> can be set at time t0 to 30, or 0011110 in binary. Electrodes E1 and E2 split the anodic current equally, and so Xp1 and Xp2 are set at time t0 to 50%, or 0110010 in binary. Electrode E3 receives all of cathodic current, and so Xn3 is set at time t0 to 100%, or 1100100 in binary. All other percentage control signals (Xn1, Xn2, Xp3, Xn4, Xp4, etc.) would be set to 0% (0000000), indicating that corresponding NDACs and PDACs would not be producing a current at time to.

Figure 3:
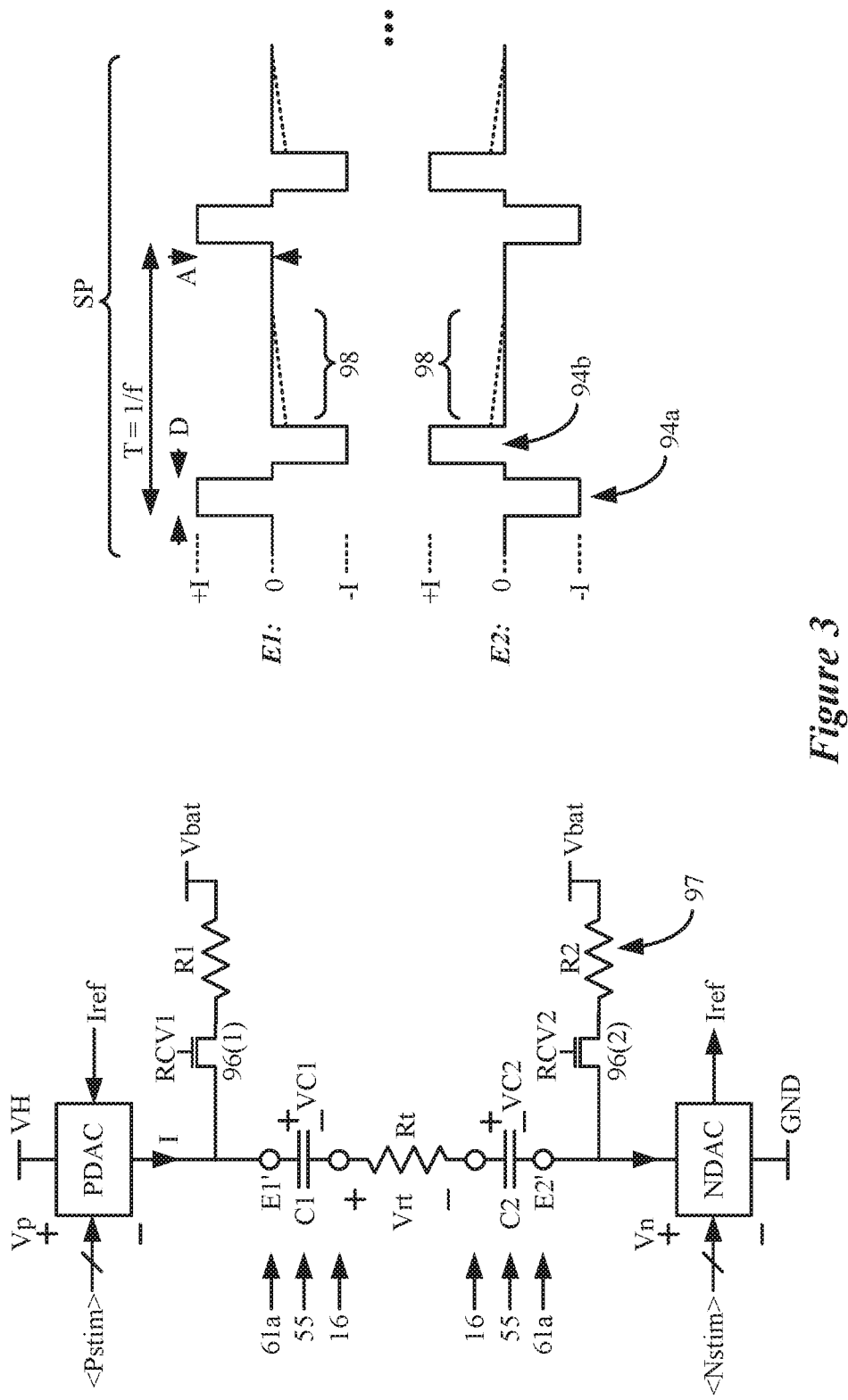
FIG. 3 shows aspects of the Digital-to-Analog Converters (DACs) within the stimulation circuitry of the ASIC, and stimulation pulses formable thereby.
Figure 4B:
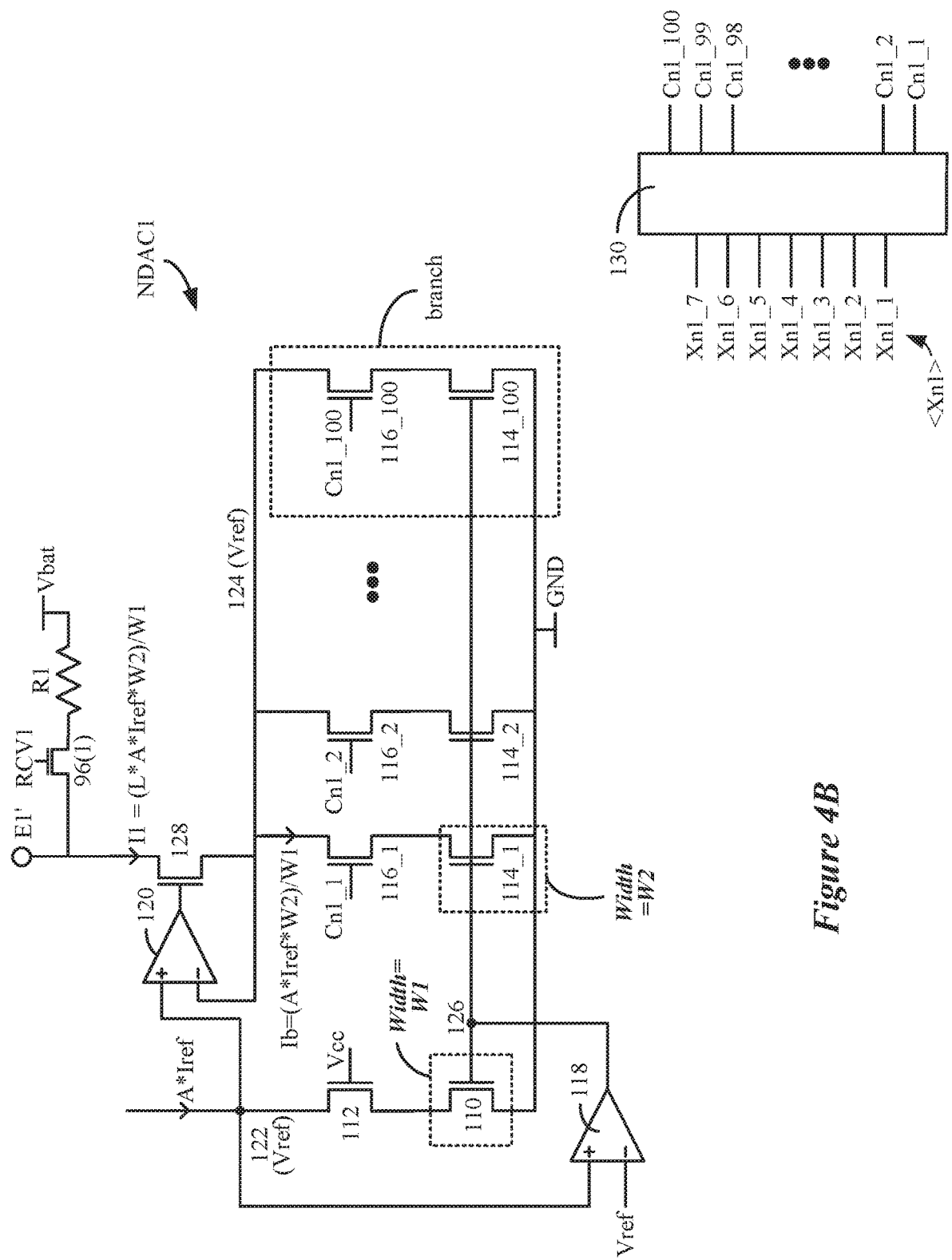

FIG. 4B shows an example of the circuitry of an NDAC (e.g., NDAC1) for providing a cathodic current at an electrode node (e.g., E1'). Other NDACs would be similar. The PDACs, as shown in the '796 Publication, also have similar circuitry, although of opposite polarity due to the anodic currents the PDACs produce. Also shown in FIG. 4B is the passive charge recovery switch 96(1) connected to electrode node E1', which was explained earlier with respect to FIG. 3.

Amplified reference current A*Iref_n (shortened to A*Iref in FIG. 4B) is provided from the distributor 102 to one or more resistance transistors 110 through an always-on switch 112. The NDAC also includes a number of branches (e.g., 100 branches), with each branch having a branch transistor 114_x connected in series to a switch 116_x. As explained in the '796 Publication, using op amps 118 and 120, a reference voltage Vref is maintained across the resistance transistor(s) 110 (at node 122) and each of the branches (at node 124). The resistance of switches 112 and 116_x are negligible, and so Vref is effectively dropped across the resistance transistor(s) 110 and each of the branch transistors 114_x.

Resistance transistor(s) 110 and branch transistors 114_x are not connected in a current mirror configuration, but are on to the same degree due to their common gate connection at node 126. These transistors 110 and 114 are preferably of different widths W1 and W2, with W2 larger than W1, meaning that the resistance of the branch transistors 114 are W2/W1 less than the resistance of the resistance transistor(s) 110. This resistance difference, coupled with the common voltage drop Vref across each, sets the current in each branch, again as explained in detail in the '796 Publication. Resistance transistor(s) 110 receive A*Iref, while each branch x, when selected by its switch 116_x, provides an amplified current of Ib=(A*Iref*W2)/W1. If L=3 branches are selected, for example by turning on switches 116_1, 116_2, and 116_3 via switch control signals Cn1_1, Cn1_2, and Cn1_3, a total current of I1=(3*A*Iref*W2)/W1 is provided to the electrode node E1', and ultimately to electrode E1 via an output transistor 128.

The switch control signals Cn1_x are derived from the percentage control signals <Xn1> via logic circuitry 130. Such logic circuitry 130 is shown only generically in FIG. 4B, but the '796 Publication explains it in more detail. Essentially, logic circuitry 130 acts as a decoder to assert a number of switch control signals Cn1_x in proportion to the percentage reflected in percentage control signals. For example, if the percentage control signals <Xn1>=30 ('001110'), then logic circuitry may assert Cn1_1 through Cn1_30 (or any thirty of the switch control signals). This turns on switch transistors 116_1 through 116_30, which sets the current I1 (i.e., I1=30*Ib=(30*A*Iref*W2)/W1) at electrode node E1'. Note that this conversion of percentage control signals into switch control signals occurs in each of the PDACs and NDACs. Thus, percentage control signals <Xp1> provided to PDAC1 are converted into switch control signals Cp1_x; percentage control signals <Xn2> provided to NDAC2 are converted into switch control signals Cn2_x, and so on.

Figure 4C:
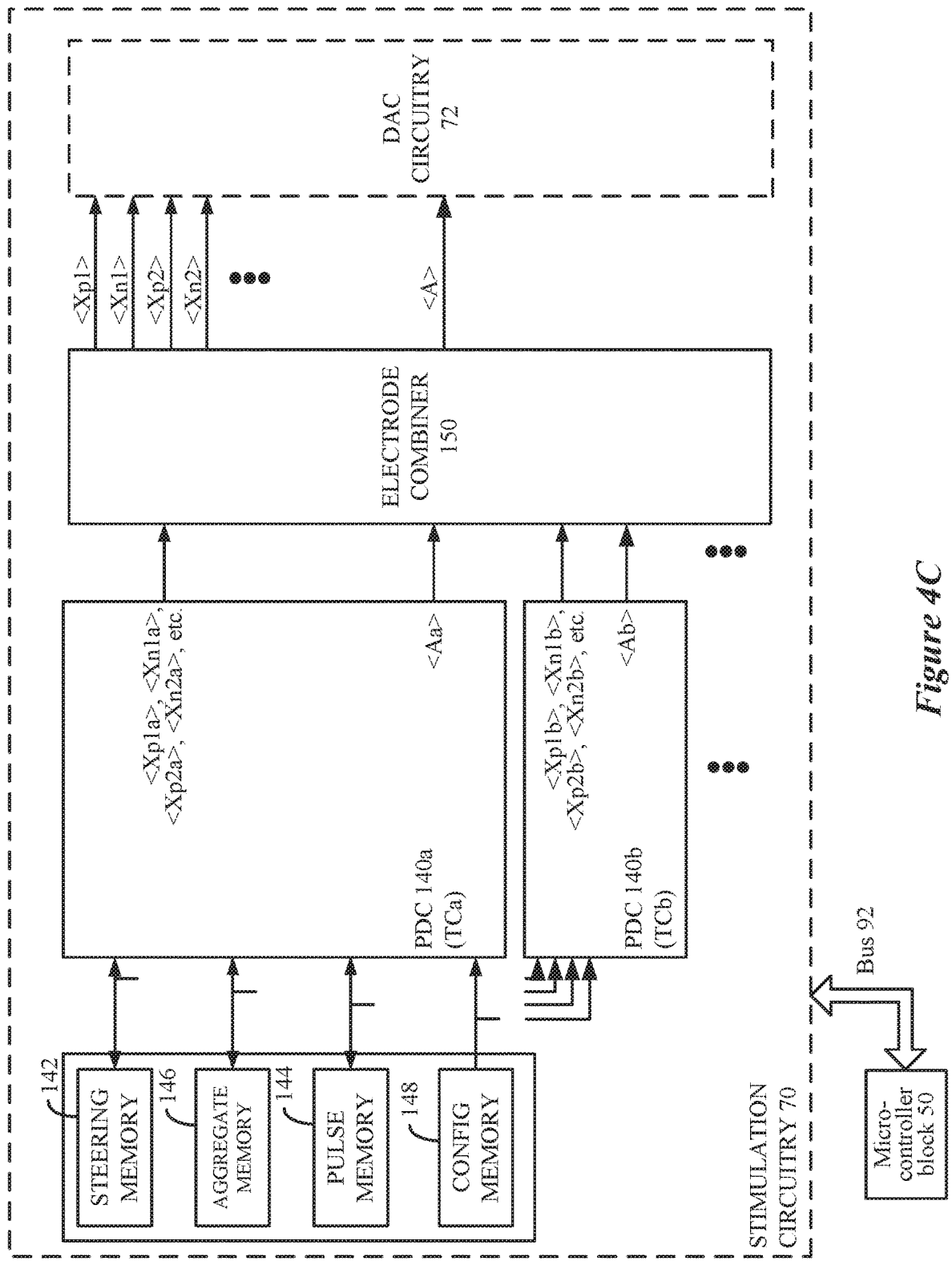

Stimulation circuitry 70 as shown in FIG. 4C shows further details of how relevant control signals such as <A> and <X> arrive at the DAC circuitry 72. The stimulation circuitry 70 includes memory circuitry that stores microcode processed by one or more pulse definition circuits (PDCs) 140. Memory circuitry includes a steering memory 142 that contains electrode steering programs, and a pulse memory 144 that contains pulse programs, both of which are discussed further with respect to FIG. 5B. Memory circuitry also includes an aggregate memory 146 that contains aggregate programs that link or associate one or more pulse programs and one or more steering programs to create a desired stimulation pulse therapy program, as discussed further with respect to FIG. 5C. The stimulation circuitry 70 additionally includes a configuration memory 148 that stores configuration parameters, some of which are global and applied across all PDCs 140, and some of which are specific to a particular PDC 140. The memories 142-148 can be read from and written to by the microcontroller 50 via bus 92. Each location (e.g., each 32-bit location) in the memory circuitry may be formed as a register of multiple flip-flops or as an addressable location in a more typical memory, and may comprise separate memory circuits or a single memory circuit.

In one example, there may be four PDCs, although only two (140a and 140b) are shown in FIG. 4C. Each of the PDCs are used in a normal mode to control the formation of stimulation pulses within a timing channel, such as TCa and TCb. Each timing channel allows pulses to be formed independently and concurrently, thus allowing more complex stimulation patterns to be provided to patients. The total anodic and cathodic current amplitude provided by PDC 140a in TCa is Aa, which amplitude is specified in a given pulse program, as explained shortly. By contrast, the total anodic and cathodic current amplitude provided by PDC 140b in TCb may be different, i.e., Ab. Because the pulses from the different timing channels may overlap in time, an electrode combiner 150 is used to reconcile information concerning what the total anodic and cathodic current amplitude A, and what percentage control switches <X> (and hence which switches 116 in the DACs), should be asserted at any given time. In this regard, the electrode combiner 150 can receive amplitude and percentage information from each PDC 140 (e.g., <Aa>, and <Xp1a>, <Xn1a>, <Xp2a>, etc. from PDC 140a, and <Ab>, and <Xp1b>, <Xn1b>, <Xp2b>, etc. from PDC 140b) to derive a single amplitude <A> and a single set of percentage control switches <Xp1>, <Xn1>, <Xp2>, etc., to be used by the DAC circuitry 72 at any given time.

Figure 5A:
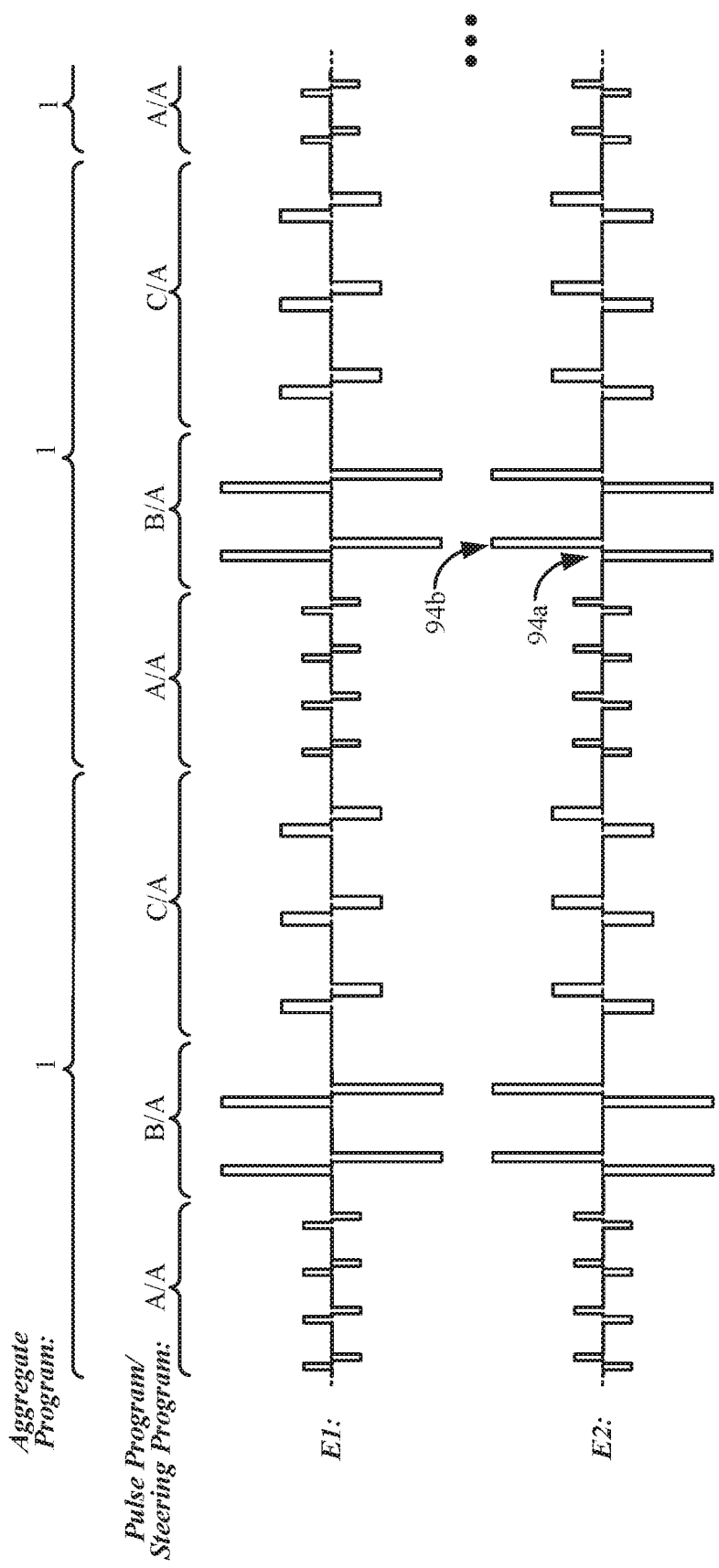
FIG. 5A shows a waveform issued according to an aggregate program (FIG. 5C) that references a pulse program and a steering program (FIG. 5B).
Figure 5B:
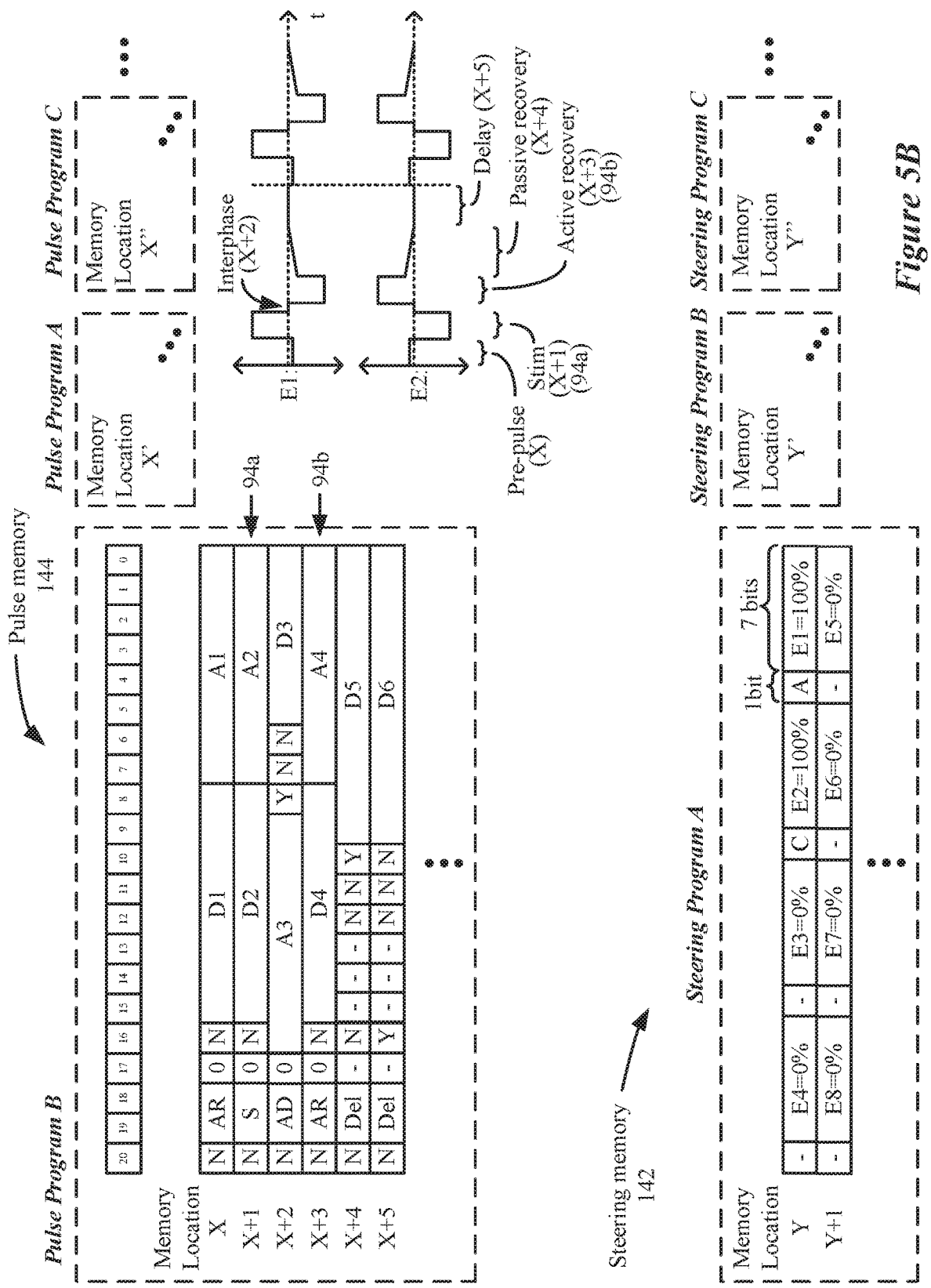

The unique configuration of the stimulation circuitry 70 and DAC circuitry 72 allows for the efficient production of stimulation waveforms of unique and varying shapes. FIG. 5A shows an example of a waveform that can be produced in a particular timing channel (e.g., TCa, using PDAC 140a). In this example, two electrodes E1 and E2 have been selected for stimulation, which occurs by selection of a particular steering program A in steering memory 142, as shown in FIG. 5B. A steering program generally informs as to which electrodes are to receive pulses, the polarity of the pulses at those electrodes, and a percentage of the total anodic and cathodic amplitude for the pulses at those electrodes. Steering program A may be stored starting at memory location Y, with each location storing data for four of the electrodes (e.g., electrode E1-E4). One quarter of each location (8 bits) stores the data for a particular electrode, including a bit indicating whether the electrode is to comprise an anode ('1') or cathode ('0'), and up to seven bits indicating a percentage of the anodic or cathodic current that that electrode is to receive (<X>). Pursuant to the example of FIG. 5A, notice in FIG. 5B that memory location Y specifies that electrode E1 has been designated an anode (A='1'), which receives 100% of the total anodic current (i.e., <Xp1>=100%), and electrode E2 has been designated an anode (C='0'), which receives 100% of the total cathodic current (i.e., <Xn2>=100%). (As explained below, the associated pulse program includes information which reverses these polarities at appropriate times for a biphasic pulse). Electrodes E3 and E4, which are not used in this example, receive 0% of the total current, making their polarities irrelevant, and the same would be true for the remaining electrodes in subsequent memory locations (e.g., next memory location Y+1 storing data for electrodes E5-E8 would also have 0%, etc.).

Multiple steering programs can be stored in steering memory 142 (e.g., steering program B starting at memory location Y'; steering program C starting at memory location Y"), each designating different one or more electrodes to operate as anodes and one or more electrodes to operate as cathodes, and a percentage of the total anodic and cathodic current such electrodes will receive. Note that the percentages for the anode electrodes in a given a steering program would normally sum to 100%, and the percentages for the cathode electrodes in that steering program would normally sum to 100%, thus ensuring that the same total anodic current (+A) and the total cathodic current (−A) is prescribed at any given time, which prevents a net injection of charge into the patient's tissue.

Also shown in FIG. 5B are a number of pulse programs stored in pulse memory 144. Pulse programs specify the basic shape of a pulse, including an amplitude (A) and duration (D) of its various phases. Example pulse program B is shown as starting at memory location X, with each successive location including data for a successive phase in the pulse. Only 20 of the 32 available bits may be used at each location to define the pulse phases. Bits 19 and 18 specify a type of pulse phase, which dictates the format of the remaining bits in that memory location. For example, pulse phase types may comprise active stimulation phases, delay phases which don't involve active generation of currents, and passive charge recovery phases dictating when passive charge recovery switches (96(x), FIG. 3) should be closed. The reader can refer to the above-incorporated '513 Publication for a more complete discussion of the types of pulse phases and the various bits that are stored with each.

In the example of FIG. 5B, pulse program B defines a biphasic pulse having six phases, as shown in FIG. 5B's waveform. The first phase (memory location X) comprises an actively-driven pre-pulse phase, which may be of low amplitude A1 and a short duration D1. It is designated as an active-driven recovery phase (AR), which operates to flip the polarity of the electrodes otherwise specified by the steering program. Thus, assuming pulse program B is associated with steering program A, E1 would comprise a cathode and E2 an anode during this pulse phase, as shown in the waveforms. The second phase (location X+1) comprises an actively-driven stimulation phase (S) of amplitude A2 and duration D2, and generally corresponds to the first pulse phase 94a described earlier (FIG. 3). The polarities are not flipped for this pulse phase type, and so E1 would comprise an anode and E2 a cathode during this pulse phase. The third phase (location X+2) comprises an interphase, amounting to a delay between the first and second pulses phases 94a and 94b. This interphase is designated as "AD," meaning an active delay, which keeps the DAC circuitry 72 powered in preparation for driving a subsequent stimulation or active recovery phase. During this interphase, the amplitude A3 would normally be set to zero, and the interphase would generally have a short duration D3. The fourth phase (location X+3) comprises an active recovery phase (AR), and generally corresponds to second pulse phase 94b (FIG. 3). This phase will actively recover charge injected primarily during the stimulation phase, and therefore will have a significant amplitude A4 and/or duration D4. Again, the polarity of the electrodes specified by the steering program will flip during this phase. The fifth phase (location X+4) comprises a delay phase ("Del"), and because a passive recovery bit (bit 10) is set, passive recovery will occur during duration D5 by closing relevant ones of the passive charge recovery switches (96(x), FIG. 3). The sixth phase (location X+5) also comprises a delay phase of duration D6, but without passive charge recovery. This phase essentially comprises a dead period that will occur before the next pulse—i.e., the first phase of the next pulse. Note as consistent with their function, delay phase types do require specifying an amplitude, because the DAC circuitry 72 does not actively drive a current during these phase types. Bit 16 is set to inform that this is the last phase in the pulse.

Note that the sum total of the phase durations (D1, D2, etc.) defines a pulse period (T), which determines the frequency (f=1/T) at which the pulses issue.

It should be appreciated using this architecture that pulses of unique shapes, and having many different phases, can be specified in a given pulse program. The '513 Publication explains that sine wave pulses, ramped pulses, and even pulses of random shapes, can be easily defined by concatenating different pulse phase types in the pulse program. For example, although not shown, a pulse program may comprise a number of successive stimulation phases (S) of increasing amplitudes, which would create a pulse with a rising stair-stepped shape.

Figure 5C:
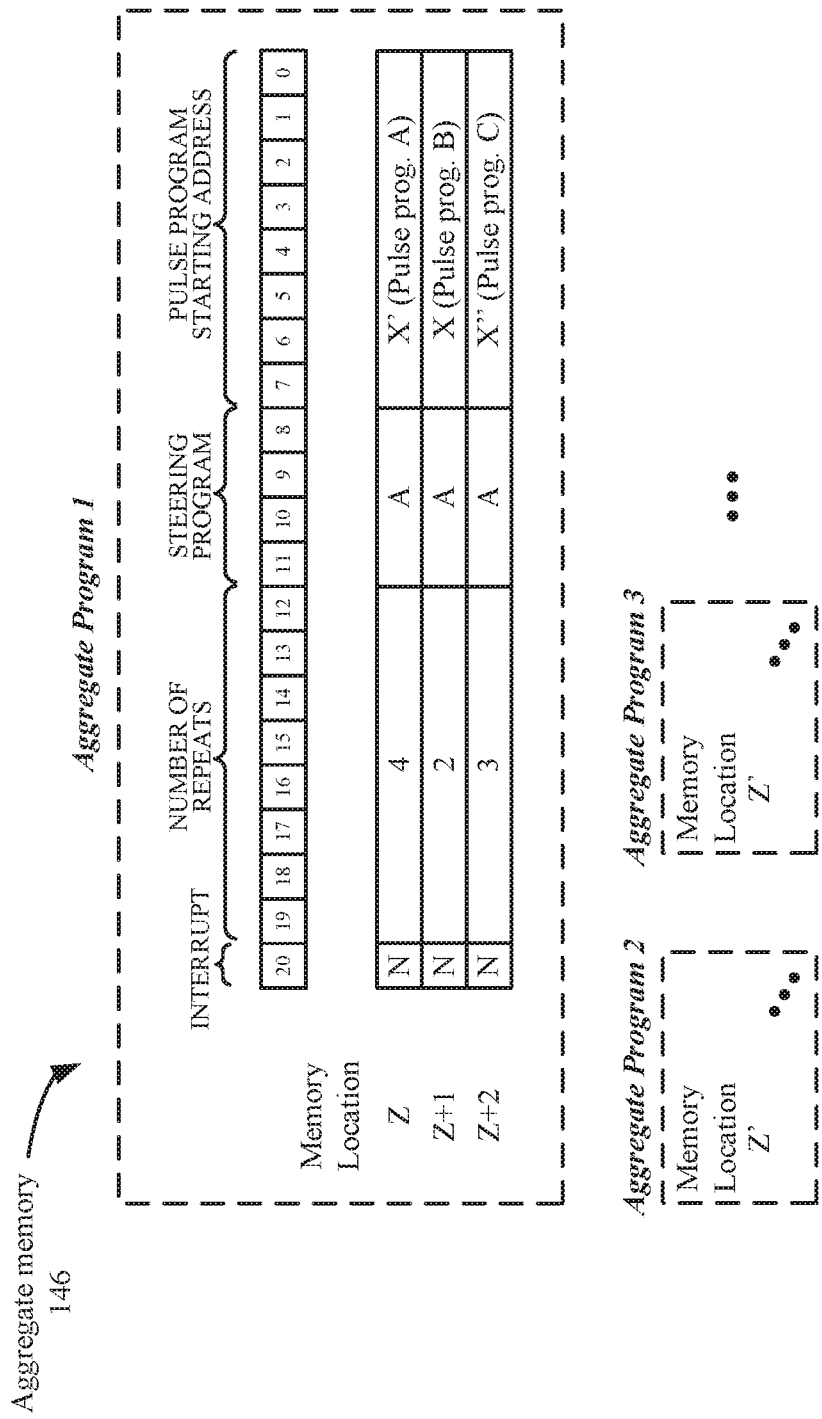

Any pulse program in memory 144 may be associated with any steering program in memory 142 to create pulses defined by the pulse program at the electrodes defined in the steering program, and this occurs by use of an aggregate program stored in aggregate memory 146, as shown in FIG. 5C. Each memory location of the aggregate program comprises an aggregate instruction that is formatted to associate a steering program with a pulse program, which can occur by specifying a particular steering program and the starting address of a pulse program. Further, each aggregate instruction specifies a number of times a pulse (including its various phases as specified in the pulse program) will repeat. Successive memory locations can define other aggregate instructions, specifying different pulse program/steering program associations and different pulse repeat numbers.

FIG. 5A shows the waveform formed using the aggregate program 1 of FIG. 5C. Three pulse programs A, B, and C are successively specified using three aggregate instructions in aggregate program 1, whose pulses are repeated 4, 2, and 3 times respectively. Notice in this example that the amplitudes specified in pulse programs A, B, and C are different, as are the durations of the pulse phases and the frequencies with which the pulses are issued. The same steering program A (FIG. 5B) is associated with each pulse program in aggregate program 1, specifying use of electrode E1 and as anode, and E2 as a cathode (although again these polarities can be flipped in accordance with the pulse phase type specified in the pulse program). Notice that the aggregate program 1 can be executed such that it repeats, as shown in FIG. 5A. Although not shown, this can be affected by defining the start (Z) and end (Z+2) memory location in the configuration memory 148 (FIG. 4A), or in the starting and ending aggregate instructions themselves.

FIG. 6 shows examples of external communication devices 160 that can be used to program the stimulation that the IPG 10 provides. Two examples of external devices 160 are shown: a clinician programmer (top), and a hand-held portable patient external controller (bottom), which are described in further detail in U.S. Patent Application Publication 2016/0051825. The clinician programmer is generally used by a clinician in their office or in a clinical setting such as an operating room, and may comprise a general purpose computer, such as a laptop, notebook, or tablet computer 162, and may include a screen 168 as well as other computer peripherals (keyboard, mouse, etc.) not shown. The patient external controller can comprise either a dedicated communication device designed for use in communicating with the IPG 10, or can comprise a portable general purpose computer device, such as a smart phone, personal data assistant, or tablet, as explained in the '825 Publication.

In either of these examples, the external device 160 can include control circuitry 166. Such control circuitry 166 may include a microprocessor, microcontroller, microcomputer, FPGA, DSP, or other digital logic structures capable of executing programs in a computing device. In one example, control circuitry 166 may comprise any of the types of i5 processors sold by Intel Corp., see https://www.intel.com/ content/www/us/en/products/processors/core/i5-processors.html. The control circuitry 166 is capable of executing external device software 164 programmed into the external device 160. External device software 164 can comprise instructions stored in a non-transitory computer-readable medium in the external device 160, such as in memory associated with or readable by the control circuitry 166. Such memory can comprise solid state, magnetic, or optical memories, or other types of non-transitory memory devices. External device software 164 may also be present on non-transitory computer readable media that exist outside of the external device 160 (e.g., on disks in a server, on a memory stick, etc.), which can then later be loaded into in the external device's memory.

External device software 164 when executed is able to generate a graphical user interface (GUI) 170 on the screen 168 of the external device 160 to allow for programming or adjusting the stimulation that IPG 10 provides. An example of GUI 170 is explained subsequently with respect to FIGS. 7A-7D.

The external device 160 can include telemetry circuitry with associated antennas 174 that are capable of bi-directionally communicating with the IPG 10 (i.e., with the IPG's antenna 34) via a wireless communication link 176. As was the case for the IPG's antenna 34, one or more antennas 174 used in the external device 160 can comprise a magnetic-induction coil or a short range RF antenna allowing for communication on link 176, via Bluetooth for example. As shown, the clinician programmer can include a telemetry wand 172 that can be placed in close proximity to the patient's IPG 10, which is particularly useful when magnetic induction communications are used.

Figure 7A:
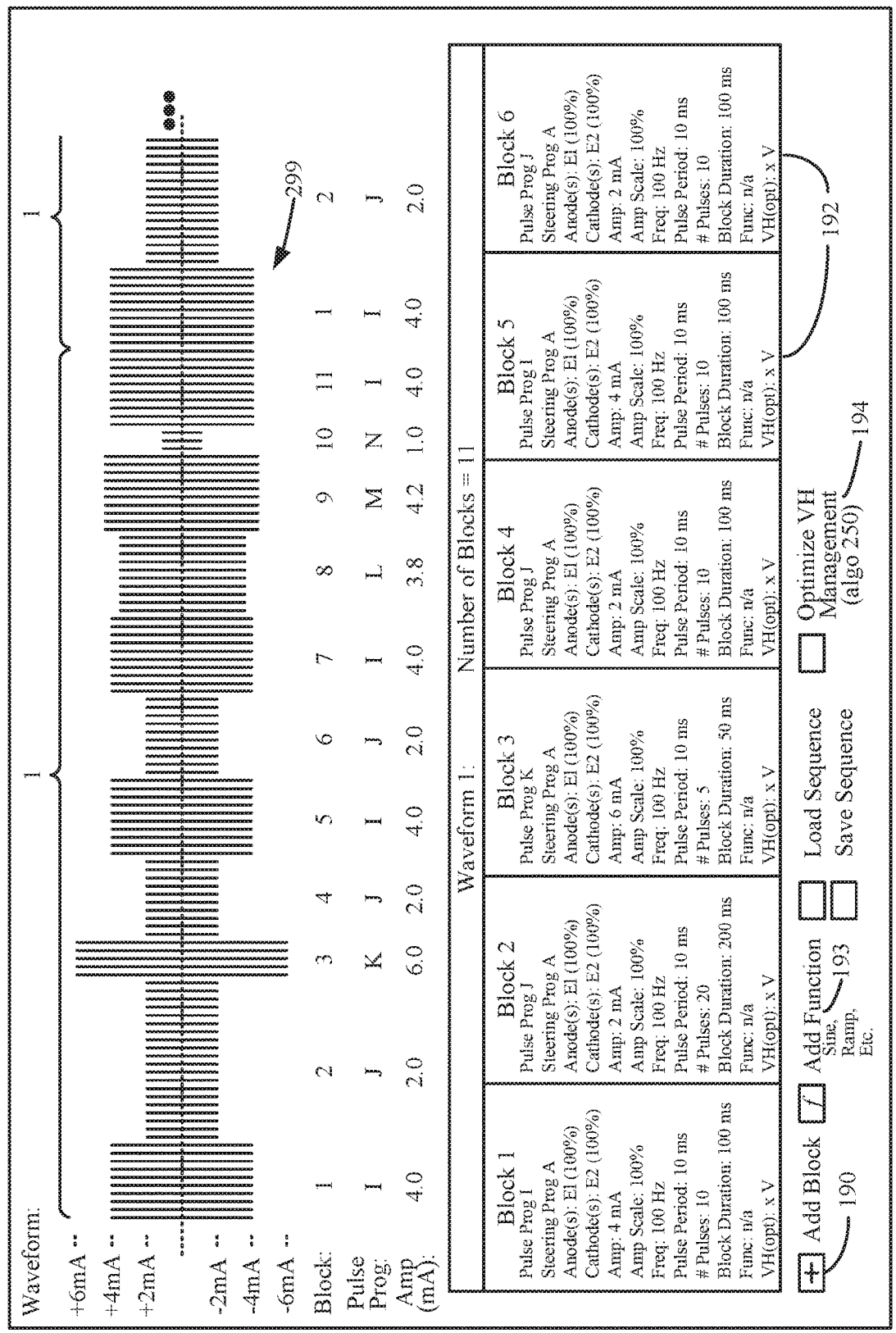

FIG. 7A shows an example of GUI 170 rendered on an external device to program the stimulation that IPG 10 provides. GUI 170 is particularly useful in programming the IPG 10, which as described earlier stores the stimulation waveform as an aggregate program (FIG. 5C) referencing steering and pulse programs (FIG. 5B). However, this isn't strictly necessary, and GUI 170 can instead be used to define and construct the stimulation waveform in other manners consistent with the stimulation circuitry 70 and DAC circuitry 72 used in a particular IPG 10.

In this example, a stimulation waveform 299 is formed by defining blocks of pulses, which can be concatenated together to form the waveform. Each of the blocks may be defined with reference to a steering program and a pulse program. The steering programs and pulse programs may be pre-existing and stored in the relevant external device, and thus can be made selectable by GUI 170 when defining each block. However, this is not strictly necessary, and although not shown, GUI 170 may also include options that allow a user to define a particular steering or pulse program. As shown in FIG. 7A, information for each of the blocks may be displayed in a block panel 192, and as explained further below such information may be editable or allow for user selection. Preferably, and as shown, the block panels 192 are displayed in chronological order, along with a graphical representation of the waveform 299.

In this example, a "block" may be generally understood as a sequence of similarly shaped and sized pulses, and as such may be defined using a given pulse program and a given steering program. Eleven blocks of pulses are shown in FIG. 7A. For simplicity, it is assumed that the pulses in each block are biphasic, and thus each pulse may comprise a plurality of phases, which may be defined by that block's pulse program, as explained earlier with reference to FIG. 5B. Each of these biphasic pulses are graphed in FIG. 7A for simplicity as comprising vertical lines with positive and negative polarities reflective of the amplitude of their first and second phases 94a and 94b. Blocks can also comprise pulses of any shapes, and need not be biphasic.

It is further assumed in the example that each of the blocks of pulses are applied to the same electrodes and in the same proportions. Specifically, each of the blocks of pulses use the same steering program A, as shown in FIG. 7C. As before (FIG. 5B), this steering program A may specify that electrode E1 comprises an anode receiving 100% of the anodic current A, and that cathode E2 comprises a cathode comprising 100% of the cathodic current A (again, this polarity could be flipped for different phases of the pulse, as explained earlier).

In this example, the blocks of pulses use different pulse programs specifying different constant current amplitudes. (Pulses may also be prescribed with reference to a voltage amplitude). Blocks 1, 5, 7, and 11 use pulse program I, which sets an amplitude A=4 mA. This amplitude may be the largest amplitude of all of the phases of the pulse, such as the actively-driven stimulation phase 94a. Blocks 2, 4, and 6 use pulse program J, which sets an amplitude A=2 mA. Block 3 uses pulse program K, which sets an amplitude A 6 mA, and which comprises the highest amplitude pulses in this example waveform 299. Blocks 8, 9, and 10 use pulse programs L (3.8 mA), M (4.2 mA), and N (1.0 mA) respectively. Note for simplicity that block panels 192 are only shown for blocks 1-6, although block panels for each block would ideally be shown in GUI 170. Pulse programs I-N are shown in FIG. 7C, with pulse program I shown in full detail, and with the other pulse programs shown more simply.

In this example it is assumed that the pulses in each of pulse programs, and thus in blocks 1-11, have the same basic timing. More specifically, the pulses have the same number of phases and the same durations for these phases. Thus, each of the pulses in these pulse programs have the same pulse period (e.g., 10 ms), and are issued at the same frequency (e.g., 100 Hz), as shown in FIG. 7A.

As noted above, a block preferably comprises a sequence of similarly shaped and sized pulses, and so a change in any stimulation parameter would preferably warrant defining different blocks. For example, a first block of pulses would preferably have the same amplitudes, the same pulse durations, the same shape, the same pulse periods (frequency) (e.g., per the pulse program), and are applied to the same electrodes (e.g., per the steering program). If any one or the parameters are changed, such new pulses are preferably formed in a second block.

As shown in FIG. 7A, GUI 170 allows the user to sequentially define the relevant blocks to define the stimulation waveform 299. In this regard, GUI 170 can include an option 190 to add a block to the waveform 299. When this option 190 is selected, a new block panel 192 can be presented to the user, allowing the user to specify the particulars for the pulses in the block. For example, the user can specify (e.g., in panel 192 for block 1), that pulse program I should be used to set the shape and size of the pulses, and that steering program A should be used to select the electrodes. Once so selected, this panel can reflect the selected electrodes (e.g., E1 as anode and E2 as cathode from steering program A), and reflect other important parameters, such as the (maximum) amplitude of the pulses, their frequency (e.g., 100 Hz), and the overall pulse period (e.g., 10 ms), which can be derived from the relevant pulse program for the block in question. Information concerning individual pulse phases (e.g., their amplitudes and durations) could also be reflected in block panels 192, but this isn't shown for simplicity.

Note that the fields in block panels 192 can also be manually populated, which allows the user to define the steering or pulse programs from scratch, or to change pre-defined steering or pulse programs that may already be stored in the external device. For example, for a given block, the user could select different anode or cathode electrodes in panel 192 to create a new steering program, or to change a pre-existing steering program. Similarly, the user could select different amplitudes, frequencies or pulse periods to create a new pulse programs, or to change pre-existing pulse programs. Individual phases of the pulses could likewise be selected and changed to define or change a pulse program, but this detail isn't shown.

Each of the block panels 192 also allows a user to specify a number of pulses that appear within each block. In the example of FIG. 7A, block 1 comprises 10 pulses (of the pulses specified by pulse program I); block 2 comprises 20 pulses (of pulse program J); block 3 comprises 5 pulses (of pulse program K); blocks 4, 5, and 6 comprises 10 pulses (of pulse programs J, I and J respectively). Although not shown currently in block panels 192, blocks 7-11 comprise 10, 10, 10, 3, and 10 pulses respectively (of pulse programs I, L, M, N, and I respectively). The GUI 170 can use the input number of pulses in each block (e.g., 10) and the pulse period (e.g., 10 ms) to compute and display a block duration (e.g., 100 ms in block 1). In addition, or alternatively, the GUI 170 can allow the user to input the block duration (e.g., 200 ms in block 2), which given the pulse period (e.g., 10 ms) will effectively set the number of pulses in each block (e.g., 20).

Each of the block panels 192 preferably also displays an optimal compliance voltage variable, VH(opt), to program the VH generator 76 during each block. How VH(opt) can be automatically be determined for each block, and how different blocks can be grouped and automatically assigned a single VH(opt) for the group, are discussed further below. However, note that the user or clinician can also use the block panels 192 in GUI 170 to manually enter VH(opt) for a particular block (or group).

Figure 7B:
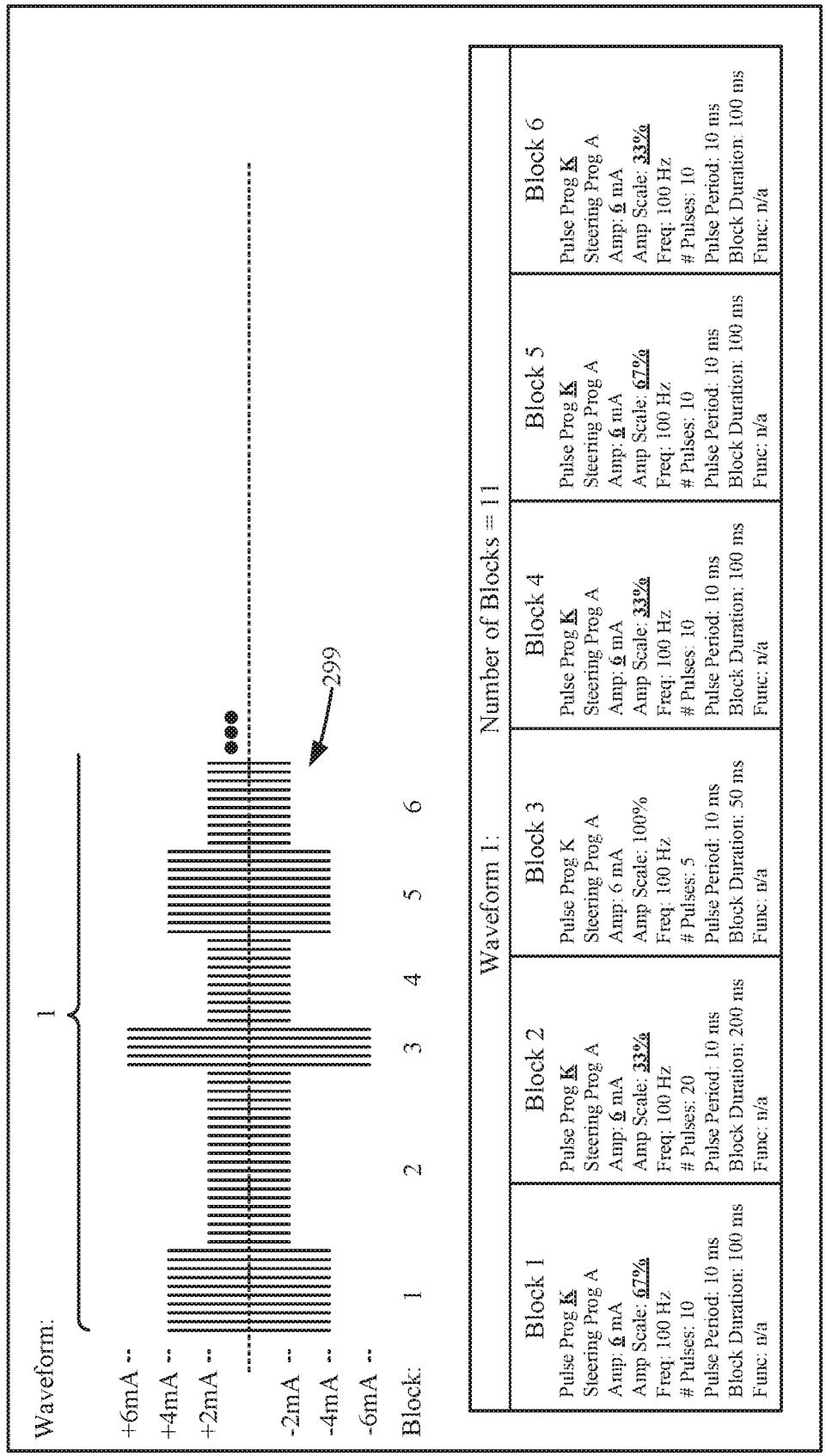

Block panels 192 may also include fields that allow the amplitudes of the pulses in each block to be modulated in various fashions. For example, the block panels 192 may allow a user to select overall amplitude scaling factors for the pulses in each block. In the example of FIG. 7A, the amplitude scaling factors are set to 100% in blocks 1-6, meaning that the pulses will be formed in these blocks in accordance with amplitude otherwise specified—i.e., by the amplitude field or in accordance with the amplitudes specified in the relevant pulse programs (e.g., 4 mA for blocks 1, 5, 7, and 11). FIG. 7B shows another example (using blocks 1-6 only) in which the simulation waveform 299 of FIG. 7A can be defined by using different amplitude scaling factors in each of the blocks. In this example, each of the blocks 1-6 are defined using only pulse program K, which specifies a maximum amplitude of 6 mA. The amplitude scaling factor is then adjusted in each block panel 192 to set the amplitude of the pulses in the blocks. Thus, blocks 1 and 5 are specified as having an amplitude scaling factor of 67%, meaning that the pulses in these blocks will have amplitudes of 67%*6 mA=4 mA as desired. Blocks 2, 4, and 6 are specified as having an amplitude scaling factor of 33%, meaning that the pulses in these blocks will have amplitudes of 33%*6 mA=2 mA as desired. Amplitude scaling is described further in U.S. Patent Application Publication 2020/0346019.

Figure 7D:
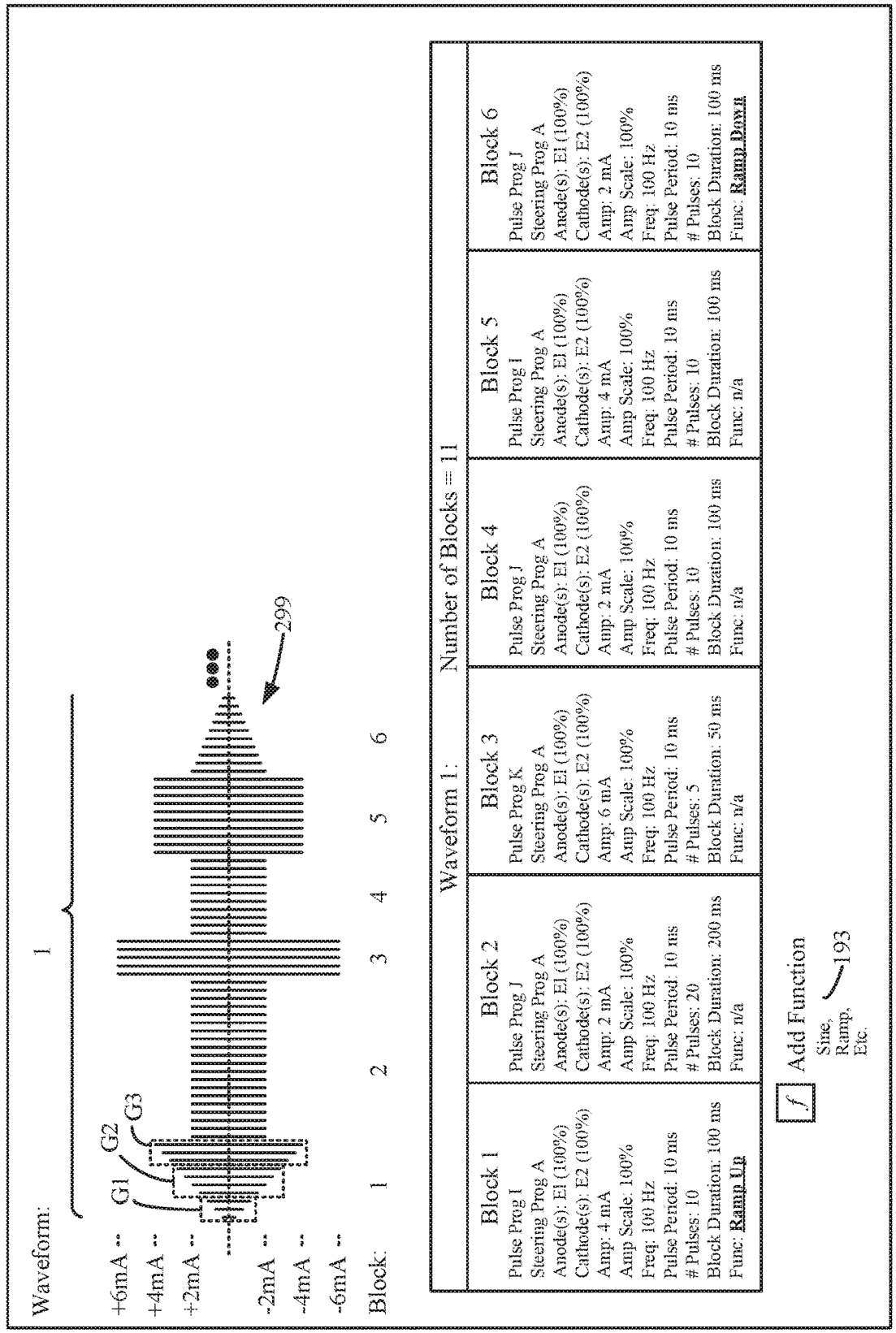

Further, the block panels 192 can modulate the amplitude of the pulses in the block using a function, such as by using option 193 in the GUI 170. Such function can operate to modulate the amplitude of the pulses within a block in accordance with the function's shape. FIG. 7D shows an example in which the function field in blocks 1 and 6 has been selected to include a function. Specifically, the function in block 1 is a "ramp up" function, and it can be seen in the waveform 299 that the pulses in block 1 gradually increase in amplitude. The function in block 6 is a "ramp down" function, and the pulses in block 6 thus gradually decrease in amplitude. Other time-varying functions, such as sine waves, or other shapes can be used to modulate the amplitudes within a given block. Although not shown, GUI 170 may allow the user to define other aspects of functions that may be applied within a block of pulses. For example, the GUI 170 may allow the user to define a ramp duration, which may smaller than the block duration, and which will ramp the amplitude of some of the pulses in a block while allowing others to remain at prescribed amplitudes. A function may independently set the amplitude of the pulses in a block without reference to a particular pulse program.

Once GUI 170 is used to define the waveform 299, the external device software 164 in the external device 160 can format appropriate programming information for the IPG 10, and the manner in which such formatting occurs can depend on the specifics of the stimulation circuitry 70 and the DAC circuitry 72 used in the IPG 10. For example, the software 164 can compile an aggregate program and transmit it to the IPG 10 along with any pulse or steering programs it references so that such data can be stored (in memories 142, 144, and 146, FIG. 4C) in the IPG 10 and executed. FIG. 7C shows aggregate program 1 indicative of the waveform 299 of FIG. 7A. As explained earlier, an aggregate program comprises one or more of aggregate instructions, with each instruction preferably provided in subsequent memory locations (Z, Z+1, etc.). As FIG. 7C shows, each aggregate instruction can comprise the information necessary to form pulses in each of the blocks, and so aggregate program 1 comprises eleven instructions corresponding to the eleven blocks defined in GUI 170 in FIG. 7A, including the number of pulses in each block.

If necessary, the external device software 164 can process the data prescribed in GUI 170 in a manner to fit the prescribed waveform 299 into a proper format for execution in the IPG 10. For example, if amplitude scaling is used (e.g., FIG. 7C), the external device software 164 may define new amplitude-modulated pulse programs, reference these new pulse programs in the aggregate program, and transmit the aggregate program and the new pulse programs to the IPG 10. That is, even though the user in FIG. 7C specified the use of pulse program K in the GUI 170, the external device software 164 may automatically define new pulse programs (akin to pulse programs I and J), and apply the amplitude scaling factor within these new pulse programs. Similarly, if a function is used to modulate pulse amplitudes in a block, the external device software 164 may determine a plurality of pulse programs as necessary to reflect the varying amplitudes that the function prescribes. For example, if ten pulses are ramped in a given block, the external device software 164 may determine ten new pulse programs each having a unique amplitude, and include ten aggregate instructions in the aggregate program for that block, with each instruction referencing one of the determined pulse programs. Each aggregate instruction may only specify the use of one pulse. Effectively then, the prescribed ramp could be constructed as ten individual blocks.

Although the stimulation circuitry 70 and DAC circuitry 72 in the IPG 10, and by GUI 170 in the external device, are beneficial in their ability to efficiently form and concatenate stimulation waveforms with varying pulses, the inventors realize that such flexibility gives rise to new challenges, in particular as concerns management of the compliance voltage, VH, that is used to power the DAC circuitry 72 and actively drive the currents at the electrodes.

Figure 8B:
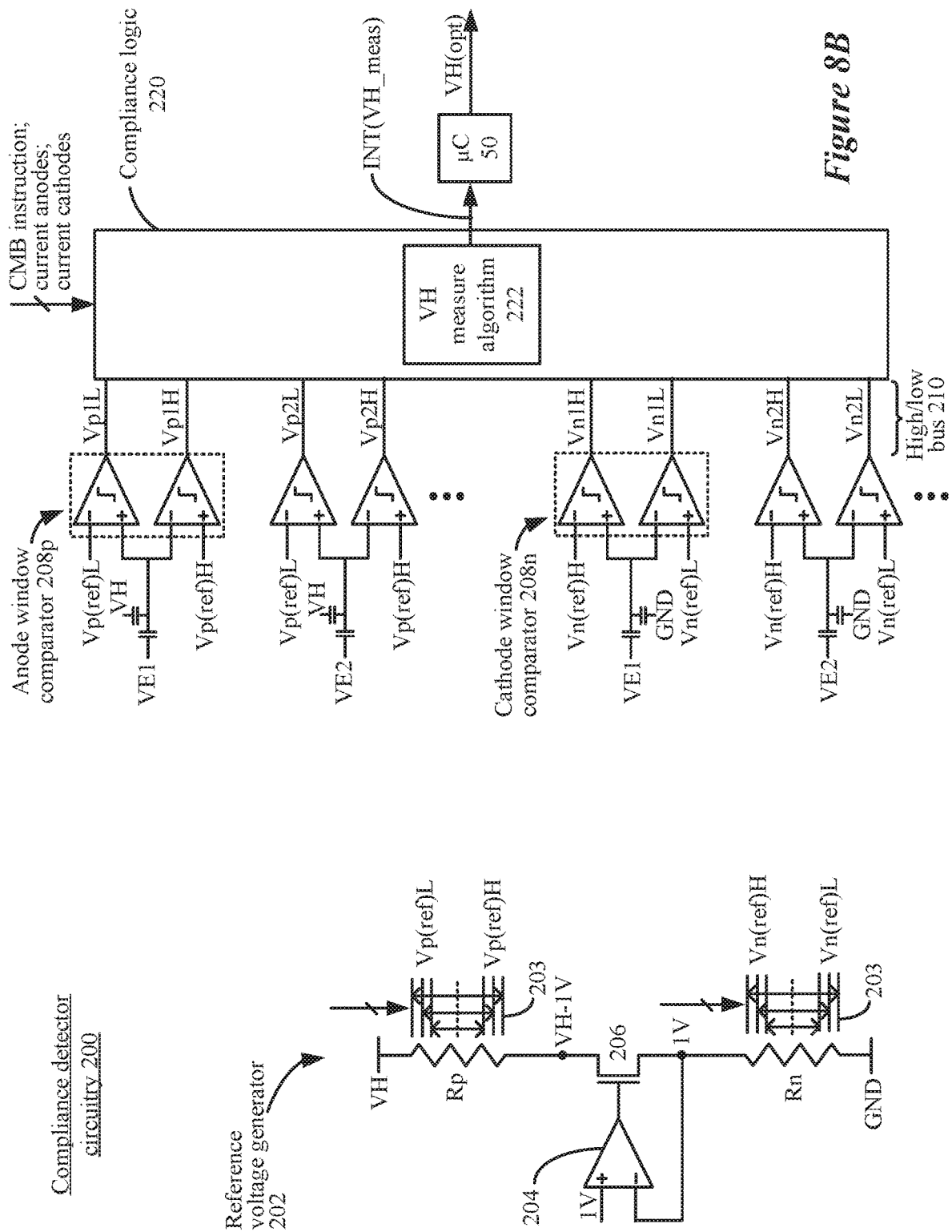

As discussed earlier, adjustment of the compliance voltage VH is desirable to ensure that stimulation pulses can be reliably formed without wasting power (the battery 14) in the IPG 10. To ensure that the compliance voltage is at a proper magnitude, measurements can be taken in the IPG 10, and FIGS. 8A and 8B discuss such details as taken from U.S. Patent Application Publication 2018/0071512, with which the reader is assumed familiar. FIG. 8A shows the basic circuitry involved in a providing stimulation between two electrodes E1 and E2. This was described earlier with respect to FIG. 3, and focus is provided here on measurements relevant to adjusting the compliance voltage VH. In this example, biphasic pulses of amplitude A (as dictated by a pulse program E) are provided between electrodes E1 and E2 (as dictated by a steering program A). These pulses may comprise an aggregate instruction in a larger aggregate program 1, and may comprise pulses within a particular block as discussed earlier with reference to FIGS. 7A-7D. The circuitry shows operation during stimulation phase 94a of the biphasic pulse, and thus shows PDAC1 activated to provide an anodic current of amplitude +A to E1, and shows NDAC2 activated to provide a cathodic current of amplitude −A to E2. Note that during active charge recovery phase 94b (when the polarity of the current is reversed), PDAC2 and NDAC1 would be activated, although this isn't shown.

When providing the pulses, a voltage Vrt will form across the patient's tissue Rt. Voltages VC1 and VC2 will also build across the DC-blocking capacitors C1 and C2 associated with electrodes E1 and E2. Further, voltages Vp and Vn will drop across the current active PDAC and NDAC. These voltages in sum equal the compliance voltage VH, i.e., VH=Vp+VC1+Vrt+VC2+Vn.

Vp and Vn are particularly useful in determining whether VH has been set to a proper level, and so are measured and assessed using compliance detector circuitry 200 described subsequently with respect to FIG. 8B. As will be explained subsequently, the compliance detector circuitry 200 assesses whether Vp and Vn are too high or low. If Vp or Vn are too low, then the PDAC or NDAC is effectively overloaded, and will not be able to provide the prescribed current A; that is, the resulting current though the tissue will be less than A. If Vp and Vn are too high, the current will be formed with the correct amplitude A. However, this is wasteful of power, because excessive voltage drops Vp and Vn across the PDAC and NDAC provide no useful effect.

FIG. 8A explains how the stimulation circuitry 70 in the IPG 10 can be programmed to dictate when compliance voltage measurements are taken. In this example, a compliance monitoring instruction is included within the pulse program E that is used to form the pulses. Such an instruction in this example comprises a compliance monitoring bit (CMB; bit 17), which can be set during any of the phases of the pulse, e.g., in any of the memory locations X, X+1, etc. describing such phases. The CMB instructs the compliance detector circuitry 200 to measure and process the voltages at the electrode nodes involved in providing stimulation (e.g., VE1 and VE2) during pulse phases in which the CMB is set.

It is preferred to set the CMB during pulses phases when the compliance voltage VH is most likely to be inadequate. In the example shown in FIG. 8A, and as shown in the magnified view of the waveform, this occurs just before the end of the first pulse phase 94a. This is the worst case for a biphasic pulse: at the end of the first pulse phase 94a, the DC-blocking capacitors C1 and C2 will be charged to their maximum extent, and thus the voltage across them (VC1, VC2) will be at their highest. This minimizes the voltage drops across PDAC1 and NDAC2 (Vp, Vn) for the same compliance voltage, VH, meaning that the PDAC1 and NDAC2 are at risk for having too little power to produce pulses of the prescribed amplitude. In other words, VH is mostly likely too low at this point, and hence it can be beneficial to take a compliance voltage measurement at this point to verify compliance voltage adequacy.

The timing of the compliance voltage measurement (e.g., at the end of pulse phase 94a) can be set in different ways, and could be prescribed in pulse program E along with the CMB. However, in the disclosed IPG architecture, compliance measurement timing is set using the stimulation circuitry 170's configuration memory 148 (FIG. 4C). As shown in FIG. 8A, this memory 148 can include a compliance monitor timing register 149, which defines when the compliance monitoring bit instruction will issue during the duration of the pulse phase in which it is set. Such timing may be defined in a number of ways. For example, the compliance monitor timing register 149 may specify a percentage during the duration (e.g., D2) of the pulse phase when the CMB should issue, with 1% specifying issuance of CMB at the beginning of the duration, and 99% specifying issuance at the end of the duration. Alternatively, register 149 can store a time offset (e.g., 1 μs) from either the beginning or end of the pulse phase at which the CMB should issue. Such time offset can be quantified by other measures of time, such as a number of cycles of a clock operating with the IPG 10.

FIG. 8B shows further details of the compliance detector circuitry 200. Circuitry 200 effectively determines the voltage drops across the active PDAC and NDAC circuitry, akin to Vp and Vn as shown in FIG. 8A. Such voltage drops Vp and Vn may be directly measured by compliance detector circuitry 200, using differential amplifiers for example. However, in this disclosed example, voltage drops Vp and Vn are determined inferentially by assessing whether the voltages at the active electrode nodes, e.g., VE1 and VE2, are too high or low—and hence whether the voltage drops Vp and Vn are too high or low.

Compliance detector circuitry 200 receives the electrode node voltages VEx and inputs each into an anode window comparator 208p and a cathode window comparator 208n. Cathode window comparators 208n receive cathode high and low reference voltages, Vn(ref)H and Vn(ref)L, formed using reference voltage generator 202 described further below. These reference voltages are referenced to ground, and thus Vn(ref)H is greater than Vn(ref)L. Cathode electrode node voltages are also referenced to ground, and so if a cathode electrode node voltage (e.g., VE2) is too high (>Vn(ref)H), meaning the Vn is too high, the cathode window comparator 208n will output a cathode high signal (e.g., Vn2H='1') to compliance logic circuitry 220, described in further detail in the above-referenced '512 Publication. If the cathode electrode node voltage is too low (<Vn(ref)L), meaning that Vn is too low, the cathode window comparator 208n will output a cathode low signal (e.g., Vn2L='1').

Anode window comparators 208p operate similarly, and also receive anode high and low reference voltages, Vp(ref)H and Vp(ref)L, formed using reference voltage generator 202. These reference voltages are referenced to VH, and thus Vp(ref)H is lower than Vp(ref)L. Anode electrode node voltages are also referenced to VH, and so if an anode electrode node voltage (e.g., VE1) is too low (<Vp(ref)H), meaning that Vp would be too high, the anode window comparator 208p will output an anode high signal (e.g., Vp1H='1'). If the anode electrode node voltage is too high (>Vp(ref)L), meaning that Vp would be too low, the anode window comparator 208p will output an anode low signal (e.g., Vp1L='1'). Thus, the window comparators 208 can establish four digital signals for each electrode node voltage (e.g., VE1), two of which are relevant when the electrode node is acting as a cathode (Vn1H, Vn1L), and two of which are relevant when the electrode node is acting as an anode (e.g., Vp1H, Vp1L). Together, these four signals for all of the electrodes comprise a high/low bus 210 received by the compliance logic 220.

As discussed above, the reference voltages received by the window comparators are formed by a window reference voltage generator 202. Generator 202 comprises an op amp 204, which receives a reference voltage, such as a 1V, and which outputs to a transistor 206. An upper resistance Rp is connected between the compliance voltage VH and one terminal of the transistor 206, and a lower resistance Rn is connected between ground and the other terminal the transistor 206. Feedback establishes the reference voltage (1V) across the lower resistor, Rn, and because Rp=Rn, the reference voltage is also dropped across the upper resistor Rp. The upper and lower resistances Rp and Rn comprise a number of taps 203, which taps can be selected to adjust the reference voltages Vp(ref)H and Vp(ref)L used by the window comparators 208p, and to adjust the reference voltages Vn(ref)H and Vn(ref)L used by the window comparators 208p.

Selecting various taps 203 to set the reference voltages is explained in further detail in the '512 Publication, but note that selecting these taps 203 effectively sets a window for optimal values for Vp and Vn. For example, assume via selection of the taps 203 that Vn(ref)H=0.6V and Vn(ref)L=0.4V, and Vp(ref)H is VH−0.7V and Vp(ref)L is VH−0.5 V. This establishes a maximum/minimum for Vn of 0.6V/0.4V, and a maximum/minimum for Vp of 0.7V/0.5 V. If then for example, VE2 from cathode electrode E2 is higher than 0.6V, Vn2H is asserted, meaning that Vn dropped across NDAC2 is too high. This might warrant (depending on the particulars of compliance logic 220) reducing the compliance voltage VH to save power. If VE2 is lower than 0.4V, Vn2L is asserted, meaning that the Vn drop is too low. This might warrant (again, depending on compliance logic 220) increasing the compliance voltage to ensure that pulses are formed with their prescribed amplitudes. Similarly, if VE1 from anode electrode E1 is lower than VH−0.7V, Vp1H is asserted, meaning that Vp dropped across PDAC1 is too high. This might warrant (depending on the compliance logic 220) reducing the compliance voltage to save power. If VE1 is higher than VH−0.5V, Vp1L is asserted, meaning that the Vp drop is too low. This might warrant (again, depending on compliance logic 220) increasing the compliance voltage to ensure that pulses are formed with their prescribed amplitudes.

As shown in FIG. 8B, the compliance logic 220 receives the compliance monitoring instruction (e.g., CMB) when issued during the appropriate pulse phase, and further receives information regarding which electrodes are currently acting as anodes and cathodes. This allows compliance logic 220 to know when to sample the signals on the high/low bus 210, and which of those signals are relevant to assess (e.g., Vp1H, Vp1L, Vn2H, Vn2L) at any given time. The compliance logic 220 may employ an VH measure algorithm 222 to assist in deciding when the compliance voltage, VH, may need adjustment (either up or down), and can issue an interrupt INT(VH_meas) to the control circuitry 50 in the IPG 10. Control circuitry 50 in turn, through its own programming, can control the VH generator 76 (FIG. 3) to either increase or decrease the value of VH by asserting a new value for VH(opt), as explained further with respect to FIGS. 9A and 9B. Examples of VH measure algorithms 222 and related circuitry operable in compliance logic 220 are discussed further in the '512 Publication, and are not reiterated here. Note that compliance logic 220 may be considered to comprise part of control logic 50.

The VH generator 76, as noted earlier, essentially comprises a DC-DC voltage converter, and outputs a compliance voltage VH as boosted from an another power supply available in the IPG 100, such as the voltage of the IPG 10's battery 14 (Vbat). As explained in the '512 Publication, different types of VH generators 76 can be used. VH generator 76 can for example, comprise an inductor-based boost converter (see, e.g., U.S. Patent Application Publication 2015/0134029). VH generator 76 can also comprise a capacitor-based charge pump, again described in the '512 Publication (see also U.S. Pat. Nos. 8,219,196; 9,233,254; 7,805,189). A charge pump implementation is described in detail here with respect to FIGS. 9A-10B, but again other VH generator circuits could be used as well.

Figure 9A:
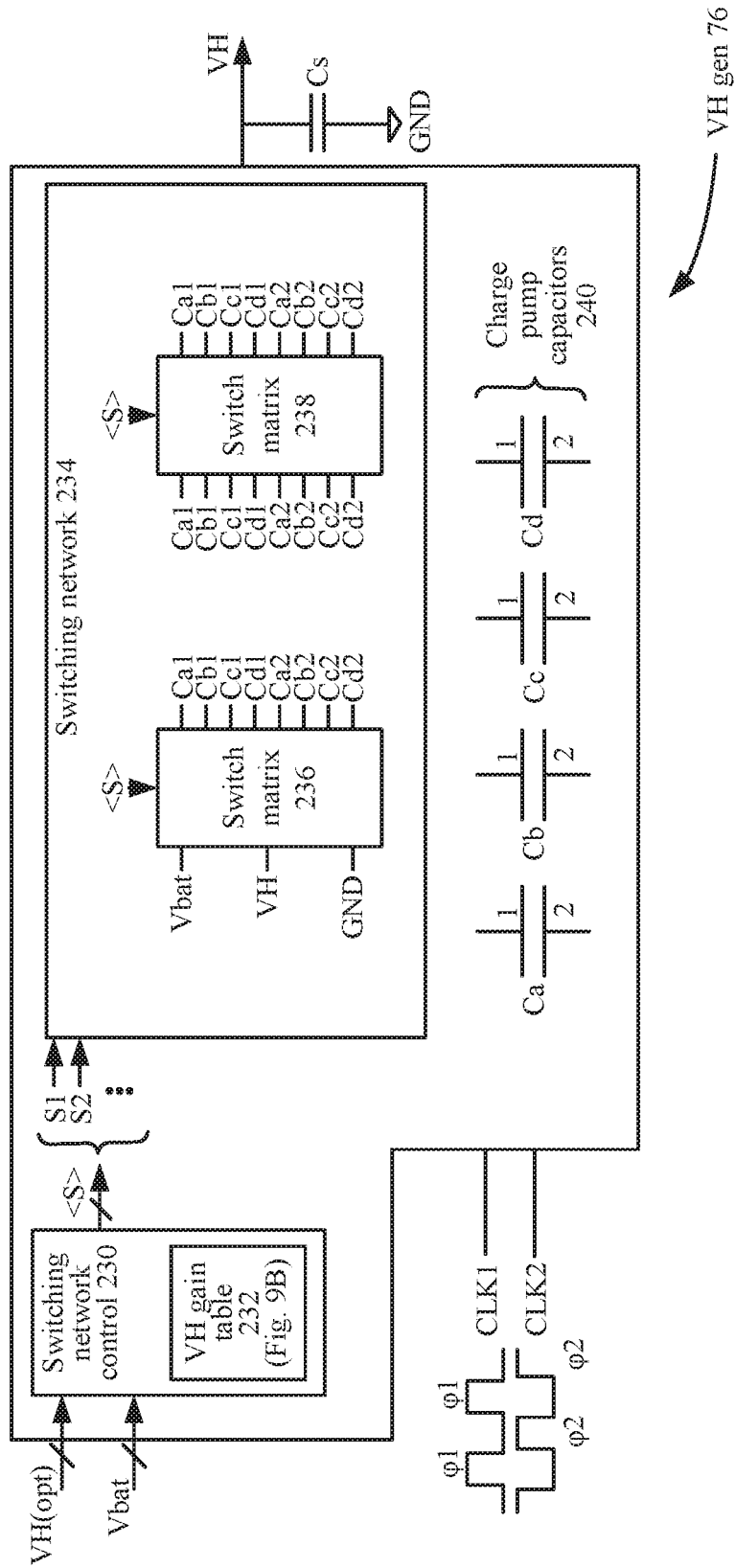

FIG. 9A shows an example of circuitry in the VH generator 76, including a plurality of charge-pump capacitors 240. Any number of capacitors 240 could be used, but the illustrated examples uses four: Ca, Cb, Cc, and Cd, each comprising a first plate (1) and a second plate (2). As explained further with reference to FIGS. 10A and 10B, these capacitors can, in different phases, be charged and then connected in together in different fashions to generate a desired compliance voltage VH.

The VH generator 76 is programmable to produce a compliance voltage VH in accordance with a programmed value of VH(opt), which may be prescribed by VH measure algorithm 222 in the compliance logic 220 when compliance voltage measurements are being taken, but which may also be prescribed in accordance with a VH management algorithm 250 to be described later. VH(opt) is preferably indicated using digital control signals. VH(opt) is input to switching network control circuitry 230, which in turn generates a number of digital switch control signals <S> received by a switching network 234. As explained further below, the switching network 234 operates to connect the plates of the capacitors 240 in various fashions and at different times. Switching network 234 can comprise a number of switch matrices, such as 236 and 238. Under control of switch control signals <S>, switch matrix 236 can connect any of the eight plates of the capacitors (plate 1 of Ca (Ca1), plate 2 of Ca (Ca2), plate 1 of Cb (Cb1), etc.) to a number of different voltages. For example, switch matrix 236 allows any one or more of these capacitor plates to be connected to ground or to the battery voltage Vbat. Switch matrix 236 also allows any one or more of the capacitor plates to be coupled to VH at the output of the generator 76. Switch matrix 238 allows any one or more of the capacitor plates to be connected to any one or more different capacitors plates. Specific examples of how switching network 234 can connect the capacitors 240 are explained further with reference to FIGS. 10A and 10B.

Figure 1A:
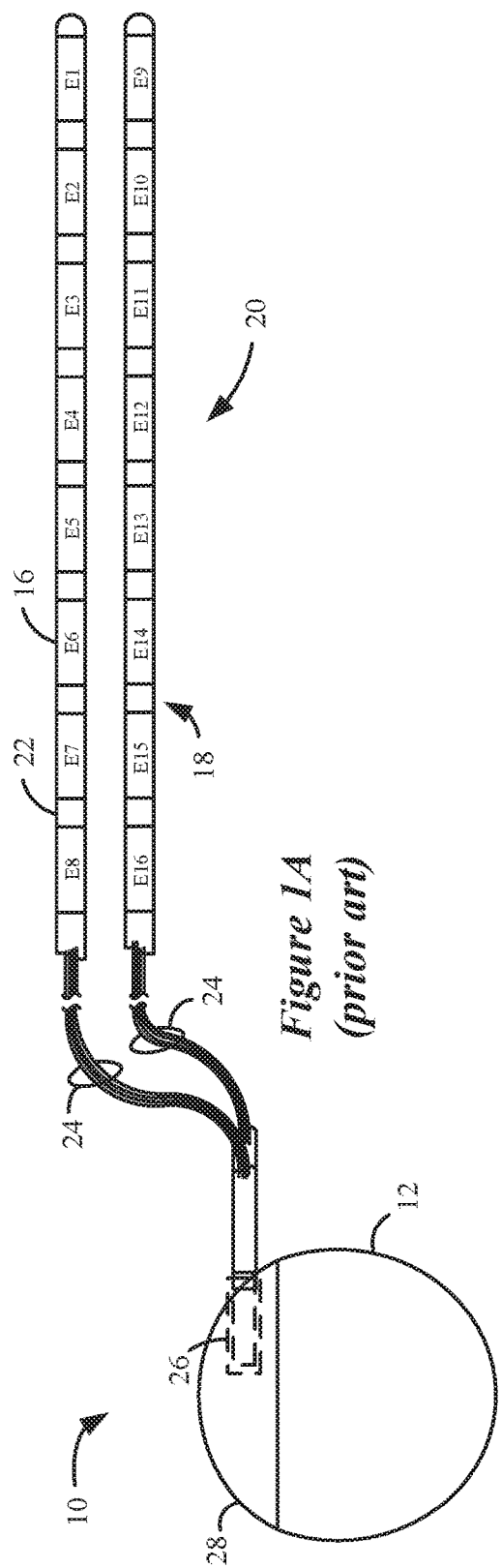
FIGS. 1A-1C show an Implantable Pulse Generator (IPG), and the manner in which an electrode array is coupled to the IPG, in accordance with the prior art.
Figure 1C:
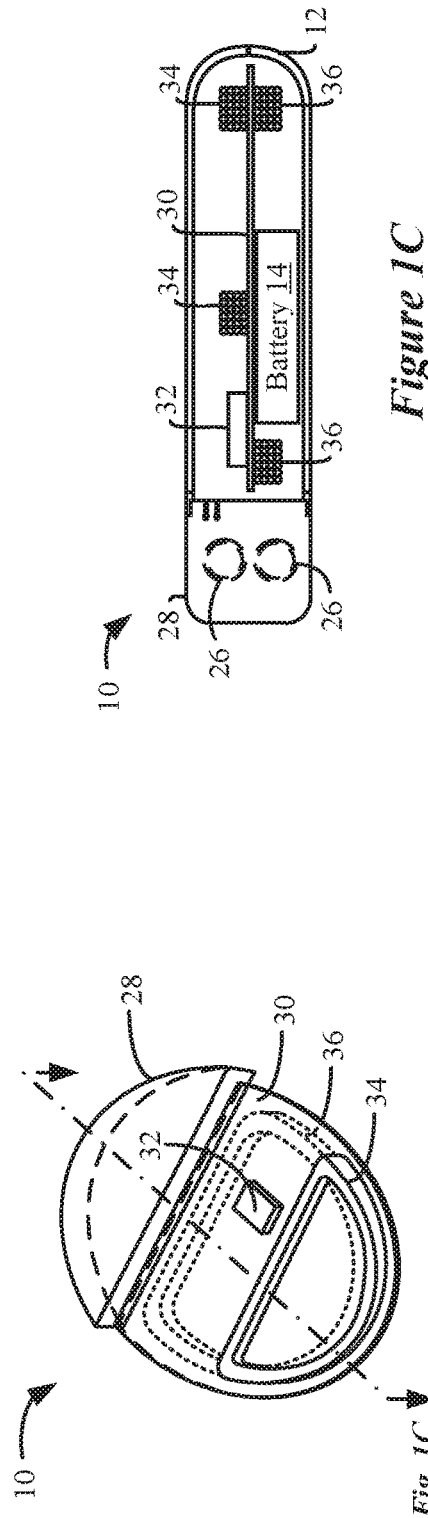
Figure 1B:
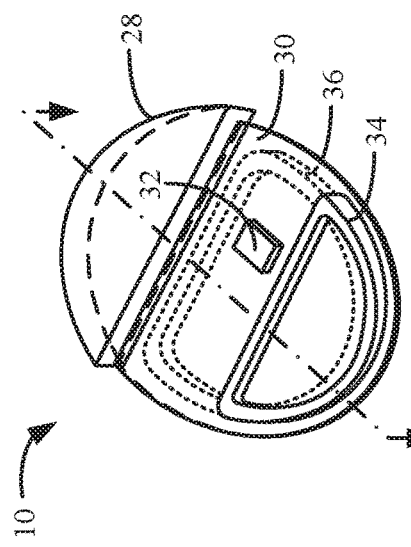
Figure 2:
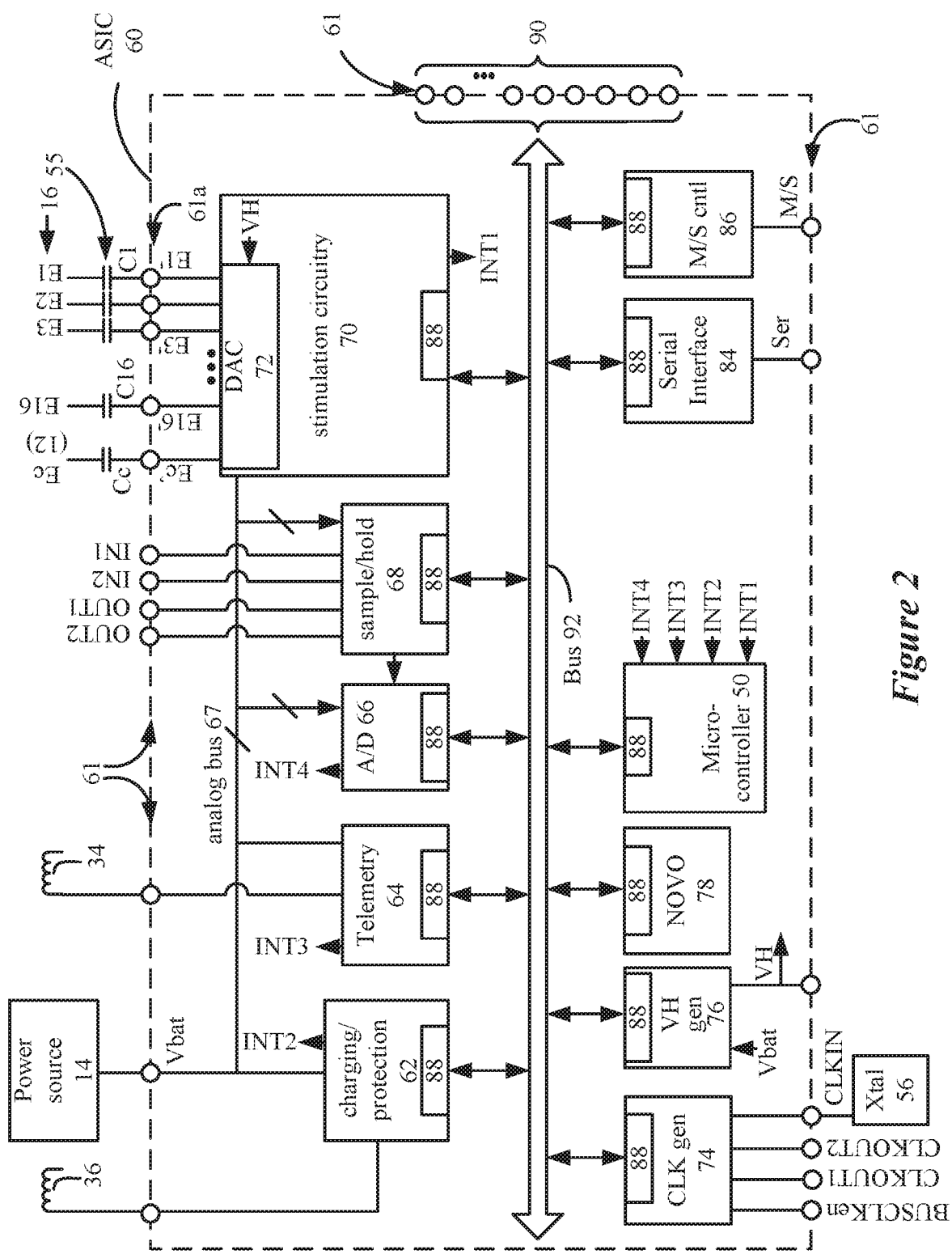
FIG. 2 shows an architecture for an IPG utilizing at least one Application Specific Integrated Circuit (ASIC).

Switching network control 230 also receives an indication of the present level of the IPG's battery, Vbat. Vbat is typically periodically digitized and stored in the IPG 10 (see A/D block 88, FIG. 2), and so can be provided to the VH generator 76 by the control circuitry 50 along with VH(opt). The switching network control 230 also includes, or is in communication with, a VH gain table 232, which is shown in further detail in 9B. Lastly, the VH generator 76 also receives a plurality interleaved clock signals, CLK1 and CLK2, which define first and second phases φ1 and φ2 for the switching network 234.

FIG. 9B shows information in the VH gain table 232 that is used by switching network control 230. As this table 232 reflects, VH is produced as a fractional multiple of the battery voltage Vbat, which each fractional multiples comprising a gain by which Vbat is boosted to produce VH (i.e., VH=gain*Vbat). In this example, nineteen possible gains are reflected in table 232, which allows VH to be produced as Vbat, 1.25*Vbat, 1.33*Vbat, and so on up to 8*Vbat. Table 232 also shows the various values of the switching control signals <S> needed to achieve the desired gain during the first and second phases φ1 and φ2. For example, if a gain of 4/3 is to be applied, setting VH=1.33*Vbat, then switching control signals <S3_1> are provided from the switching network control 230 to the switching network 234 during the first phase φ1, and switching control signals <S3_2> are provided during the second phase φ2. The particulars of the switch control signals <S> can vary in different implementations, and more or fewer gain values could be used and included in table 232. In large part, the switching control signals <S> depend on the number of gains the system will support, the particulars of the switching network 234, and the number of capacitors 240 used.

Notice that the compliance voltage VH output by the VH generator 76 is preferably connected to a storage capacitance Cs. The capacitance of Cs may be significant to keep VH relatively steady over time, and to remove ripple or variance from VH. Note that capacitance Cs may also inherently include the input capacitances of circuitry to which VH is provided, such as capacitances inherent in the DAC circuitry 72.

Figure 10A:
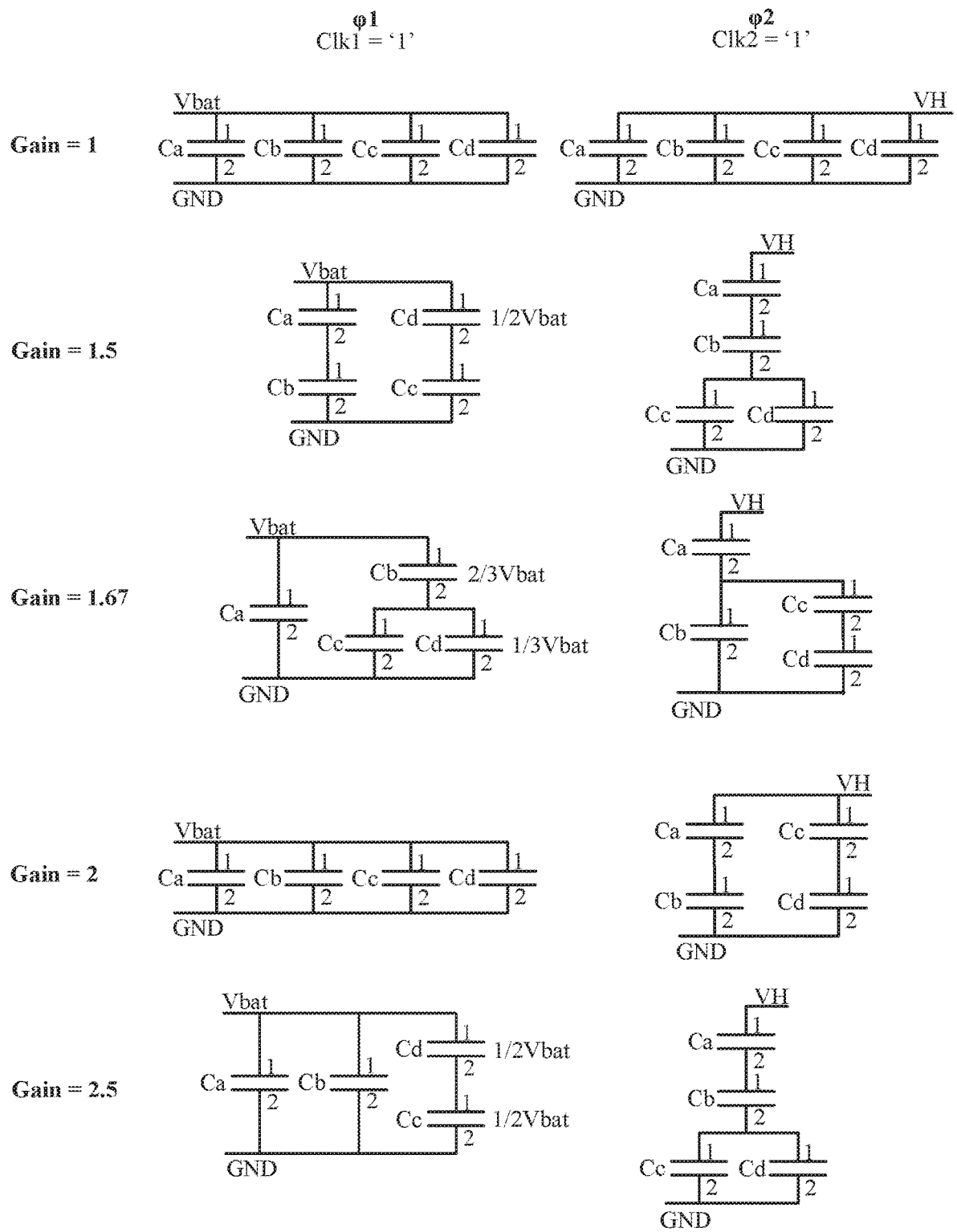
FIGS. 10A and 10B show examples of manners in which capacitors in the compliance voltage generator can be connected to derive a compliance VH with a particular gain value.
Figure 10B:
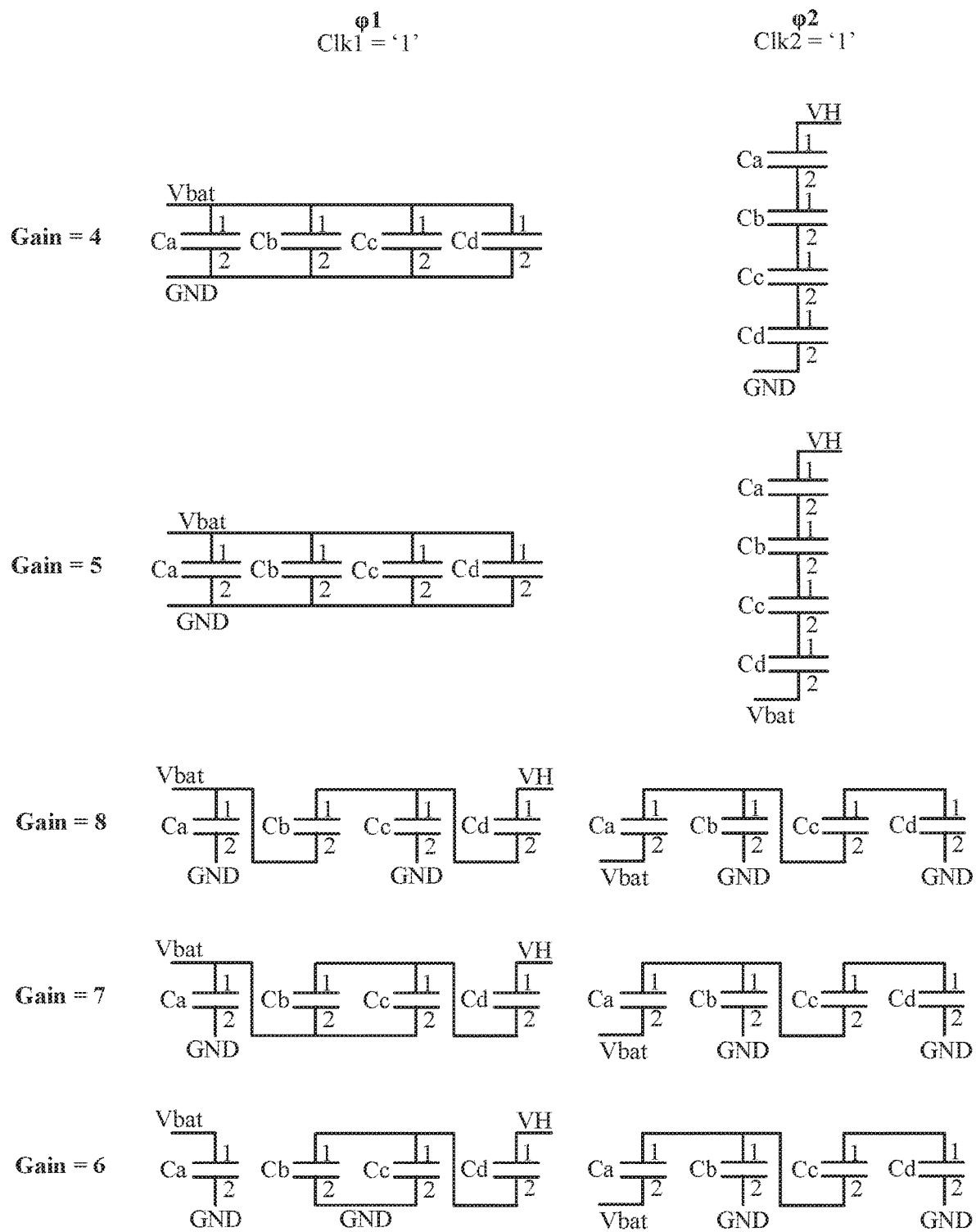

FIGS. 10A and 10B shows examples of how the switching control signals <S> control the switching network 234 to connect the various plates of the capacitors 240 for achieve different gain values. The top of FIG. 10A shows a simple example, in which VH simply equals Vbat for a gain of 1. Here, during the first phase φ1, as dictated by switching control signals <S1_1>, the first plates 1 of the capacitors are connected to Vbat, and the second plates 2 of the capacitors are connected to ground, thus connecting the capacitors in parallel, and charging each capacitor to Vbat. In the second phase φ2 (<S1_2>), this connectivity doesn't change, except now the first plates 1 of the capacitors are connected to output VH, which will equal Vbat. It should be understood that the first and second phases φ1 and φ2 are run continually, with φ1 followed by φ2 followed by φ1 and so on.

In the next example, VH is set equal to 1.5*Vbat, or a gain of 1.5. Here, during the first phase φ1 <S5_1>, capacitors Ca and Cb are connected in series, and Cc and Cd are connected in series, with these series connections connected in parallel between Vbat and ground. This charges each of the capacitors to ½Vbat. During the second phase φ2 (<S5_2>), the capacitors are connected with Cc in parallel with Cd, and with this parallel connection in series with Cb and Ca. Cc and Cd were previously charged (φ1) to ½Vbat, so their parallel connection also results in ½Vbat. When this ½Vbat is added in series to ½Vbat as previously stored Ca and Cb, 1.5*Vbat results at output VH. Other examples showing how gains of 5/3 (1.67), 2, and 5/2 (2.5) can be achieved are also shown in FIG. 10A, but these examples should not require explanation.

FIG. 10B shows other examples. In the first example, a gain of 4 is achieved by first (φ1, <S15_1>) charging all of the capacitors in parallel to Vbat, and then (φ2, <S15_2>) connecting these capacitors in series between ground and VH, which sets VH=4*Vbat. The next example—showing a gain of 5—is similar, expect that during the second phase (φ2, <S16_2>), the series connection is coupled to Vbat instead of ground, thus providing an additional Vbat voltages to the series, which sets VH=5*Vbat.

The next examples show how gains of 8, 7, and 6 can be achieved. These examples are more complicated, and involve connecting the capacitors in accordance with Fibonacci charge pump designs. See, e.g., W-H Ki et al., Analysis and Design Strategy of On-Chip Charge Pumps for Micro-Power Energy Harvesting Applications, IFIP/IEEE International Conference on Very Large Scale Integration—System on a Chip, Vol. 379, pp. 158-186 (2011).

Because VH is formed as a function of Vbat, it is useful that switching network control 230 (FIG. 9A) also receives the current value of Vbat. This allows switching network control 230 to retrieve the proper switch control signals as necessary to form the desired value of VH(opt) at output VH. For example, suppose the VH generator 76 is programmed to produce VH in accordance with VH(opt)=10V. If Vbat is currently 2.0 V, a gain of 10/2=5 would be required to form 10V at VH, which the switching network control 230 can compute. The switching network control 230 can then consult table 232 to see if this gain value of 5 exists in the table, which in this example it does (FIG. 9B). Accordingly, switching network control 230 can retrieve from table 232 the necessary switch control signals and provide them to the switching network 234 so that they can be applied at the correct times (i.e., <S16_1> during φ1 and <S16_2> during φ2) to produce the proper gain. Suppose instead that Vbat is currently 3V. This would require a gain of 10/3=3.33. This particular gain value of 3.33 is not exactly represented in the table 232. Thus, switching network control 230 may pick the closest next-highest gain that is reflected in the table 232, i.e., 3.5. Thus, switching network control 230 can provide to the switching network 234 the necessary switch control signals for this next-higher gain (i.e., <S14_1> during φ1 and <S14_2> during φ2). Notice that this means that VH generator 76 may produce a VH that may be slightly higher than VH(opt) as desired. For example, if a gain of 3.5 is used, VH will equal 3.5*3V=10.5 V, instead of 10V prescribed by VH(opt). Producing a VH that is slightly higher than VH(opt) is slightly power inefficient, because VH is higher than it needs to be, but this is acceptable: pulses will still be formed with their prescribed amplitudes if VH is slightly higher than necessary, as explained earlier.

Figure 11A:
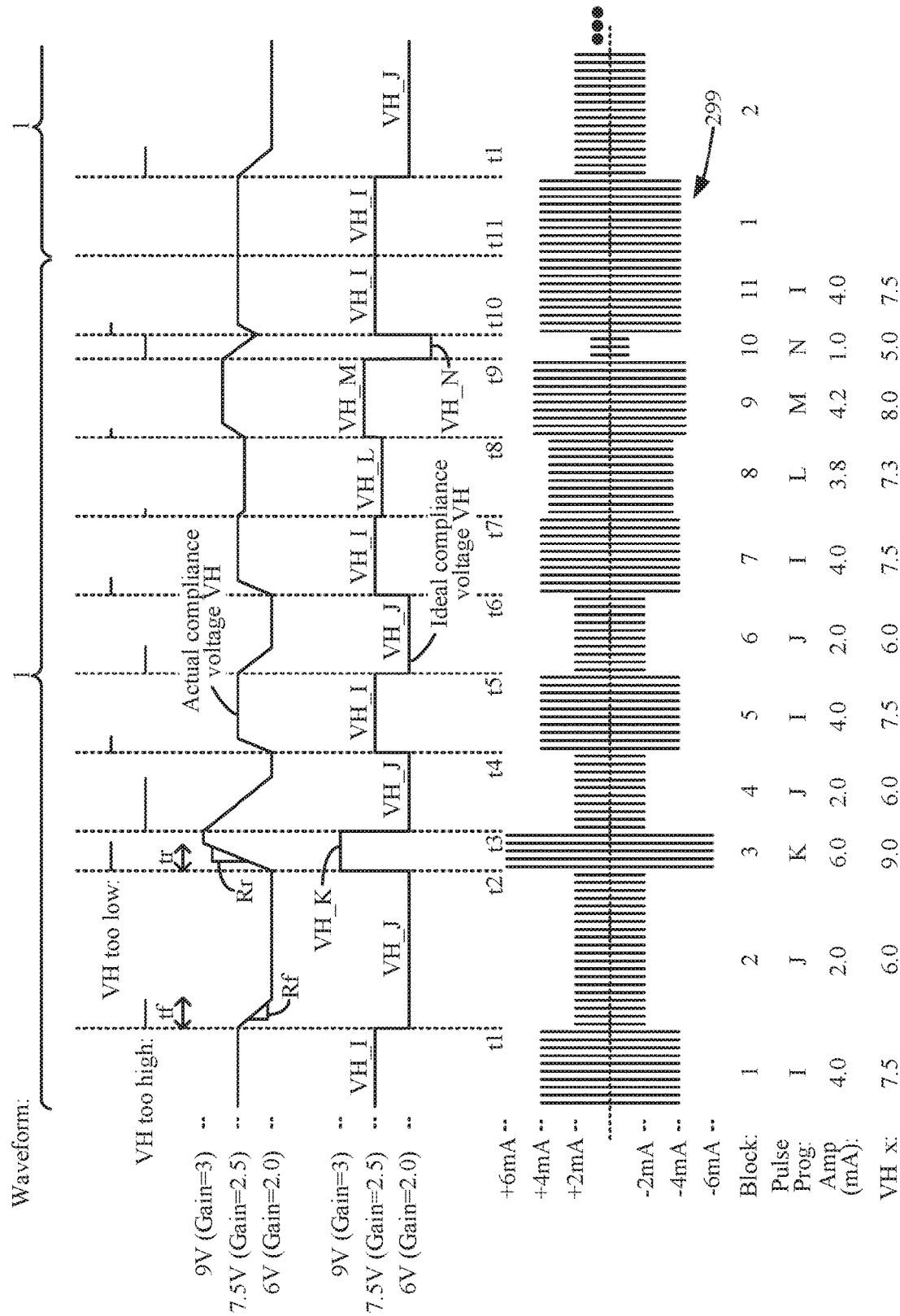
FIG. 11A shows the example complex waveform of FIG. 7A, and shows that while compliance measurement instructions can be used to automatically adjust the compliance voltage VH, VH can still be too low to adequately form some of the pulses of higher amplitudes.

FIG. 11A returns to the example waveform 299 that was described in FIG. 7A, which includes blocks of pulses with different amplitudes formed in accordance with pulse programs I (4 mA), J (2 mA), and K (6 mA), L (3.8 mA), M (4.2 mA), and N (1.0 mA). FIG. 11B shows a table 313 depicting relevant information for the waveform 299 and for each of the blocks. Table 313 may be generated by the external device 160 and its software 164 (FIG. 6) once the user has defined waveform 299. Table 313 can include the duration of the blocks, the number of pulses in each block, and a pulse program for each block, which, among other details, prescribes the amplitude of the pulses in each block. As will be shown, the information in table 313 can be tracked and updated using a VH management algorithm 250, as explained subsequently.

Also shown in FIG. 11A are the compliance voltages VH which would be ideal to form the pulses in each of these blocks. The value of these ideal compliance voltages will depend on different factors, such as the resistance of the tissue Rt between the selected electrodes (FIG. 8A), the extent to which DC-blocking capacitors may be charged (FIG. 8A), and the optimal voltage drops Vp and Vn across the DACs (as set for example by the reference voltages used with the window comparators 208p and 208n of FIG. 8B). FIG. 11A assumes that these ideal compliance voltages would comprise VH_I=7.5V for the pulses of program I, VH_J=6.0V for program J, VH_K=9V for program K, VH_L=7.3V for program L, VH_M=8.0V for program M, and VH_N=5.0 for program N. Note that these ideal compliance voltages may be constrained to voltages that VH generator 76 is able to produce, which can depend on the current value of Vbat and the gains VH generator 76 is able to produce (per VH gain table 232, FIG. 9B). For example, and assuming that the current battery voltage is Vbat=3.0V, then VH_I (7.5V) may comprise a gain of 2.5; VH_J (6.0V) may comprise a gain of 2; and VH_K (9.0V) may comprise a gain of 3.

These ideal compliance voltages VH_x would ideally be applied to the DAC circuitry 72 exactly when required—that is, that VH_I would be applied exactly when all pulses in pulse program I issue; VH_J would be applied exactly when all pulses in pulse program J issue, etc. However, this may not be possible because the VH generator 76 may not be able to instantaneously adjust the compliance voltage VH, even if the IPG is programmed (per CMB) to measure the adequacy of the compliance voltage.

Assume for example, at t1 (FIG. 11A), that it is desired to reduce VH from 7.5V (ideal per pulse program I) to an ideal value of 6V (ideal per pulse program J). If the CMB in pulse program J is set to take compliance voltage measurements, compliance logic 220 and/or control circuitry 50 would reasonably determine just after time t1 that Vp and/or Vn are too high, and that VH can be lowered. Compliance logic 220 and/or control circuitry 50 in the IPG 10 would thus starting lowering VH—by providing a smaller value of VH(opt) to the VH generator 76. But this may merely result in an incremental lowering of VH, with VH measure algorithm 222 used in compliance logic 220 and/or the control circuitry 50's programming only adjusting VH by one "step." Such a "step" may comprise a next-highest or -lowest gain when a capacitor-based charge pump is considered. For example, assume prior to t1 that Vbat=3.0V, that VH in the VH generator 76 is set to VH(opt)=7.5V (a gain of 2.5). When compliance logic 220 and/or control circuitry 50 decides per compliance voltage measurements taken after t1 to lower VH, it may only lower VH in accordance with a next-lowest gain in table 232 (FIG. 9B). This next-lowest gain would be 2.33, and as such control circuitry 50 may program the VH generator 76 with VH(opt)=7V. This is still too high for the pulses prescribed by pulse program J. So, as subsequent pulses issue, and further compliance voltage measurements are taken during pulse program J as execution of waveform 299 repeats, eventually the control circuitry 50 would set VH(opt) to the ideal value of VH_J=6.0V (a gain of 2 per table 232). The point is that even if compliance voltage measurements are taken, the VH generator 76 may not be immediately controllable to produce VH at optimal values.

Even if VH generator 76 can be immediately controlled to produce VH at optimal values, it may simply be the case that the VH generator 76 cannot lower VH instantaneously. Assume immediately after time t1 that the control circuitry 50 is able to set VH(opt) to the ideal optimal lower value of VH_J=6V. Capacitance at the output of the VH generator 76 (e.g., Cs, and other inherent capacitances, FIG. 9A) may be significant, such that VH cannot fall instantaneously, and therefore it may take some time for VH=6V to be achieved after t1. The rate at which VH can change may also be dictated by other factors, such as the frequency of the clock signals CLK1 and CKL2 that specify phases φ1 and φ2 for the charge pump, and the overall load that VH must drive (see FIG. 8A).

In short, and for these reasons or others, it may simply take time (tf) for VH to achieve its optimal level of VH_J=6.0 after time t1 as governed by a fall rate Rf, as shown in FIG. 11A. Thus, some of the initial pulses during fall time tf in block 2 (pulse program J) will have a compliance voltage VH that is too high (e.g., higher than the ideal value of VH_J=6.0V). This is not ideal from a power efficiency standpoint, but isn't particularly problematic, as these initial pulses in block 2 will be formed with their specified amplitudes. Notice in FIG. 11A that this same inefficiency of VH being too high can result whenever the compliance voltage is ideally lowered, e.g., from block 3 (pulse program K=4.0 mA) to block 4 (pulse program J=2.0 mA) at time t3.

By contrast, the inability to instantaneously provide an ideal desired output VH is more problematic in instances when the VH generator 76 needs to increase VH. This is the circumstance for example when the pulses in the waveform 299 increase in amplitude, such as between blocks 2 (pulse program J=2.0 mA) and 3 (pulse program K=6.0 mA) at time t2. In this circumstance, VH would ideally be instantaneously increased from VH_J (6.0V) to VH_K (9.0V). However, for the same reasons just described, this may take some time (tr), and the VH generator 76 may only be able to increase VH with a certain rise rate, Rr, which may be different from the fall rate, Rf. This inability to instantaneously increase VH at time t2 presents a more significant problem, because the actual compliance voltage VH for the initial pulses during rise time tr in block 3 are too low. Thus, these initial pulses will not be produced with their prescribed amplitudes, for example as set in GUI 170 (FIG. 7A). Again, this concern of VH being too low can result whenever the compliance voltage is ideally increased, e.g., from block 4 (pulse program J=2.0) to block 5 (pulse program I=4.0 mA) at time t4.

Thus, while the IPG 10 may by virtue of compliance voltage measurements (CMB) be able to automatically adjust VH to ideal values, such adjustments may not proceed quickly enough to accurately form pulses in a time-varying waveform such as waveform 299. Furthermore, continually measuring the compliance voltage (e.g., upon the issuance of every pulse) is not preferred as this can be burdensome. Such compliance voltage measurements will draw some power in the IPG 10, which will deplete the battery 14 more quickly.

It would be beneficial therefore to provide a system where VH(opt) is efficiently set when the waveform 299 is defined (e.g., using GUI 170) and in a manner to ensure that all pulses in the waveform are formed correctly. Furthermore, it would be beneficial that such management of VH occurs automatically in the system—that is, without the need of the user to specify when or how VH(opt) should be adjusted. Furthermore, it is desirable that the system be able to automatically and efficiently prescribe when and how compliance voltage measurements are taken to verify that values determined for V(opt) are sufficient over time, and to adjust these values over time if necessary. In other words, it is desirable that the user simply be able to use GUI 170 (FIG. 7A) to create waveforms of any desired shapes and amplitudes, with the system handling VH management behind the scenes and without need for user input.

In furtherance of these purposes, a VH management algorithm 250 is disclosed which is particularly useful in managing VH when a time-varying waveform such as waveform 299 is prescribed for use in a patient's IPG 10. The VH management algorithm 250 preferably analyzes the waveform, and breaks the waveform down into a number of groups of pulses, each of which may comprise a single block of pulses, multiple contiguous blocks of pulses, and/or one or more contiguous pulses. Each of the groups will be treated similarly from a VH management standpoint. Optimal compliance voltages VH(opt) are determined for each group, and such optimal VH values may be determined by taking compliance voltage measurements in the IPG 10. The time needed for VH to rise or fall when it must transition between groups is determined, and again may be measured. These rise or fall times are then used to set when the compliance voltage should increase or decrease, and to help in defining the relevant compliance voltage groups. In particular, when VH must rise at a transition, the algorithm 250 will automatically set VH(opt) to start adjusting VH in advance of the transition so that VH is at the proper higher value when the transitions occurs. The algorithm 250 is able to automatically compile necessary programming instructions to allow the IPG to produce the waveform—including necessary aggregate, pulse, and steering programs—and may further include instructions (possibly within the programming instructions) regarding how and when VH should be adjusted in the IPG. The algorithm 250 may additionally include instructions (again, possibly within the programming instructions) informing when compliance voltage measurements should be made in the IPG to verify that VH(opt) is in fact properly set at all times, and to adjust VH(opt) over time if necessary. The algorithm 250 can also operate in whole or in part in the IPG 10 itself, as explained further below.

Figure 12A:
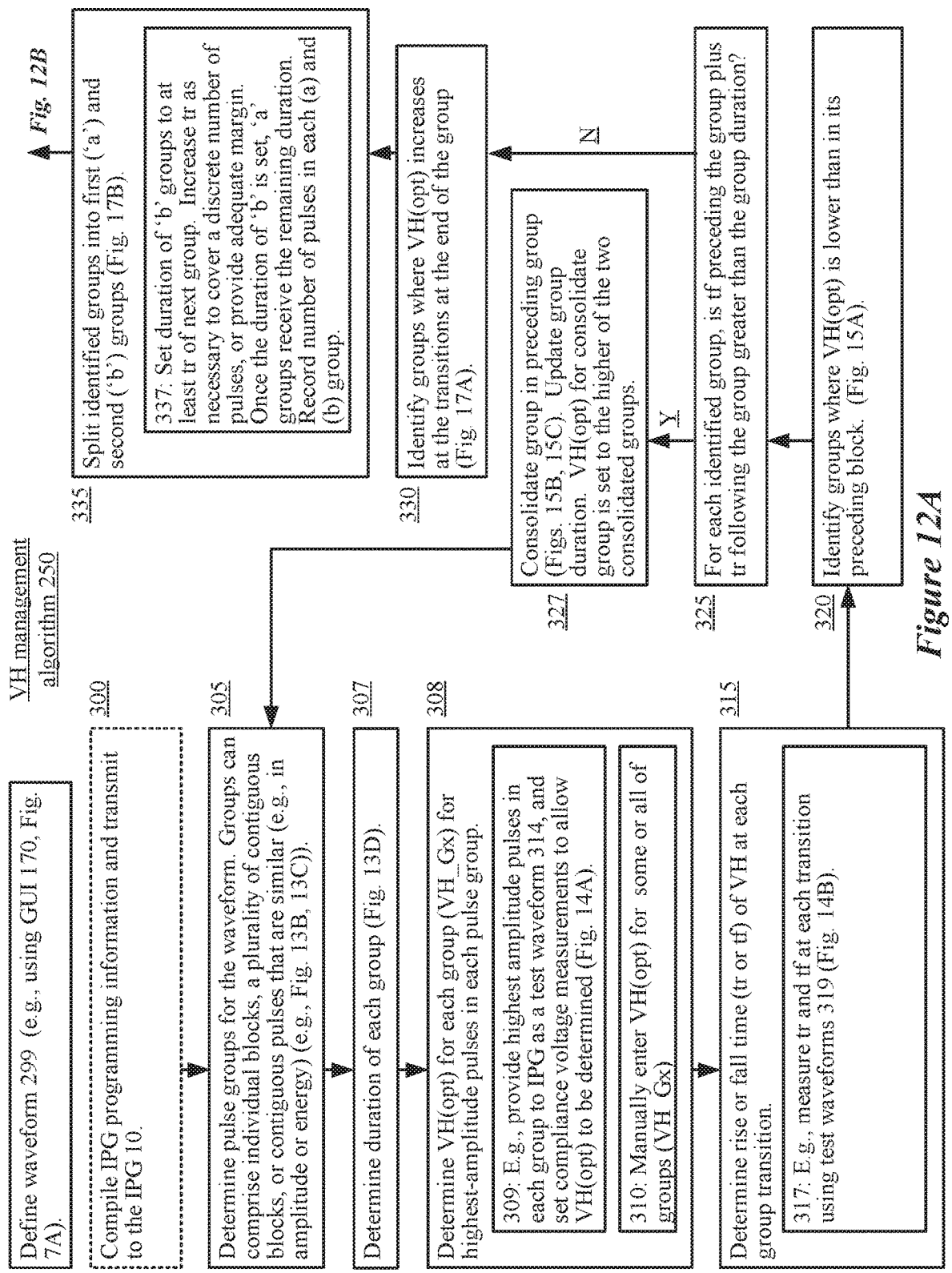
Figure 12C:
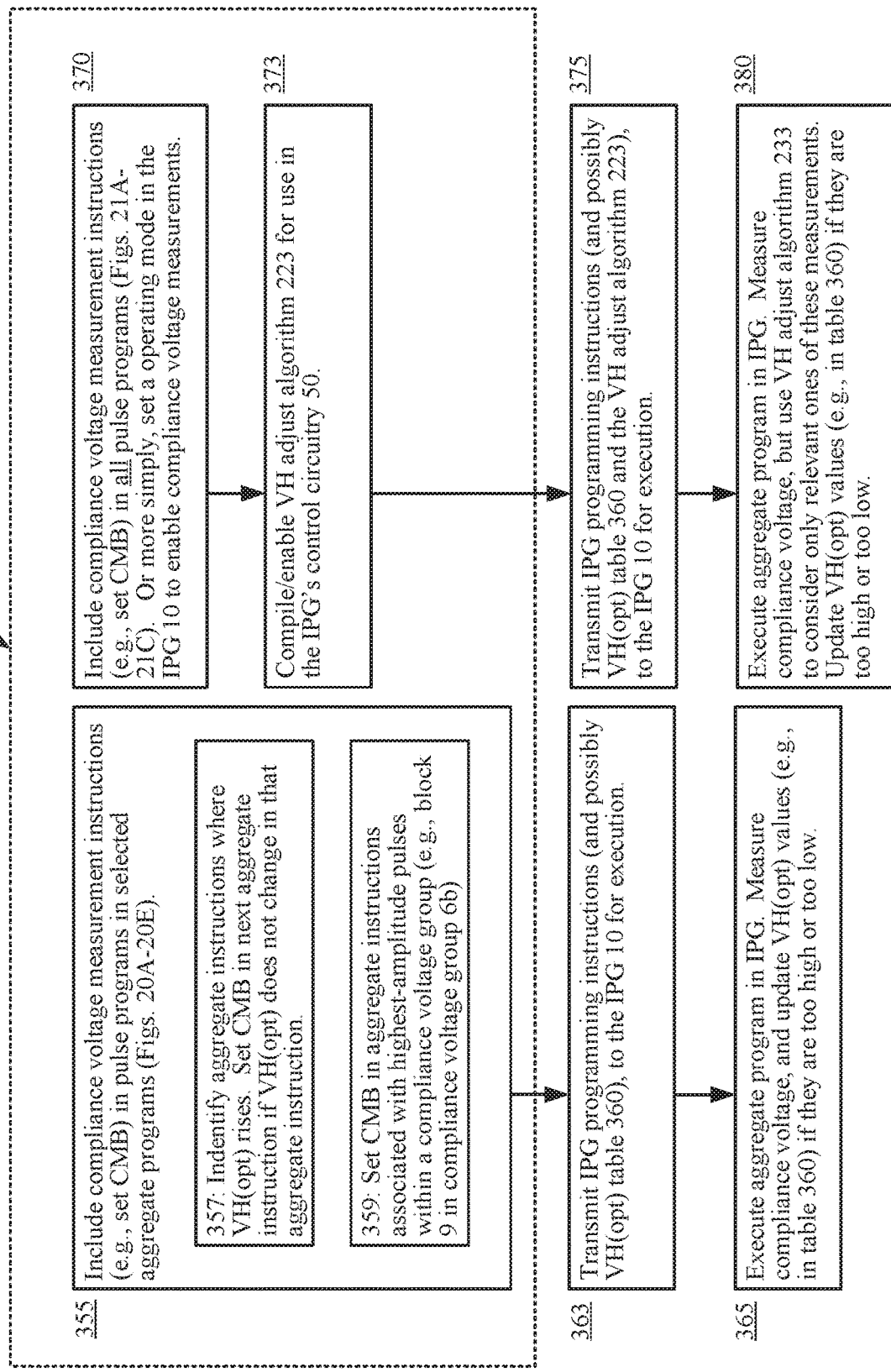

An example of the VH management algorithm 250 is disclosed in FIGS. 12A-12C, with steps in the algorithm being further described in detail with respect to FIGS. 13-21C. Not all steps illustrated in algorithm 250 are strictly required, and other steps could be added in a different implementation.

VH management algorithm 250 uses as its input a waveform 299, which may be defined using for example GUI 170 (FIG. 7A) of external device 160 (FIG. 6). This is not strictly necessary however, and the input waveform 299 can be defined in other manners. Once a waveform 299 is defined, algorithm 250 can automatically operate, or the operation of algorithm 250 can operate when selected by a user, such as by selecting an "optimize VH management" option 194 in the GUI 170 (FIG. 7A).

As just noted, algorithm 250 can operate in whole or in part in the IPG 10, and optional next step 300 contemplates usage of the algorithm 250 in the IPG 10, which can be implemented by programming algorithm 250 into the IPG's control circuitry 50. In this step 300, information defining the waveform 299—e.g., IPG programming information such as the pulse, steering, and aggregate programs described earlier (FIG. 7C)—are compiled at the external device 160 and transmitted to the IPG 10. Algorithm 250 in the IPG 10 can then analyze the waveform information, and take steps as subsequently described to allow the IPG 10 to manage VH.

However, in a preferred example, algorithm 250 operates primarily in the external device 160. This allows the external device to analyze the waveform 299, and to compile IPG programming instructions for the IPG 10 that include compliance voltage management instructions (compliance voltage adjustment instructions and/or compliance voltage measurement instructions). Operation in the external device 160 also allows a user to provide input to the algorithm 250, as described further below. Once such programming information is compiled, the external device can transmit the programming information to the IPG 10 nearer to the end of the algorithm 250 (see steps 363, 375, FIG. 12C). Algorithm 250 can comprise part of external device software 164 executable using control circuitry 166 in the external device 160 (FIG. 6).

In step 305, the algorithm 250 determines initial pulse "groups" in the waveform 299 (called "groups" to differentiate them from the "blocks" described earlier). The goal of this step is to group pulses in the waveform that should generally be similar with respect to their compliance voltage needs, such that each group will be treated similarly from a VH management standpoint. For example, and as will be shown later, each compliance voltage group of pulses will be associated with a single optimal compliance voltage value, VH(opt). It may be useful to note at this point that as the algorithm 250 runs, the defined groups can change. For example, and as shown in subsequent steps, it is possible that the certain blocks, or even certain pulses within blocks, will be consolidated into different compliance voltage groups.

Figures 13A, 13B:
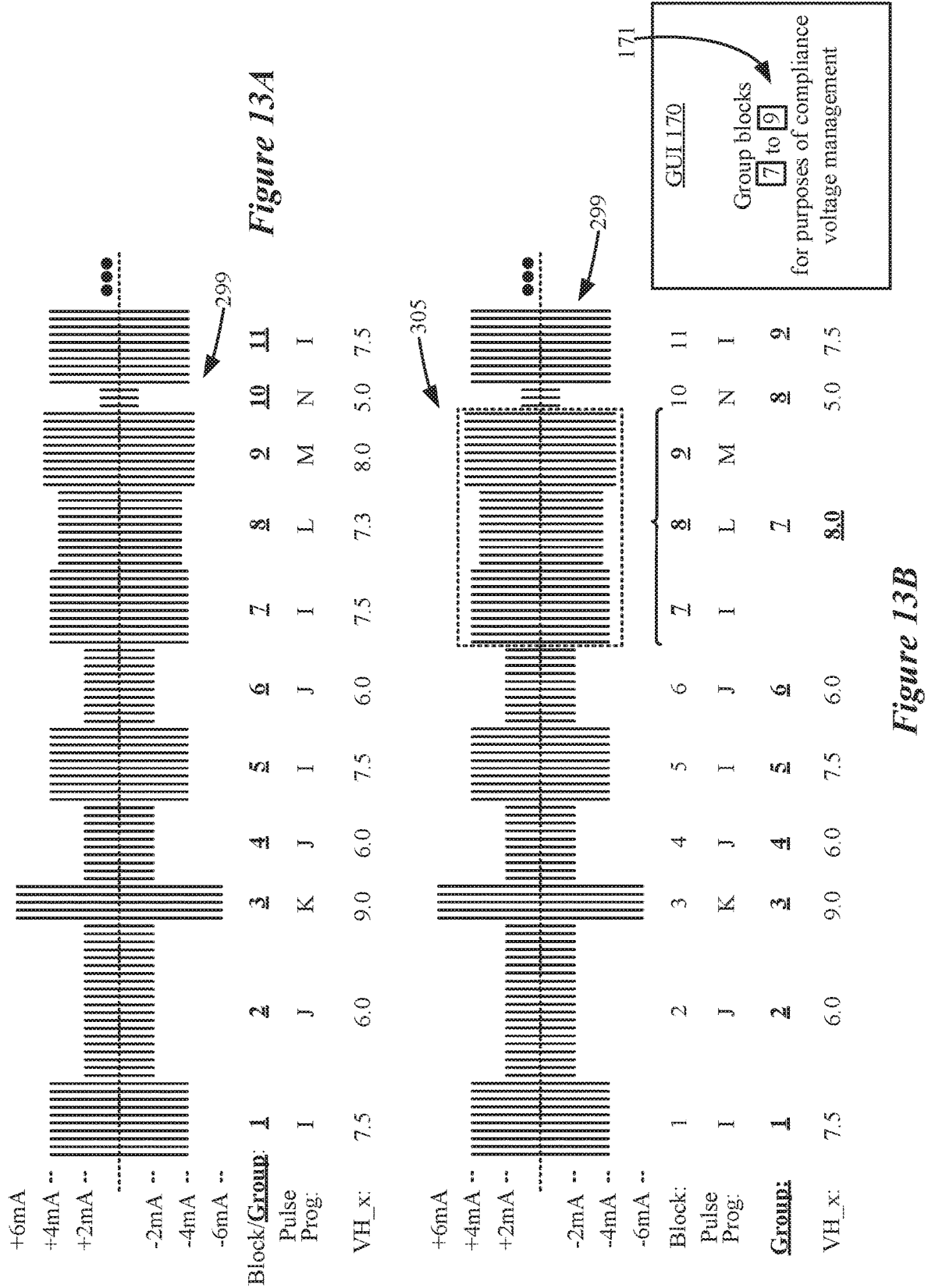

The initial determination of relevant groups of pulses at step 305 can include assessment of the pulse blocks described earlier (FIG. 7A). Groups can comprise single blocks as already defined, and this is shown in FIG. 13A, where the eleven blocks defined earlier are now treated as eleven groups for the purpose of algorithm 250 at step 305. This could be a sensible grouping, because the pulses in each block are the same, and hence would have similar compliance voltage needs, with higher amplitude or higher energy pulses requiring higher compliance voltages, and lower amplitude or lower energy pulses requiring lower compliance voltages.

Alternatively, a group can comprise a plurality of contiguous blocks. In this respect, algorithm 250 at step 305 preferably automatically determines which contiguous blocks may be combined into groups using rules within the algorithm. Such rules are directed to determining which contiguous blocks have pulses that are similar enough that it would be sensible to treat these blocks similarly from a compliance voltage standpoint. Many such automatic rules are possible. For example, one rule may be that if two contiguous blocks have pulses that vary only slightly in their maximum amplitudes or total energy (say about 10% or less), then they can be consolidated by algorithm 250 into a single group. This is logical, because blocks with pulses that are this similar should not require significantly different compliance voltage VH needs, and so it may be efficient to have the algorithm 250 treat them together. For example, notice in FIG. 13B that contiguous blocks 7, 8, and 9 have generally similar amplitudes (4.0, 3.8, and 4.2 mA respectively). Therefore, algorithm 250 at step 305 may automatically place these blocks into a single group, with the algorithm 250 eventually establishing a single compliance voltage VH applicable for this group, as will be discussed shortly. Thus, in FIG. 13B, the eleven blocks have been consolidated into nine groups, with group 7 including blocks 7-9. Subsequent steps in algorithm 250 are illustrated with respect to this example of FIG. 13B.

As alluded to, the algorithm at step 305 may consider the total energy of the pulses, or other similarities between pulses, to decide if they are to be combined into a group. In the example illustrated in FIG. 11A, all of the pulses in the different blocks vary only in their amplitudes, and have the same timings, such as the durations of their pulses phases 94a and 94b. Thus, the energy of the pulses in this example is dictated by their amplitudes, and algorithm 250 needs only in this example to assess the amplitudes of the pulses. However, different timings or pulse shapes could give rise to different pulse energies, which might cause algorithm 250 to determine groups in step 305 differently.

Suppose for example that a first block of pulses (block 1) is prescribed with an amplitude of 4 mA and pulse phases durations (94a, 94b) of 10 μs, and that a second subsequent contiguous block (block 2) is prescribed with the same amplitude of 4 mA and pulse phases durations of 25 μs. In this example, the pulses in block 2 (4 mA*25 μs) have 2.5 times the energy (4 mA*10 μs) of the pulses in block 1. The algorithm 250 may thus determine at step 305 that blocks 1 and 2 should be defined into their own unique groups 1 and 2 at step 305. This is because these pulses may have different compliance voltage needs, despite having the same amplitude. In particular, the DC blocking capacitors during the pulses of block 1 would charge to voltages (VC1, VC2) that are 2.5 times higher than when the pulses of block 2 are used (FIG. 8A). This means that the compliance voltage needed during the block 2 pulses (i.e., VH=Vp+VC1+Vrt+VC2+Vn) may be higher than when the pulses of block 1 are used.

Suppose alternatively that a first block of pulses is prescribed with an amplitude of 4 mA and pulse phases durations of 11 μs, and that a second subsequent contiguous block is prescribed with an amplitude of 5 mA and pulse phases durations of 8 μs. In this instance, the pulses in blocks 1 and 2 have similar energies (4 mA*11 μs≈5 mA*8 μs). Thus, and despite the difference in amplitude, the algorithm 250 may decide to treat combine blocks 1 and 2 into the same group at step 305. This can result because these pulses, while different, may have similar (even if not identical) compliance voltage needs, because the voltage drops across the DC blocking capacitors and the tissue (VC1, VC2) may be similar for these two types of pulses.

A number of groups can also be defined within a block, and this is particularly useful if the amplitudes of the pulses in the block have been modulated to different degrees. For example, if one of the blocks includes ramped pulses, such as block 1 in FIG. 7D, the algorithm 250 may at step 305 include smaller pulses within a first group G1; medium pulses in a second group G2; and higher pulses in a third group G3. This may be reasonable, as this splits the pulses within the block into groups that would generally have the same compliance voltage needs, with G1 requiring a lower VH, G2 requiring a medium VH, and G3 requiring a higher VH. Forming a plurality of groups within a block at step 305 could also be warranted if the pulses in the block vary with respect to some other stimulation parameter, such as duration, frequency, or shape for example. In this regard, note that it is not necessary that the pulses be grouped into blocks (FIG. 7A) before the algorithm 250 at step 305 determines groups of pulses. Algorithm 250 can instead simply analyze prescribed pulses in the waveform 299, and consolidate contiguous pulses together into a group using rules that suggest that such pulses should be treated similarly from a VH perspective. However, subsequent discussion assumes for simplicity that the waveform was initially defined by blocks of pulses as described earlier. Note that contiguous pulses may have gaps in between during which no pulses issue. For example, although not shown, the pulses between any two blocks (e.g., 1 and 2) may be separated by a dead period when no pulses issue, or there may be dead periods within a block.

The algorithm 250 may alternatively or additionally allow the user to place blocks (or pulses more generally) into groups at step 305, and FIG. 13B shows a simple option 171 in the GUI 170 for doing so. In this example, the user has noticed that pulse groups 7, 8, and 9, while different, are similar enough that it makes sense to group them for VH management purposes, and so the user has manually grouped these pulses together. In short, consolidating of pulses into groups at step 305 can occur automatically by the algorithm 250 using rules that assist in identifying pulses having similar VH requirements, or can be manually set by the user. In another example, the user at step 305 may (using a pointer for example), draw a box around individual pulses in the waveform 299 that he may wish to group for compliance voltage purposes.

Whether blocks (or pulses more generally) are grouped in step 305 automatically or manually, the GUI 170 can be updated to illustrate such groupings to the user, as shown in FIG. 13C. Here, blocks 7-9 are shown as grouped as group 7 in the GUI 170 using a group panel 196. Other blocks not yet grouped (or which may remain ungrouped) have also been indicated as comprising their own group (e.g., block 6=group 6). Grouping can be indicated in many different ways, such as by coloring the blocks or pulses with different colors, etc. The group panel 196 may include information relevant to the group, and in particular can display the optimal VH(opt) for the group, which will eventually be determined by the algorithm 250 or set by the user. (In this regard, VH(opt) for the blocks 7-9 within group 7 have now been denoted "n/a" because the compliance voltage for these blocks' is governed by the group). As will be explained later, further grouping can occur as the algorithm 250 continues to run, and GUI 170 can be updated similarly to FIG. 13C to reflect such changes.

FIG. 13D shows table 313 (FIG. 11B) updated after step 305 and shows (at this point) blocks 7-9 grouped within group 7. Next in step 307, and as also shown in FIG. 13D, a group duration is determined for each group. In instances where a group (e.g., group 1) comprises only a single previously-defined pulse block (e.g., block 1), the group duration is simply the block duration, as shown in FIG. 13D. In instances where a number of blocks (7-9) have been consolidated into a group (7), the relevant block durations are added to arrive at the group duration. Thus, notice that the group duration for group 7 comprises 300 ms, because its blocks 7, 8, and 9 each have block durations of 100 ms. Table 313 can be defined and stored in the control circuitry 166 of the external device 160 or the control circuitry 50 of the IPG 10, depending on where algrohtm 250 is implemented, and table 313 can continue to be updated as shown in later steps.

Next in step 308, an optimal compliance voltage VH (VH(opt)) is determined for each of the groups (VH_Gx), and this is preferably done only by considering only the highest amplitude (or highest energy) pulses in that group. Thus, for groups having more than one pulse amplitude, such as group 7, the highest amplitude pulses—those in block 9 (pulse program M=4.2)—are preferably considered in step 308.

There are different manners in which VH_Gx can be determined for each group in step 308. For example, and assuming that the resistance of the tissue between the relevant electrodes is known (Rt) or measured, the algorithm 250 can compute for the highest-amplitude pulses the voltage drop across the tissue (Vrt), and maximum voltage drop across the DC-blocking capacitors (VC1 and VC2). See FIG. 8A. If the optimal voltage drop across the PDAC and NDAC are known (Vp and Vn), the algorithm 250 may estimate the compliance voltage for the group by summing these voltages—i.e., VH_Gx=Vp+VC1+Vrt+VC2+Vn. However, such estimation may be inaccurate, and VH_Gx may therefore be too low to accurately form at least the highest-amplitude pulses in the group.

Figure 14A:
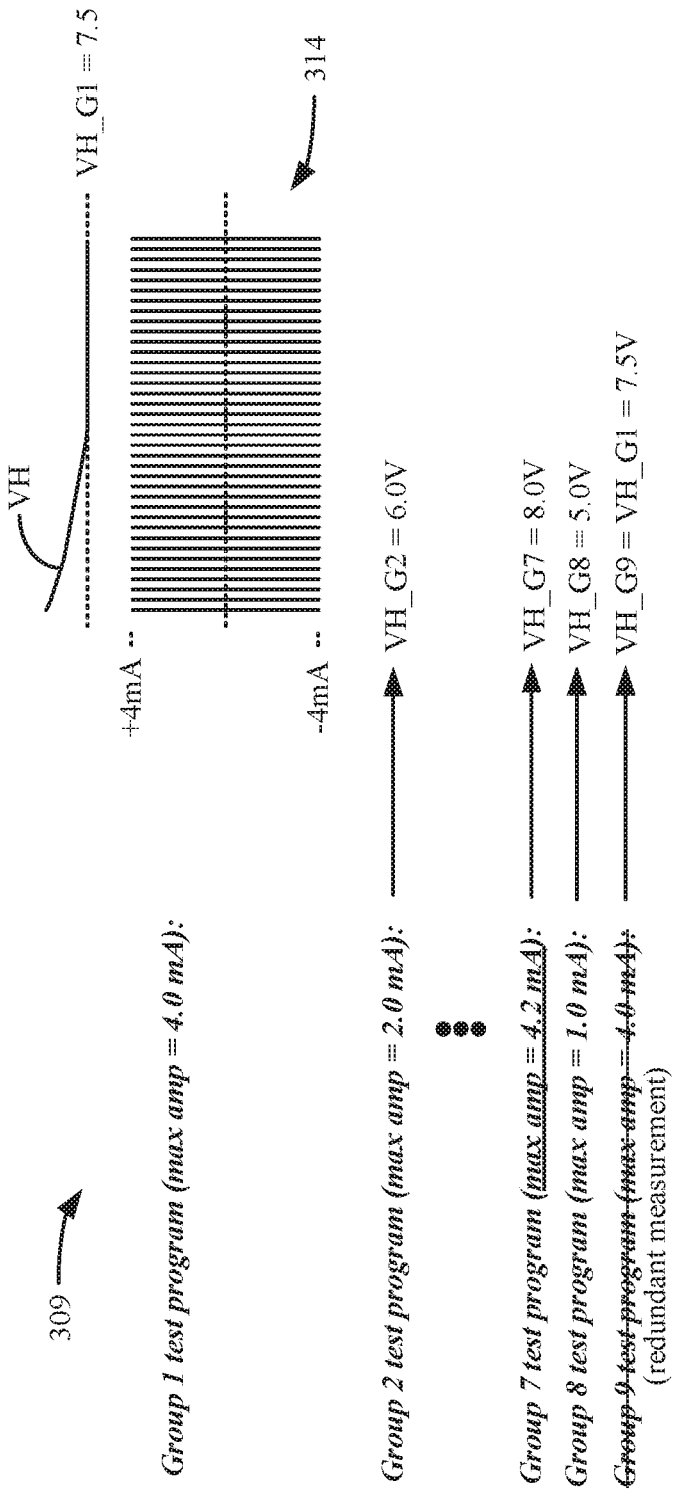

Therefore, it may instead be preferred to measure VH_Gx for each group by providing the highest-amplitude pulses in each group to the IPG 10 as test waveform 314, as described in step 309. FIG. 14A shows an example of step 309 for group 1. All of the pulses in group 1 have an amplitude of 4.0 mA (maximum amplitude), and so algorithm 250 has compiled instructions for the IPG 10 to execute a suitably large number of the pulses of group 1 as a test waveform 314 at the relevant electrodes (e.g., per steering program A; FIG. 7C). Such instruction would also preferably cause the IPG 10 to make compliance voltage measurements during the pulses, such as by setting a compliance monitoring instruction with the pulses in the text waveform. This can be accomplished by setting the compliance monitoring bit (CMB) in the pulse program used to form the test waveform 314 (see FIG. 8A). As described earlier, setting CMB causes compliance voltage measurements to be made, which results in adjusting VH until an optimal VH is determined (FIG. 8B). Such adjustment to VH is shown in FIG. 14A. Initially, VH may be set to a high level, but as the compliance voltage measurements are made, VH starts to drop, eventually reaching a steady level, which establishes VH_G1 for group 1. Note that the number of pulses in the test waveform 314 for a given group may exceed those actually used in the group, and preferably as many pulses are included as are necessary to reach a stable value for VH_Gx. Once the VH(opt) values are determined for each group, they can be telemetered back to the external device 160 (if the external device 160 is running algorithm 250), which may in turn include such values in table 313, as shown in FIG. 14C.

Notice that HV_G7 determined for group 7—which contains pulses of different amplitudes (4.0, 3.8, and 4.2 mA)—is really only optimized for the highest pulses in this group (4.2 mA). This means that when this compliance voltage VH_G7 is applied, this VH will be higher than necessary to form the lower amplitude pulses (4.0 and 3.8 mA). These lower amplitude pulses will still be adequately formed, but in a slightly power inefficient manner, as explained earlier. Still, this loss of power efficiency is compensated by simpler and more-efficient management of the compliance voltage, VH. Note also in step 309 that while it is preferable to measure VH_Gx for each group, redundant measurements do not need to be made at step 309. For example, groups 1, 5, and 9 all comprise the same highest-amplitude pulses (pulse program I, 4.0 mA). It is thus only necessary to measure VH once (e.g., VH_G1), which will comprise VH(opt) for similar groups (VH_G5, VH_G9).

Optimal compliance voltages VH(opt) for each group in step 308 may also be manually set by the user or clinician, as described in step 310. For example, and as explained earlier (FIG. 7A), GUI 170 can allow VH(opt) to be displayed or manually set for each group, as shown in FIG. 13C. It may be desired to manually set VH(opt) for a given group for any number of reasons. For example, the user or clinician may set VH(opt) for a group having very high amplitude pulses to a maximum voltage (e.g., 18V), perhaps just to be sure that these pulses have enough power to be accurately formed without loading, i.e., that the pulses can be formed at their prescribed amplitudes. Such manual setting of VH(opt) may occur even though this value may not be ideal from a power efficiency perspective (i.e., VH(opt) may be too high).

Returning to FIG. 12A, in next step 315, the rise and fall times tr and tf for VH are determined at the transitions between the groups. Remember in this regard that the VH generator 76 may be unable to adjust VH instantaneously, and rise and fall times quantify the delay that it takes the VH generator 76 to adjust VH from the optimal value VH_G(x) for one group x to the optimal value VH_G(x+1) for the next group x. The rise and fall times can be determined in different ways. For example, if the rise and fall rates Rr and Rf (FIG. 11A) are known or can be estimated, and especially if such rates are constant when adjusting VH between any two given values, algorithm 250 can compute the rise and fall times using such rates. For example, if the fall rate Rf is known to be 0.05V/ms, and if at time t1_VH must fall from VH_G1=7.5V to VH_G2=6.0V (ΔVH=1.5V), then the fall time between groups 1 and 2 can be estimated to be tf1_2=ΔVH/Rf=30 ms.

Figure 14B:
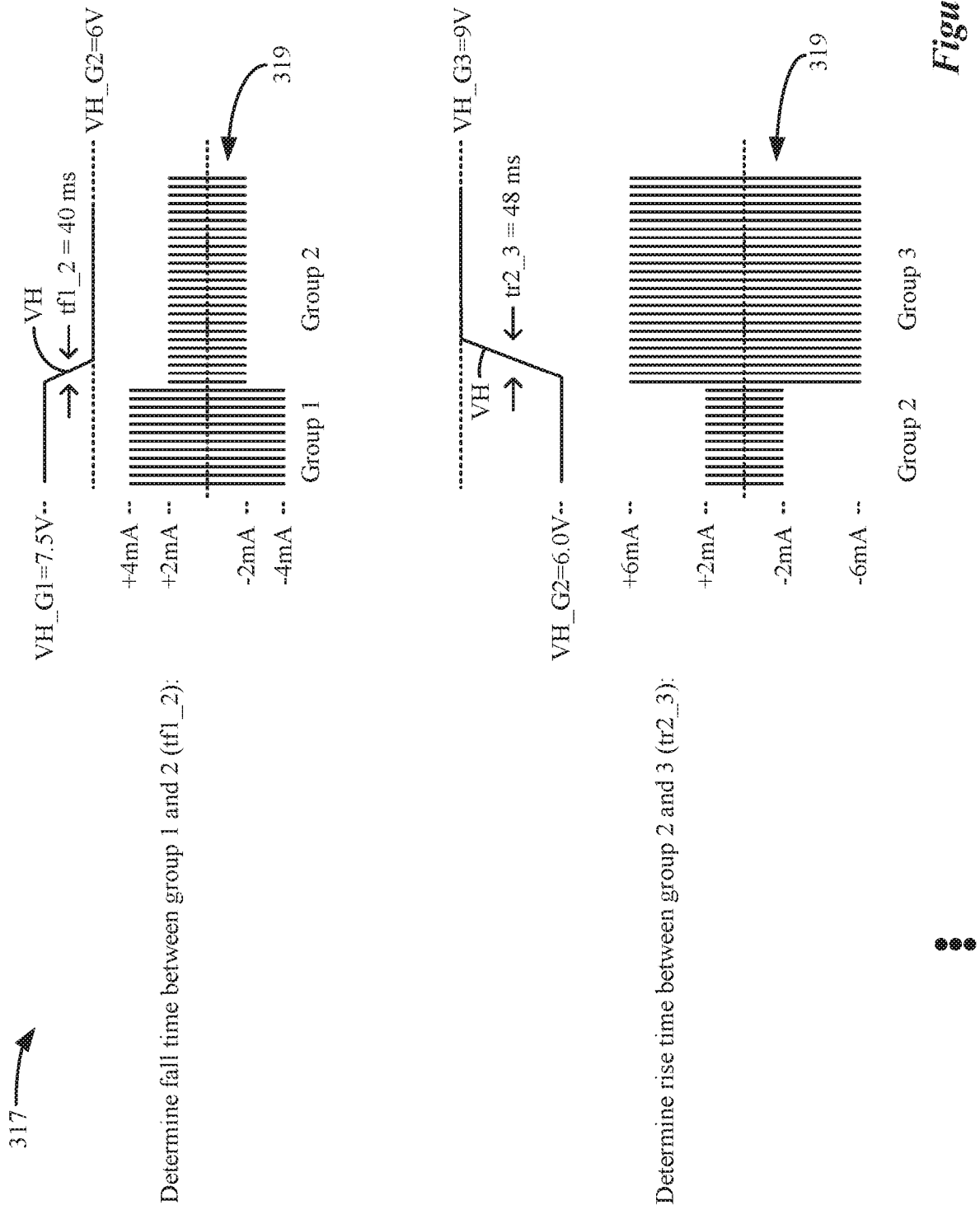
FIG. 14B shows steps in the algorithm for determining rise times and fall times of VH at transitions between the groups of pulses. The result from FIGS. 14A and 14B are illustrated in the updated table of FIG. 14C.

However, as noted earlier, the rise and fall rates may vary depending on many factors, and may depend on the starting and ending values for VH; for example the fall rate Rf from 7.5 to 6 V may not be the same as from 10.0 to 8.5V. Thus, and as described in step 317, the rise and fall times can also be measured at each group transition. This is shown in FIG. 14B, with the top illustrating the measured fall time tf1_2 in VH between groups 1 and 2, and the bottom illustrating the measured rise time tr2_3 in VH between groups 2 and 3. Again, measuring such values can comprise the use of test waveforms 319. Each test waveform 319 can essentially "mock up" the transitions that occur, including a suitable number of first pulses in group x before the transition, and a suitable number of second pulses in group x+1 after the transition. The amplitudes of the pulses in test waveform 319 may be chosen depending on whether VH will rise or fall at the transitions. For example, if VH is to fall, such as between group 1 and group 2, then the test waveform 319 can include first pulses with amplitudes equaling the highest-amplitude pulses in group 1, and can include second pulses with amplitudes equaling the lowest-amplitude pulses in group 2. Likewise, if VH is to rise, such as between group 2 and group 3, then the test waveform 319 can include first pulses with amplitudes equaling the lowest-amplitude pulses in group 2, and can include second pulses with amplitudes equaling the highest-amplitude pulses in group 3. This ensures that the fall and rise time measurements occur using the worst case pulses in each group, and thus that the fall and rise times will be determined (conservatively) with their longest possible durations.

Once the pulses in the test waveforms 319 are formed, they can be transmitted to the IPG 10, with instructions to apply such pulses at the VH(opt) values determined earlier in step 308 (e.g., VH_G1 and VH_G2). Because the values for VH for the VH generator 76 are set (e.g., VH(opt)=VH_G1 or VH_G2), there is no need to make compliance measurements during the test waveforms 319. Instead, the IPG 10 merely needs to monitor the VH voltage, and determine the rise or fall time—e.g., the time it takes for VH to fall from VH_G1 to VH_G2. This can occur by digitizing VH (see A/D 66, FIG. 2). In the example shown, it takes VH tf1_2=40 ms to fall from VH_G1=7.5V to VH_G2=6.0V; and takes VH tr2_3=48 ms to rise from VH_G2=6.0V to VH_G3=9.0V. Once the various rise and fall times are determined between each of the groups, they can be transmitted back to the external device 160 (if the external device 160 is running algorithm 250), and stored in table 313 (FIG. 14C). And as before, redundant test measurements do not need to made. For example, fall times tf1_2 and tf5_6 occur when transitioning between the same VH(opt) levels (from 7.5V to 6.0V), and so this measurement (40 ms) needs only to be made once. Note that group 1 in table 313 has no rise or fall time. This is because it is assumed that the aggregate program comprising the waveform 299 will continually loop, such that first group 1 (pulse block 1) is preceded by last group 9 (pulse block 11). See FIG. 11A. Because the pulses in these groups 1 and 9 have the same amplitude (4 mA), and the same optimal compliance voltage (VH_G1=VH_G9), no rise or fall time is associated with group 1.

Measuring VH_Gx for each of the groups (309), and measuring rise and fall times (317), may also occur using a single test waveform. However, the use of different test waveforms 314 and 319, applied to each group or transition, is illustrated for discreteness and simplicity.

As VH management algorithm 250 continues to run, groups defined by the algorithm can be further consolidated, and steps 320-327 illustrate how this can occur. In these steps, the algorithm 250 can identify where it may be impractical or impossible to manage VH_Gx for certain groups, and so such groups may be consolidated into a preceding or following group for compliance voltage management purposes.

Returning again to FIG. 12A, in next step 320, pulse groups are identified that have a value for VH(opt) that is lower that its preceding group. This is shown in FIG. 15A. Here, four groups 2, 4, 6, and 8 have been identified, that have preceding groups (1, 3, 5, and 7) with higher values for VH(opt). For example, group 2 VH(opt) is 6V, while preceding group 1's VH(opt) is 7.5V. Notice in table 313 that the groups at this step 320 can also be identified as those associated with a fall time tf. For example, group 2 is associated with fall time tf1_2, which indicates that VH(opt) lower upon entry into this group.

Next step 325 asks if the sum of the preceding fall time tf and following rise time tr associated with an identified group is greater than the group duration of that group. As seen in table 313, the group duration of identified group 2 is 200 ms, while preceding fall time into this group tf1_2 is 40 ms and the following rise time out of this group tr2_3=48 ms. Thus, the condition at step 325 isn't met, and the same is true for identified groups 4 and 6. This means that VH, if adjusted (lowered) at the transition (e.g., 1_2) preceding this group (2), will have enough time to fall during the duration into this group (2), and will eventually reach VH_G2 that is optimal for at least some portion of this group. Thus, it is reasonable for algorithm 250 to lower VH at the beginning of this group to save power in the IPG 10. This is discussed further subsequently.

Figure 15B:
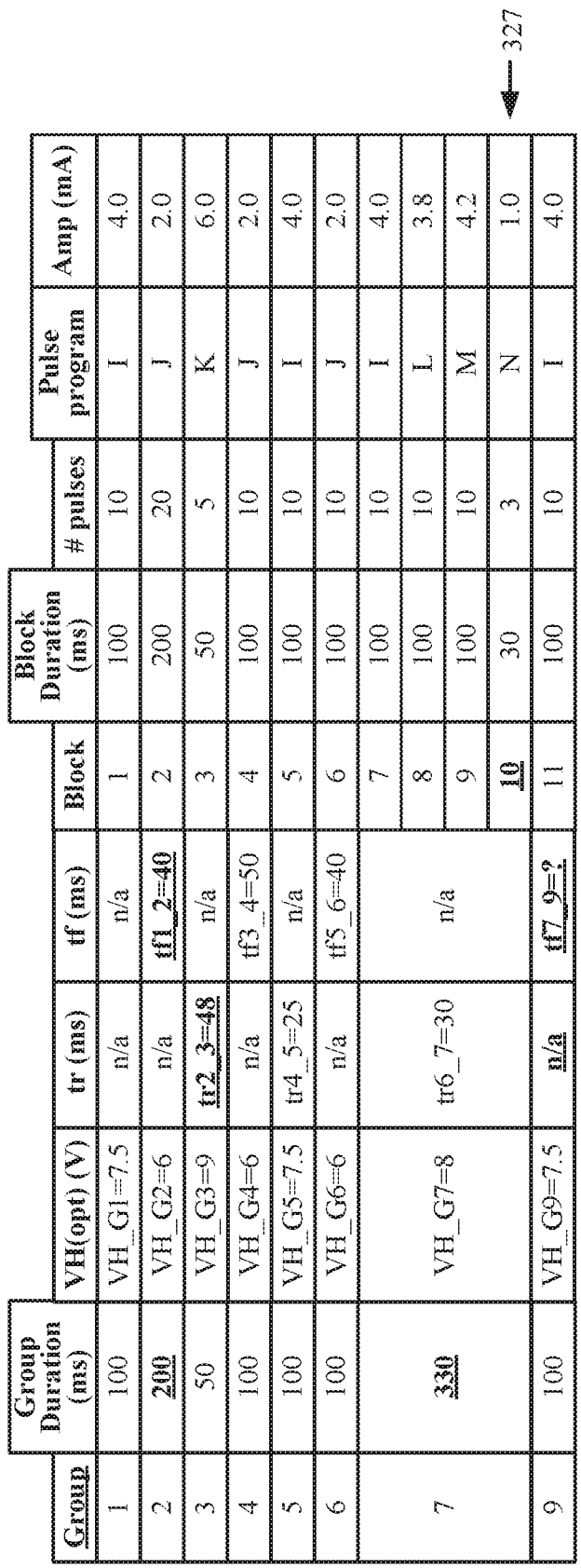
Figure 15C:
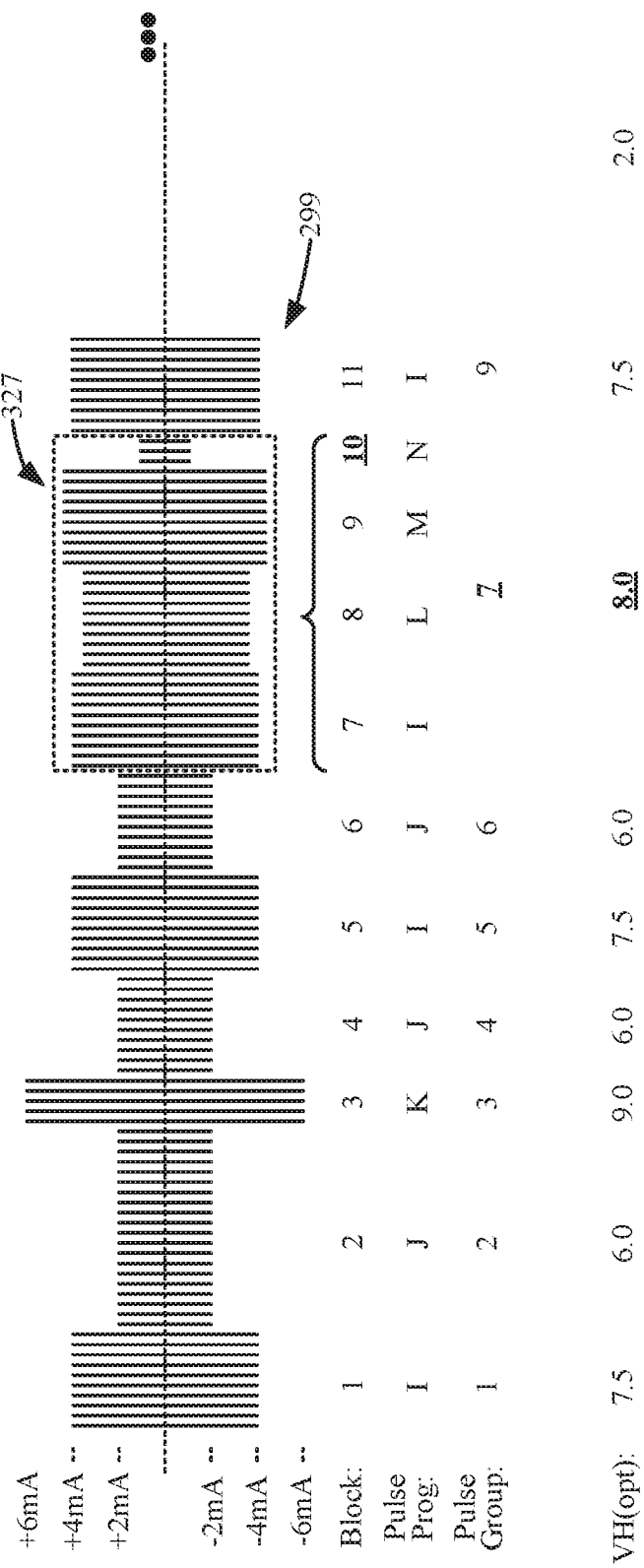

For identified group 8 however, the condition of step 325 is met: the preceding fall time tf7_8=100 ms plus the following rise time tr8_9=65 ms (165 ms) is greater than group duration 30 ms. This means that VH, if adjusted (lowered) at the transition (7_8) preceding this group (8), won't have enough time to reach the optimal compliance voltage of VH_G8 during the duration of this group (8), either because it is falling to slowly coming into this group, or rises too slowly coming out of this group, or both. In short, VH_G8 for this group will never be reached during the group 8's duration, and it therefore may be impractical or impossible for VH management algorithm 250 to manage VH for this group. Thus, to simplify VH management, and per step 327, this group can be consolidated into its preceding group for purposes of the VH management algorithm 250. This is illustrated in FIG. 15B, where it can be seen in table 313 that previous group 8 (pulse block 10) has now been placed in preceding group 7. FIG. 15C further shows the consolidation of group 8 into group 7 in the context of waveform 299.

Note that an identified group in step 320 may not be associated with a following rise time. Although not illustrated, this would occur for a group (20) that is preceded by a group (19) of higher amplitude pulses, and is followed by a group (21) of lower amplitude pulses. In this case, group 20 is associated with a fall time tf19_20 from group 19, but is associated with another fall time tf20_21 (not a rise time) going into group 21. The rise time tr for such a group would thus be 0 in step 325. In this instance, step 325 effectively inquires whether the preceding tf19_20 is greater than the group duration of group 20, meaning that VH(opt) for group 20 could never be reached. If this case, group 20 would be consolidated into group 19 (step 327).

Note that if the condition in step 325 is met, step 327 can also place the group at issue into a following group instead of a preceding group. Whether to place a group into the preceding group or following group at step 327 may depend on different factors, such as the amplitudes of the pulses in these groups, the amplitudes and group durations of the preceding and following groups, whether tf is higher than tr, and so on. For example, and referring to FIG. 15C, assume that the amplitude of the pulses in group 9 (block 11) were smaller and more on par with the amplitude of the pulses in group 8 (block 10). In this case, although not shown, it may make more sense at step 327 to consolidate group 8 into group 9, rather than to consolidate group 8 into group 7 as shown, because the compliance voltage requirements of groups 8 and 9 (having pulses with somewhat similar amplitudes) may be more similar than are the compliance voltage requirements of groups 7 and 8 (where the difference in amplitudes is greater).

Such consolidation of groups at step 327 may require updating table 313, as shown in FIG. 15B. For example, newly-consolidated group 7 (now including group 8/block 10), has a longer group duration (330 ms). Note that the optimal VH value for this newly consolidated group 7, VH_G7, will be set to the highest of the VH(opt) values for the groups that were consolidated: in this case, VH_G7 for group 7 was 8V, and VH_G8 for group 8 was 5V (FIG. 15A). Thus, in step 237, VH_G7 for the newly-consolidated group is set to the higher value (8V). Using the higher VH(opt) value ensures that all pulses in the newly-consolidated group can be adequately formed with their proper amplitudes.

Lastly, note that consolidation of groups at step 327 may affect the rise and fall times tr and tf determined earlier (step 315). For example, while it is known that VH will fall at the transition between groups 7 and 9 (because VH_G7 is higher than VH_G9), its value (tf7_9) is not yet known. However, iterative operation of the algorithm 250 may eventually determine this value, and explained next.

If groups were consolidated at step 327, it can be beneficial to re-run the algorithm 250. This is because subsequent iterations of the algorithm 250 can update the measurements as necessary, and can possibly affect even further consolidation of the groups, thus further simplifying VH management. Thus, after step 327, the algorithm 250 can return to step 305, so that the pulse groups can be (re)determined. As discussed earlier, the algorithm at step 305 can automatically use a set of rules to determine if contiguous pulses should be consolidated, and these same rules can be used to consolidate contiguous groups. For example, and as discussed and applied earlier (FIG. 13B), if two contiguous groups have pulses with maximum amplitudes or total energy that vary only slightly (say about 10% or less), then they may be combined for purposes of VH management, because the pulses in these groups have similar compliance voltage needs. Notice in FIG. 15C that this is now case for group 7 (having maximum pulse amplitudes of 4.2 mA) and next group 9 (having maximum pulse amplitudes of 4.0 mA).

Figure 16B:
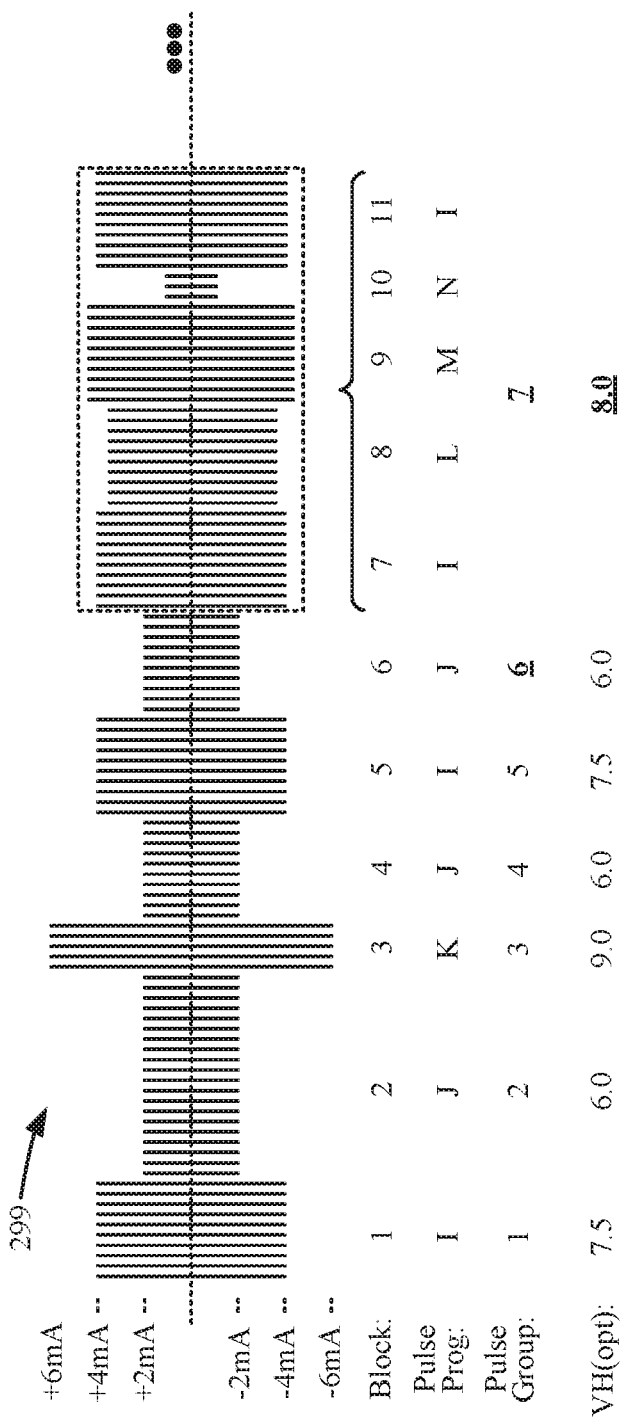

Thus, in this iteration of algorithm 250, group 9 can be consolidated into group 7 at step 305, as illustrated in FIGS. 16A and 16B. As before, such consolidation may require making further updates to table 313. For example, the group duration for group 7 is now increased from 330 ms to 430 ms (step 307), because now-consolidated group 9 (block 11) had a group duration of 100 ms. While in this iteration the optimal compliance voltage VH_G7 could be determined or measured again (steps 308/309), this may not be necessary. VH_G7=8.0V for group 7 and VH_G9=7.5V for group 9 were already determined using the highest amplitude pulses in those groups, and so VH_G7 (which now includes all pulses in groups 7-11) can be updated to the higher of VH_G7 and VH_G9 (i.e., VH_G7=8.0V) as this would be reflective of the highest-amplitude pulses.

Regrouping may affect the transitions in the groups, and so as iterative operation of the algorithm 250 continues in steps 315/317, new rise or fall times may need to be determined or measured. For example, as table 313 in FIG. 16A illustrates, group 7 has a higher optimal complicate voltage VH_G7=8.0 than does next group 1 VH_G1=7.5V (when the waveform 299 repeats). Therefore, a fall time at this transition tf7_1 (10 ms) can be determined or measured, and table 313 updated with such new information as shown. As iteration of the algorithm 250 continues, further consolidation of the groups could occur (steps 320, 325, and 327), although such further consolidation is not indicated in the depicted example. In other words, the condition at step 325 isn't met ('N'), and the VH management algorithm 250 can proceed to next step 330.

It is worth noting that the goal of steps 305-327, and possibly re-running these steps in an iterative fashion, is to analyze and process the waveform 299 into groups of pulses that have similar compliance voltage requirements that will be eventually treated similarly from a compliance voltage standpoint. However, the specific manners illustrated to define or consolidate these groups are just one example. Other rules or steps could be used to define relevant VH groups.

With the waveform 299 now analyzed and processed into different groups having similar compliance voltage requirements, subsequent steps are directed to identifying where VH(opt) must increase or decrease, and compiling IPG programming instructions accordingly (e.g., in the form of an aggregate program referencing steering and pulse programs) so that the IPG can control the VH generator 76 in a manner to produce actual values of VH that are of a sufficient magnitude to form all of the pulses in the waveform 299. Subsequent steps may further continue to adjust the compliance voltage groups determined to this point as will be explained.

Figure 17A:

Referring again to FIG. 12A, at step 330, the VH management algorithm 250 identifies groups where the optimal compliance voltages VH(opt) increases at the transition at the end of such groups. This is shown in FIG. 17A, where groups 2, 4, and 6 have been identified. Notice that these groups precede transitions with rise times, tr, in table 313.

Next, in step 335, the identified groups are split into first (a) and second (b) groups. As will be explained in subsequent steps, such splitting is useful in determining when VH(opt) should be adjusted to a higher value, so that VH can ramp up with enough time in preparation of eventually forming higher amplitude pulses. Thus, and as shown in FIG. 17B, group 2 is split into first group 2a and second group 2b. Likewise, groups 4 and 6 are split (4a and 4b; 6a and 6b), as reflected in table 313. Next in step 337, the group durations of the split groups 'a' and 'b' are set. In this example, the durations of the second groups (the 'b' groups) are set in accordance with the following rise times tr. For example, tr2_3=48 ms, and so the group duration of the group 2b is set to be at least this long, and possibly longer. Preferably, the group duration of group 2b is set to cover a discrete number of pulses, and so it is useful for the algorithm 250 to consider both the number of pulses and the pulse period. For example, all of the pulses in the illustrated example have a pulse period of 10 ms. See FIG. 7A. Therefore, the duration of group 2b is preferably set (rounded up) to 50 ms, which would cover exactly five pulses. Rise time tr4_5=25 ms, and so group 4b's duration is likewise set to 30 ms to cover three pulses. Rise time tr6_7=30 ms already covers a discrete number of pulses (again three), and so group 6b's duration is likewise set to 30 ms. Some margin may also be added to these group durations. For example, the duration of group 2b could be set to values higher than 50 ms, and thus would cover more pulses than is actually required for VH to ramp upwards.

Once the duration of the 'b' groups is set, the duration of the 'a' groups is set to the remainder the group's duration before it was split. For example, group 2, before it was split (FIG. 17A), had a group duration of 200 ms. After splitting, group 2b has a group duration of 50 ms, and so group 2a's duration is set to 150 ms (200 ms-50 ms). Similarly, the durations of groups 4a and 6a are set to 70 ms (100 ms-30 ms).

It can also be useful at this point to update the block durations and the number of pulses in each block, in a manner consistent with the group durations set for the 'a' and 'b' groups. For example, block 2 is now partially within group 2a (15 pulses) and partially within group 2b (five pulses).

Figure 17C:
Figure 17D:
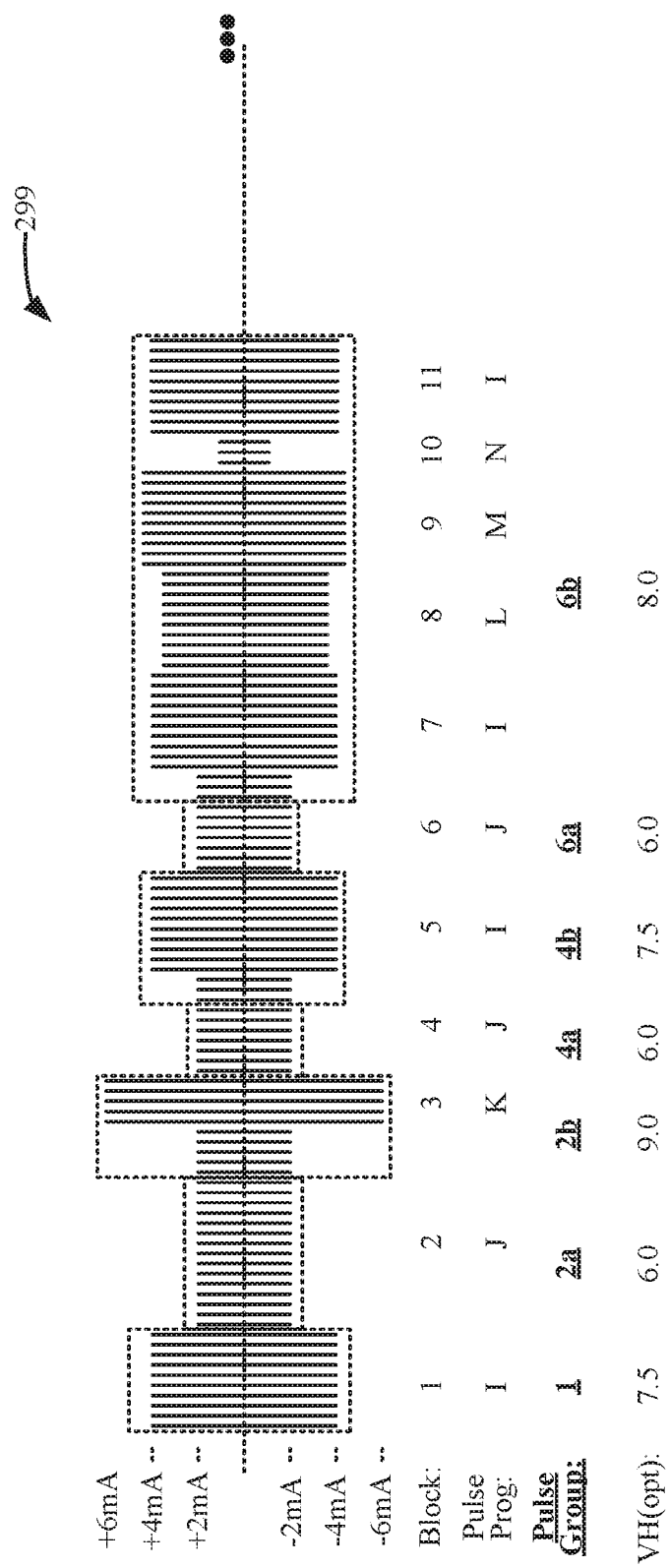

Referring to FIG. 12B, in a next step 339, the optimal compliance voltage for the second 'b' groups is set to the optimal compliance voltage VH(opt) of the next group, and such next group is consolidated into the preceding 'b' group for compliance voltage purposes, as shown in table 313 of FIG. 17C. Thus, optimal compliance voltage VH_G2b for group 2b is set to VH_G3 (9V) of group 3, and group 3 is consolidated into group 2b. In effect, this means that the last few pulses of block 2 (5 pulses) are included with the pulses in block 3 in group 2b. Ultimately the VH generator 76 will be instructed to produce VH_G2b for these pulses in blocks 2 and 3, with the expectation that VH will ramp during the last five block 2 pulses and eventually reach a value required to accurately produce the higher-amplitude (higher-energy) pulses required in block 3. VH_G4b for group 4b is likewise set to VH_G5 (7.5V) of group 5, and group 5 is consolidated into group 4b, and thus group 4b now contains the last few (3) pulses from block 4 and the pulses of block 5. VH_G6b for group 6b is likewise set to VH_G7 (8.0V) of group 7, and group 7 is consolidated into group 6b, and thus group 6b now contains the last few (3) pulses from block 6 and the pulses of blocks 7-11. The first 'a' groups retain their original values for VH(opt), as determined before the groups were split. Thus, VH_G2a=VH_G2=6V, and so on. It was previously determined that algorithm 250 should be able (based on rise and fall times) to eventually to arrive at value VH that was optimal (not to high nor too low) to form pulses during such 'a' groups. FIG. 17D shows the resulting compliance voltage groups as well as the values VH(opt) to be set during those groups, and the pulses or blocks of pulses that are included within each group.

Splitting the groups in this fashion, and setting VH(opt) as just explained, allows the VH management algorithm 250 to compile programming instructions for the IPG 10 that not only program the IPG 10 to produce the prescribed waveform 299, but that also include instructions to enable the IPG to set the compliance voltage VH(opt) produced by the VH generator 76 at appropriate times, and in particular in advance of the transition to higher-amplitude pulses when VH must be increased. In addition, the VH management algorithm 250 can additionally include compliance voltage measurement instructions with the programming instructions, as explained further below with reference to step 346 and FIGS. 20A-21X.

Figure 18:
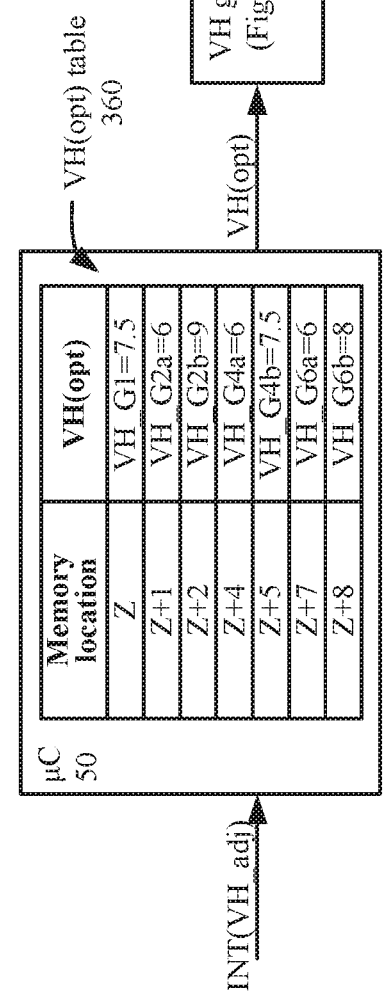
FIG. 18 shows the programming instructions for the IPG as compiled by the algorithm that will allow the IPG to form the waveform and make necessary VH adjustments in an efficient manner.

Ignoring compliance voltage measurements for the moment, FIG. 18 shows programming instructions for the IPG compiled by algorithm 250, including an aggregate program, as set forth in step 340. The aggregate program includes a number of aggregate instructions, each corresponding to a row in table 313 (FIG. 17C). Table 313 has to this point culminated all necessary information to form the aggregate instructions, including the pulse programs (which among other details sets the amplitude of the pulses), and the number of pulses (the number of "repeats" in the aggregate instructions). Table 313 could also include the steering program (which among other details selects the electrodes that will receive the pulses), but that detail has been omitted because it is assumed in the illustrated example that all pulses in waveform 299 in this example are governed by steering program A (FIG. 7C), and thus applied to electrode E1 as an anode and E2 as a cathode, as explained earlier.

At step 340 in the algorithm 250, it is helpful that the pulse programs were initially determined when the waveform was defined (see FIG. 7C). However, this is not strictly necessary, and instead pulse programs could be compiled or updated by the algorithm 250 at this time. For example, table 313 may include information (such as amplitude) necessary to allow different pulses programs. Other necessary pulse program information (e.g., number of pulse phases, amplitudes, durations, etc.) can also be included in table 313 or can be derived from the input waveform 299 itself thus enabling pulse programs to be compiled at this time.

As noted in step 342, the programming instructions can include compliance voltage adjustment instructions which instruct as to when the compliance voltage should be adjusted by the IPG, and to what values. Such compliance voltage adjustment instructions can implemented in a number of different ways. In the example shown in FIG. 18, VH(opt) can be set using an interrupt bit 20 in relevant aggregate instructions, which at the start of the execution of such aggregate instructions will send an compliance voltage adjust interrupt (INT(VH_adj)) to the IPG's control circuitry 50. This interrupt is preferably only set in aggregate instructions where VH(opt) needs to be adjusted to a different value, and thus the interrupt may not need to be set when a subsequent aggregate instruction within the same compliance voltage group requires the same VH(opt).

The first aggregate instruction (memory location Z) includes the pulses for block 1, which per table 313 references pulse program I (4 mA) and runs for 10 pulses (using steering program A). Because these pulses are associated with a new compliance voltage group (1) and a new VH(opt) value (VH_G1), this aggregate instruction includes information necessary to instruct the IPG 10 that the compliance voltage must be changed at this point. Thus, interrupt bit INT(VH_adj) is set in this aggregate instruction. The value to which VH(opt) is to be changed (VH_G1=7.5) can also be included in the aggregate instruction as well (bits 21-28), as discussed further below.

The second aggregate instruction (Z+1) includes the first 15 pulses of block 2, which per table 313 references pulse program J (2 mA). Because these pulses are associated with a new compliance voltage group (2a) and a new VH(opt) value (VH_G2a), this aggregate instruction also sets INT (VH_adj) to inform the IPG that VH(opt) should be changed, and can further include the relevant value (VH_G2a=6.0V).

The third aggregate instruction (Z+2) includes the remaining pulses in block 2, i.e., the last five pulses, and therefore continues to reference pulse program J (2 mA). However, because these pulses are associated with a new compliance voltage group (2b) and a new VH(opt) value (VH_G2b), this aggregate instruction also sets INT(VH_adj) to inform the IPG that VH(opt) should be changed, and can further include the relevant value (VH_G2b=9.0V).

The fourth aggregate instruction (Z+3) includes all pulses (10) in block 3 and references pulse program K (6 mA). These pulses are not associated with a new compliance voltage group; they are still part of group 2b. Because the necessary compliance voltage instructions for these pulses has already been set (in memory location Z+2), INT(VH-_adj) is not set, and there is no need to further include the relevant value (VH_G2b=9.0V), although this value could also be redundantly set if desired.

This repeats, with each new aggregate instructions specifying the relevant pulse program and number of pulses, and setting IN(VH_adj) or not depending on whether a new compliance voltage group has started and thus VH(opt) may need to be changed. Skipping ahead, note that the aggregate instruction at memory location Z+8 starts the last compliance voltage group (6b) in waveform 299 (before it repeats), with aggregate instructions from Z+8 and Z+13 including relevant pulses within this group. This includes the last three pulses in block 6 (pulse program J=2.0 mA), and all pulses in blocks 7-11 (pulse programs I=4.0 mA, L=3.8 mA, M=4.2 mA, N=1.0 mA, and I=4.0 mA respectively). The compliance voltage adjust interrupt (and optionally the value of VH_G6b) need only be set in aggregate instruction Z+8 because such programming also governs the aggregate instructions Z+9 to Z+13 within the compliance voltage group.

While the interrupt bit INT(VH_adj) is useful to inform the IPG's control circuitry 50 as to when VH(opt) needs to be changed at the VH generator 76, the control circuitry 50 must also know the value to which VH(opt) is to be changed. There are different manners in which the control circuitry 50 can be informed of the relevant values for VH(opt). In one example illustrated in FIG. 18, the aggregate instructions may in addition to the interrupt include the value of VH(opt), with these values sent to the control circuitry 50 at the start of such aggregate instructions. These VH(opt) values may be included in additional bits (e.g., bits 21-28) in the each aggregate instruction as shown in FIG. 18C. Note that if the aggregate instructions explicitly provide values for VH(opt)

to the control circuitry 50, it may not be necessary to redundantly provide the interrupts INT(VH_adj).

Alternatively, it may be preferable to instead have the algorithm 250 compile a VH(opt) table 360 setting forth the relevant VH(opt) values, because (as discussed further below) such a table 360 can be freely updated by the IPG 10 should compliance voltage needs change. An initial VH(opt) table 360 can be provided by the algorithm 250 to the IPG 10 along with other programming instructions, as discussed later. When a VH(opt) table 360 is used, the aggregate instructions may only need to set (or not set) the interrupt INT(VH_adj) in the relevant aggregate instructions, and VH(opt) values (bits 21-28) may not be necessary. VH(opt) table 360 may be stored in the IPG's control circuitry 50 as shown. VH(opt) table 360 is preferably responsive to the INT(VH_adj) interrupts when they issue from the relevant aggregate instructions, with VH(opt) table 360 in turn providing the proper values of VH(opt) to the VH generator 76. The VH(opt) values in table 360 may be associated with the relevant addresses for the aggregate instructions where INT(VH_adj) is set. This way, when INT(VH_adj) is received, the control circuitry 50 can determine where the aggregate program is in its execution (i.e., what memory locations Z, Z+1, etc. is being accessed), which allows VH(opt) table 360 to output the proper value to the VH generator 76. Further, once the control circuitry 50 understands where the aggregate program is in its operation, the control circuitry 50 upon receiving subsequent interrupts may simply increment a pointer to the table 360 to set the next correct value for VH(opt). As explained below, the values in VH(opt) table 360 can be updated by the IPG 10 over time as needed, such as when the tissue resistance Rt changes.

Referring again to FIG. 12B, it may be useful at step 346 to additionally include compliance voltage measurement instructions with the compiled programming instructions. Discussion of the particulars at step 346 is skipped for now, and are described later with reference to FIG. 12C and steps 355-380.

Figure 19:
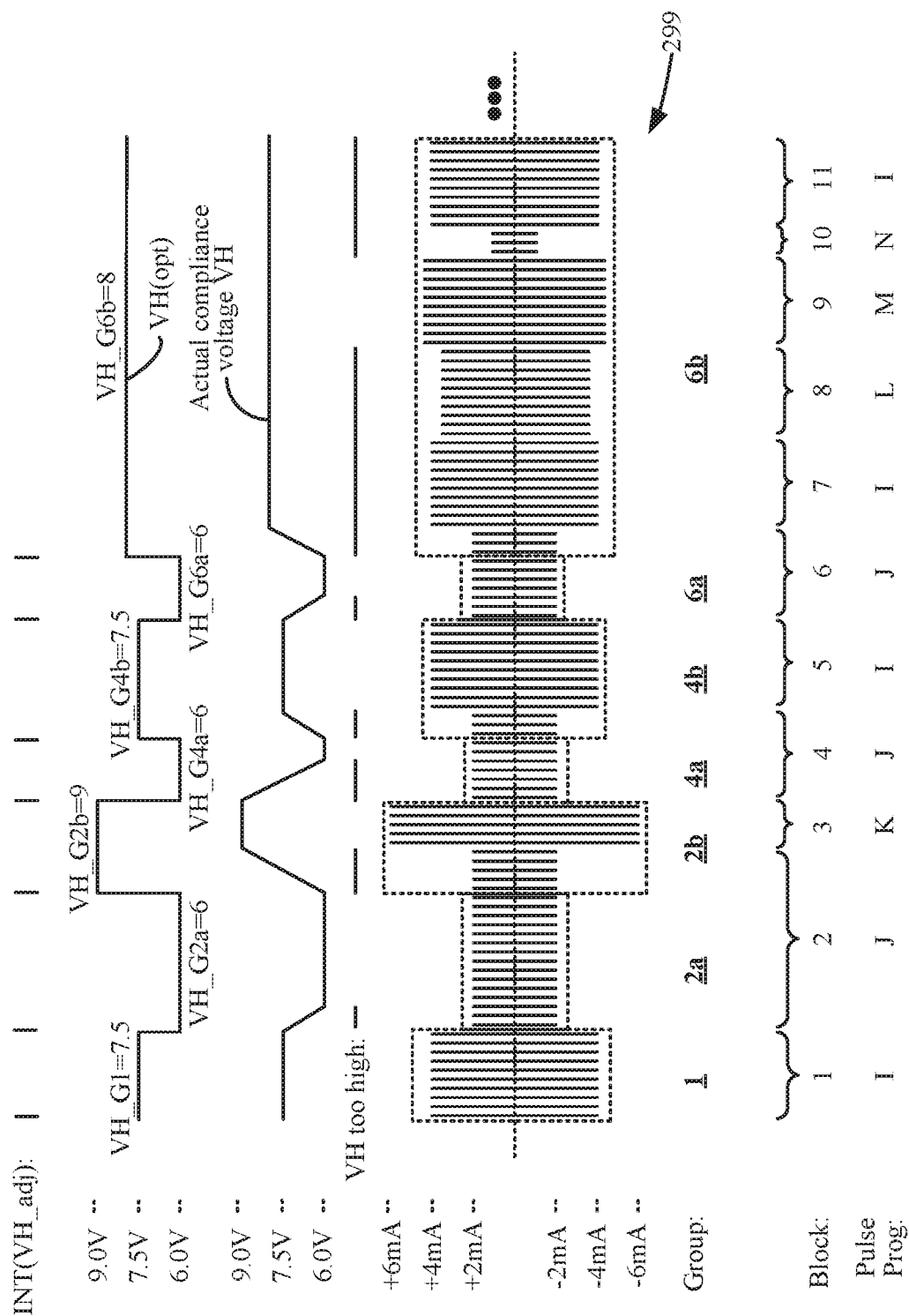
FIG. 19 shows VH as actually produced for the waveform using the programming instructions determined by the algorithm, and shows that VH is not too low, and is only minimally too high.

FIG. 19 shows the effect of VH management algorithm 250 with respect to waveform 299. The top shows VH(opt) as used to program the VH generator (as reflected in table 360 for example), and the timing of the interrupt bits INT(VH_adj) are also shown instructing when VH(opt) is to be changed at the VH generator 76. The actual compliance voltage produced is also shown, and note that it slopes upwards or downwards after every transition in VH(opt) in accordance with the rise and fall times determined earlier. Significantly, and unlike the VH management example provided earlier with respect to FIG. 11A, VH as actually produced is never too low: VH is always high enough to accurately produce all prescribed pulses without loading. This is primarily because VH is adjusted to higher values in advance of the production of higher amplitude pulses, which allows VH to have ramped to the proper value when such pulses are eventually produced. By contrast, VH is adjusted to lower values immediately when lower amplitude pulses are produced to try and save power. Further, notice that algorithm 250 greatly simplifies VH management. Even though waveform 299 comprises eleven blocks, the VH management algorithm 250 defines in this example only seven compliance voltage groups in which new values for VH(opt) must be set. This is much less burdensome than constantly trying to adjust VH(opt) for each and every block, or upon the issuance of individual pulses.

The VH management algorithm 250 does not necessarily form VH at values that are perfectly optimal from a power efficiency standpoint, although efficient implementation of the algorithm 250 does minimize power loss. VH is sometimes too high (higher than ideal) during time periods noted in FIG. 19. Many of these inefficiencies result from the reality that the VH generator 76 cannot raise or lower VH instantaneously. Thus for example, VH is too high for the initial pulses at the start of block 2 because VH is falling. VH is too high for the final pulses in group 2 because VH is increasing in preparation of being at the correct value for the higher amplitude pulses in group 3. VH is slightly too high during blocks 7, 8, and 11, because VH(opt) was set to be optimal for the highest amplitude pulses (block 9) in this compliance voltage group (6b). VH is significantly too high during block 10 in group 6b, which has significantly lower pulses amplitudes, but this only occurs for a short time and amounts to a small power loss as block 10's duration is small.

As noted above, it may be further desired to include compliance measurement instructions with the compiled programming instructions for the IPG, as provided for in step 346 (FIG. 12B). Compliance measurement instructions can, in one example, include setting a bit (CMB) in the relevant pulse programs. See FIGS. 8A-8B. Measuring the adequacy of the compliance voltage over time during generation of the waveform 299 in the IPG is prudent even though the VH management algorithm 250 to this point has determined optimal compliance voltage VH(opt) for the relevant pulse groups. This is because compliance voltage needs may change. For example, the resistance Rt of the tissue may change over time, either because of tissue scarring or because the lead migrates within the patient. Such variations may mean that VH(opt) for a given compliance voltage group of pulses, or all groups of pulses, should be raised (to form pulses accurately) or lowered (for better power efficiency). Therefore, as discussed in subsequent steps, the sufficiency of the compliance voltage VH can be measured, and the various values for VH(opt) can be adjusted as necessary. Use of VH(opt) table 360 (FIG. 18) is particularly useful, because this allows the IPG's control circuitry 50 to update VH(opt) for the various groups based on the results of the measurements without relying on instructions being sent from the external device 160.

An issue with measuring the compliance voltage in a time-varying waveform such as 299 is that it may be preferred to only measure or consider the compliance voltage at certain times. It may not be effective or necessary to measure VH on every pulse. For example, and referring again to FIG. 19, it is not useful to measure the sufficiency of VH during times when VH is changing, such as when VH is ramping up (tr) or down (tf). VH measurements taken during such times would not inform whether VH(opt) is properly set for a particular pulse group, as VH already too high by design at these times. Instead, it is preferred to measure the compliance voltage at times when VH is constant, although it may not be necessary to measure VH during every pulse when VH is constant.

There are different manners in which algorithm 250 can prescribe VH measurements in intelligent manners and during the proper times, and FIG. 12C shows a couple of different approaches. Starting first with step 355, the algorithm 250 can provide compliance voltage measurement instructions in certain programming instructions. Which programming instructions are provided with compliance voltage measurement instructions can be determined using rules in the algorithm 250, two of which are described with reference to steps 357 and 359. Rules 357 and 259, in different manners, essentially strive to measure VH during the issuance of higher-amplitude pulses.

In step 357, aggregate instructions are identified where VH(opt) rises. As shown in FIG. 20B such aggregate instructions comprise those stored at memory locations Z+2, Z+5, and Z+8, as VH(opt) increases from previous values at those points. Aggregate instructions after these (Z+3, Z+6, Z+9) are next reviewed, and if VH(opt) is not specified to change during such instructions, CMB is set in their respective pulse programs. Setting CMB for these aggregate instructions is reasonable, because pulse amplitudes suddenly increase at the start of these periods, i.e., when the pulses of blocks 3, 5, and 7 issue. It is therefore good to measure to verify that VH is high enough, and has risen fast enough, to adequately form these pulses. Note also that VH should be constant at the start of these blocks, because VH(opt) was adjusted (e.g., VH_G2$b$) in advance of the issuance of the higher amplitude pulses (e.g., block 3), and should have had time to ramp to a constant value, per earlier rise time measurements made in the algorithm (step 317). In short, step 357 instructs the IPG to measure VH during the higher amplitude pulses of blocks 3, 5, and 7, when VH is most at risk to be inadequate.

It may also be desirable to measure VH for the largest amplitude (or highest energy pulses) in a compliance voltage group having pulses with different amplitudes, as specified in step 359. Thus, CMB can also be set for block 9 (aggregate instruction Z+11), which references pulse program M=4.2 mA, which comprises the maximum amplitude pulses in compliance voltage group 6$b$. In this regard, note that pulses issued during a compliance voltage group can be measured more than once: for example, block 7 pulses are measured at the beginning of this compliance voltage group to ensure that VH has ramped properly (per step 357), and block 9 pulses are also measured to ensure that VH is high enough to form these highest-amplitude pulses.

It may be necessary for the VH management algorithm 250 to define new pulse programs at this point so that CMB can be properly set when desired. For example, notice in FIG. 20B that CMB is set during aggregate instructions Z+6 and Z+9, which references pulse program I to form blocks 5 and 7. Aggregate instructions Z and Z+13 also reference aggregate program I to form blocks 1 and 11, but it is not necessary to CBM in these instructions. The algorithm 250 may therefore create two versions of this pulse program: I to be used during blocks 5 and 7 in which CMB is not set, and I' to be used during blocks 1 and 11 in which CMB is not set, as shown in the aggregate program of FIG. 20B. CMB is also set during aggregate instruction Z+3, which references pulse program K, and during aggregate instructions Z+11, which references pulse program M. Because these pulses programs K and M aren't referenced in any other instructions (and in particular are not referenced in instructions where CMB should not be set), CMB can simply be set in these pulses programs without the need to compile additional pulses programs K' and M'.

Figure 20A:
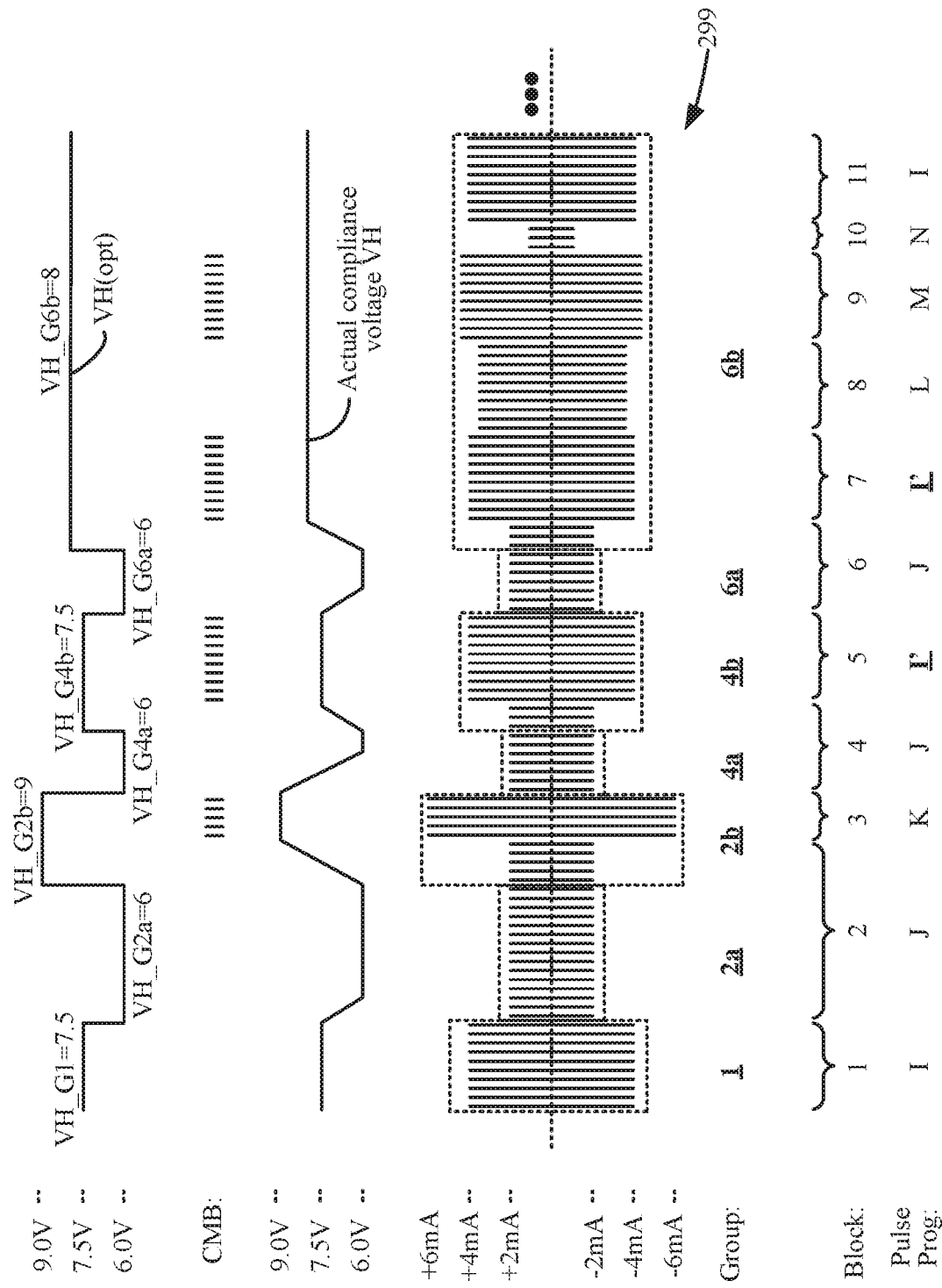

FIG. 20A shows the effect of setting CMB in the pulse programs of selected aggregate instructions in the aggregate program of FIG. 20B, and shows when (during which pulses) the IPG will be instructed to measure the compliance voltage. Notice in this example that such measurements are taken sparingly, which simplifies operation, and only during periods when VH should be constant.

At this point, IPG programming instructions are complete and include the necessary information to the IPG 10 to produce the waveform 299 (the aggregate program, and the pulse and steering programs it references), to adjust VH when needed (e.g., by setting INT(VH_adj) and compiling VH(opt) table 360), and to measure VH (e.g., by setting CMB in relevant pulses programs and aggregate instructions). Assuming that VH management algorithm 250 has been operating in the external device 160, such programming instructions can then be transmitted to the IPG 10 in step 363 for storage and execution.

When the IPG 10 executes the aggregate program (step 365), compliance voltage measurements will be taken as dictated by the pulse programs referenced in the various aggregate instructions, which allows relevant values for VH(opt) to be raised or lowered as needed. Again by way of review (FIGS. 8A and 8B), and as shown in FIG. 20C, the relevant electrode nodes will be assessed and compared to various thresholds (e.g., Vp(ref)L, Vp(ref)H, Vn(ref)L, Vn(ref)H) in response to the CMB instructions to determine if they are high or low. VH measure algorithm 222 in the IPG's compliance logic 220 will issue compliance voltage measure interrupts, INT(VH_meas), to the IPG's control circuitry 50, which in turn can determine whether VH(opt) should be raised or lowered during the relevant compliance voltage groups. In this regard, remember that the control circuitry 50 can know where the aggregate program is in its execution, which informs to which VH(opt) values in table 360 might require adjustment.

For example, in FIG. 20C, the control circuitry 50 has determined using the interrupts INT(VH_meas) that VH_G2$b$ governing compliance voltage group 2$b$ is too low. In effect, the control circuitry 50 has determined that VH is too low during the pulses of blocks 3 within group 2$b$, where CMB is set and VH is actually measured (see, e.g., FIG. 20A) during this group. The control circuitry 50 has therefore raised VH_G2$b$ from 9V to 9.3V, which it affects in this example by increasing this value in the VH(opt) table 360. The need to raise VH_G2$b$ could result because the resistance between the relevant electrodes (E1 to E2) has increased for whatever reason. Note that this new value for VH_G2$b$ may be arrived at gradually. Thus, the IPG may execute waveform 299 a number of times, and take several VH measurements during block 3 and vary VH_G2$b$ until such time as the VH measure algorithm 222 in the IPG's compliance logic 220 is satisfied that VH_G2$b$ is neither too high nor too low. The control circuitry 50 has also determined in FIG. 20C that VH_G6$b$ governing group 6$b$ is too low, and should be raised (from 8.0V to 8.3V). This could result because VH is too low when VH is measured during either of blocks 7 or 9 within group 6$b$.

Note that if the tissue resistance increases, it might be expected that all VH(opt) values in table 360 would need to be increased. Likewise, if the tissue resistance decreases, it might be expected that all VH(opt) values would need to be decreased. However, it is not necessarily true that all VH(opt) values should be adjusted in unison. As explained earlier, the VH generator 76 may only be able to produce VH as multiples of Vbat, and because there are a limited number of gain values the VH generator 76 can produce (FIGS. 10A and 10B), the values for VH(opt) may have different margins: i.e., some VH(opt) values may be slightly higher than optimal, while others may be significantly higher than optimal. If the tissue resistance increases for example, some VH(opt) values having smaller margins may need to be increased, while others having larger margins will not.

Note during step 365 that the control circuitry 50 may decide that VH(opt) is too high during certain groups, and thus that VH(opt) can be also lowered, perhaps because tissue resistance has decreased. Making such an adjustment at step 365 is preferred to save power in the IPG 10.

Note in the simple example of FIGS. 20A-20C that compliance measurement instructions (e.g., CMB) were only set for the highest amplitude pulses—i.e., during block 3 of group 2*b*, block 5 of group 4*b*, and blocks 7 and 9 of group 6*b*. This allows only VH(opt) values corresponding to these higher-amplitude compliance voltage groups (VH_G2*b*, VH_G4*b* and VH_G6*b*) to be adjusted. However, it may be desirable to measure VH and adjust V(opt) values for all compliance voltage groups, including lower-amplitude compliance voltage groups (VH_1, VH_G2*a*, VH_G4*a*, VH_G6*a*), and FIGS. 20D and 20E show an example.

Figure 20D:
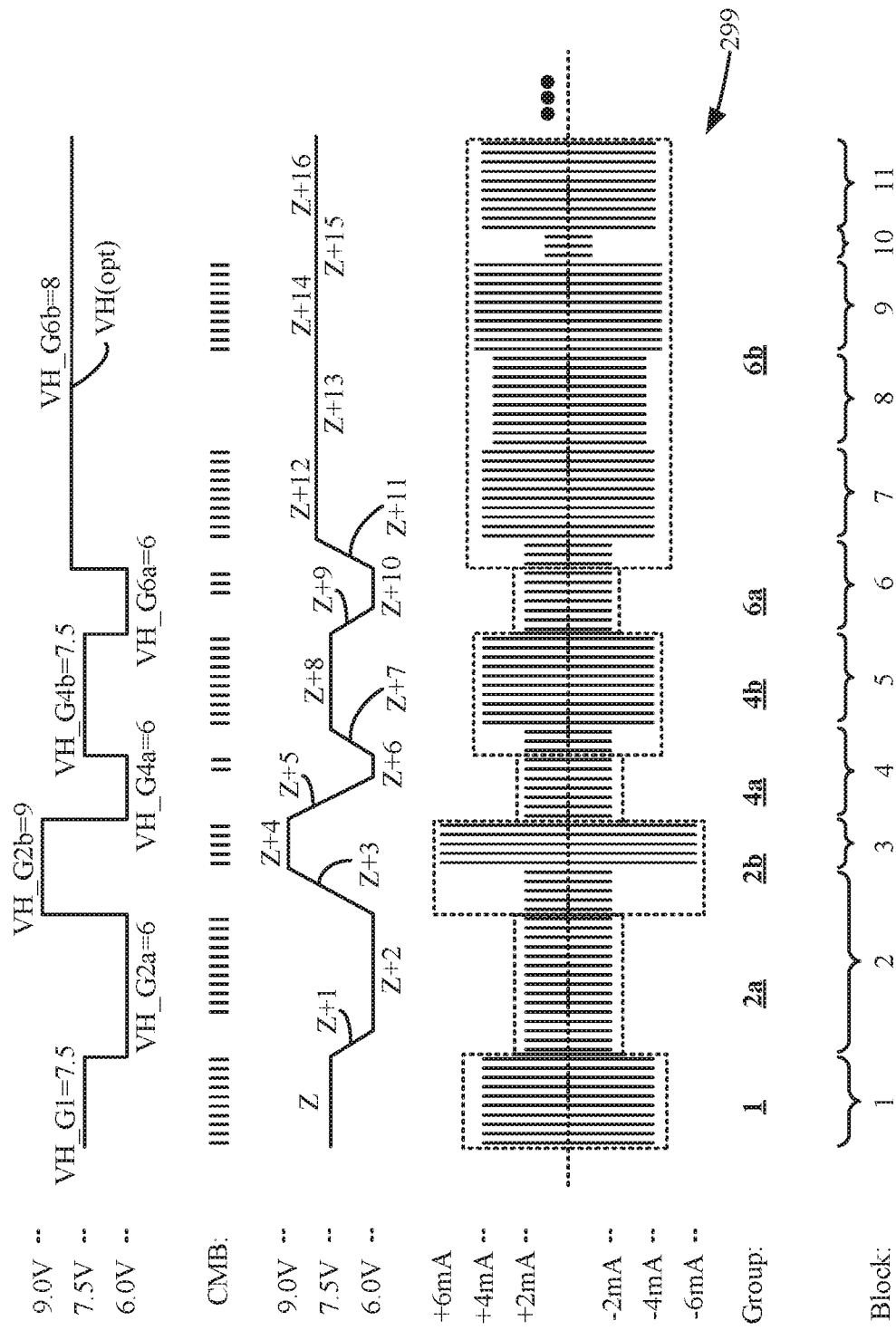

In FIG. 20D, CMB is set to make measurements whenever VH is constant, which allows VH to be measured during all of the compliance voltage groups and thus allows all values for VH(opt) to be adjusted (e.g., in table 360). FIG. 20E shows an example of an aggregate program that enables such measurements by setting CMB at times when VH is expected to be constant. The details are skipped here, but essentially the expected rise and fall times at the various VH transitions as measured earlier (step 315) are considered to understand time periods where VH should be constant, and to form aggregate instructions accordingly in which CMB is set. This can require adding additional aggregate instruction to the aggregate program. For example, compliance voltage group 2*a* has been split to comprise two aggregate instructions: one (Z+1) that occurs when VH is expected to be falling (see FIG. 15A, tf1_2=40 ms) covering 4 pulses of block 2, and another (Z+2) that occurs when VH is expected to be constant, covering 11 pulses of group 2 (before VH starts to rise at Z+3). CMB is not set during instructions Z+1 and is set during instruction Z+2, as shown FIG. 20E and in the waveform of FIG. 20D. (Note in FIG. 20D that the addresses of the aggregate instructions of the aggregate program of FIG. 20E have been added to the VH waveform to ease understanding). Compliance voltage groups 4*a* and 6*a* have likewise been similarly split, in accordance with fall times tf3_4 and tf5_6 (FIG. 15A), to allow CBM to be set during periods when VH is constant, and not set when VH is falling. Note that this may require, as occurred in FIG. 20B, defining different pulse programs that produce the same pulses, but where CMB is set (e.g., J') or not set (e.g., J).

FIG. 12C shows in steps 370-380 another example of how compliance voltage measurements can be taken at appropriate times during the waveform 299 and used to adjust the VH(opt) values. Starting with step 370, compliance voltage measurement instructions are provided in all pulse programs. That is, CBM is set in all of the pulses programs referenced in the various aggregate instructions, as shown in FIG. 21B. This effectively instructs the compliance logic 220 in the IPG 10 to make compliance voltage measurements on every pulse. Alternatively, the compliance logic 220 can be independently programmed to always measure the compliance voltage on every pulse as an operation mode selection, without the need to specify such measurements in the IPG's programming instructions.

Figure 21A:
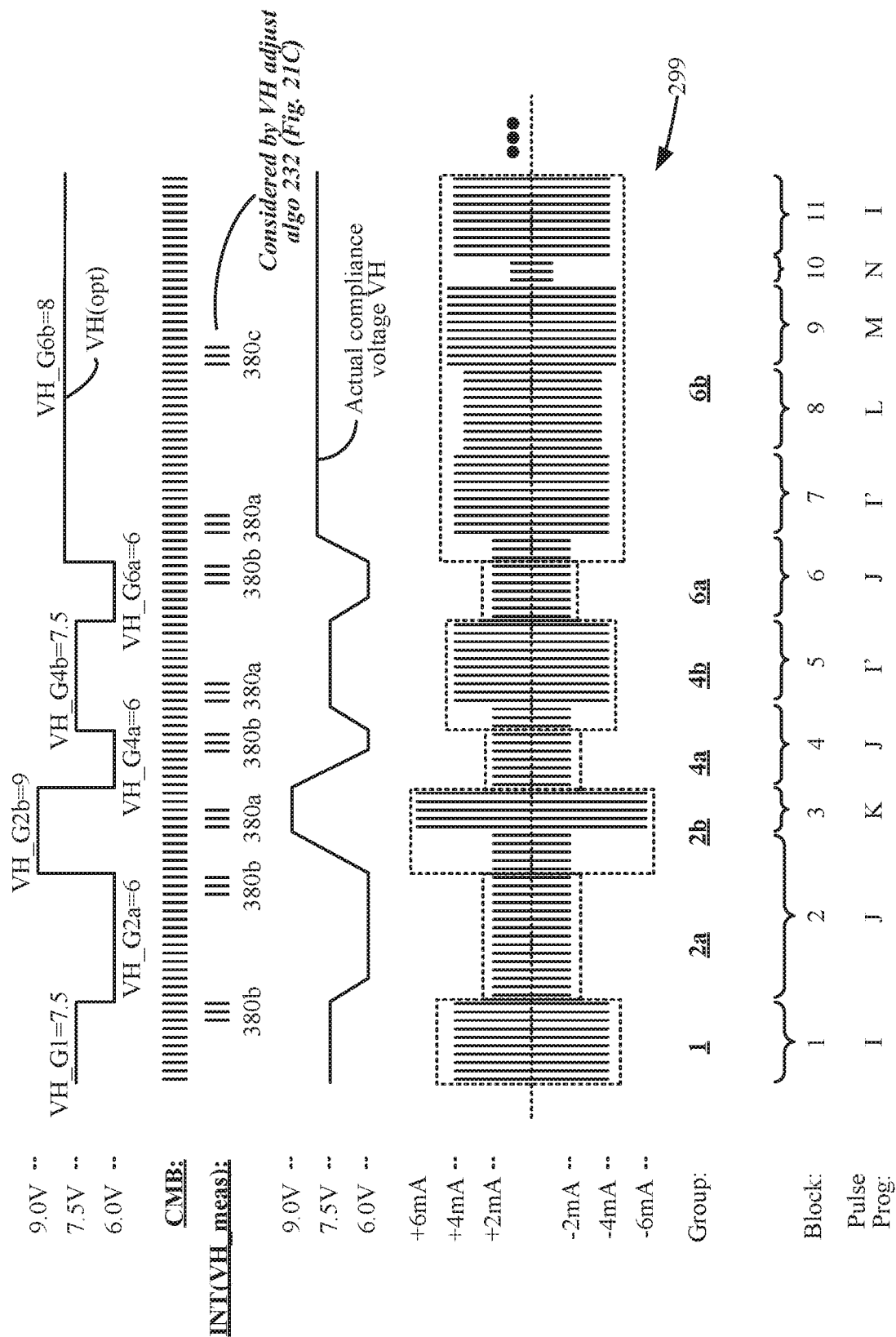
Figure 21C:
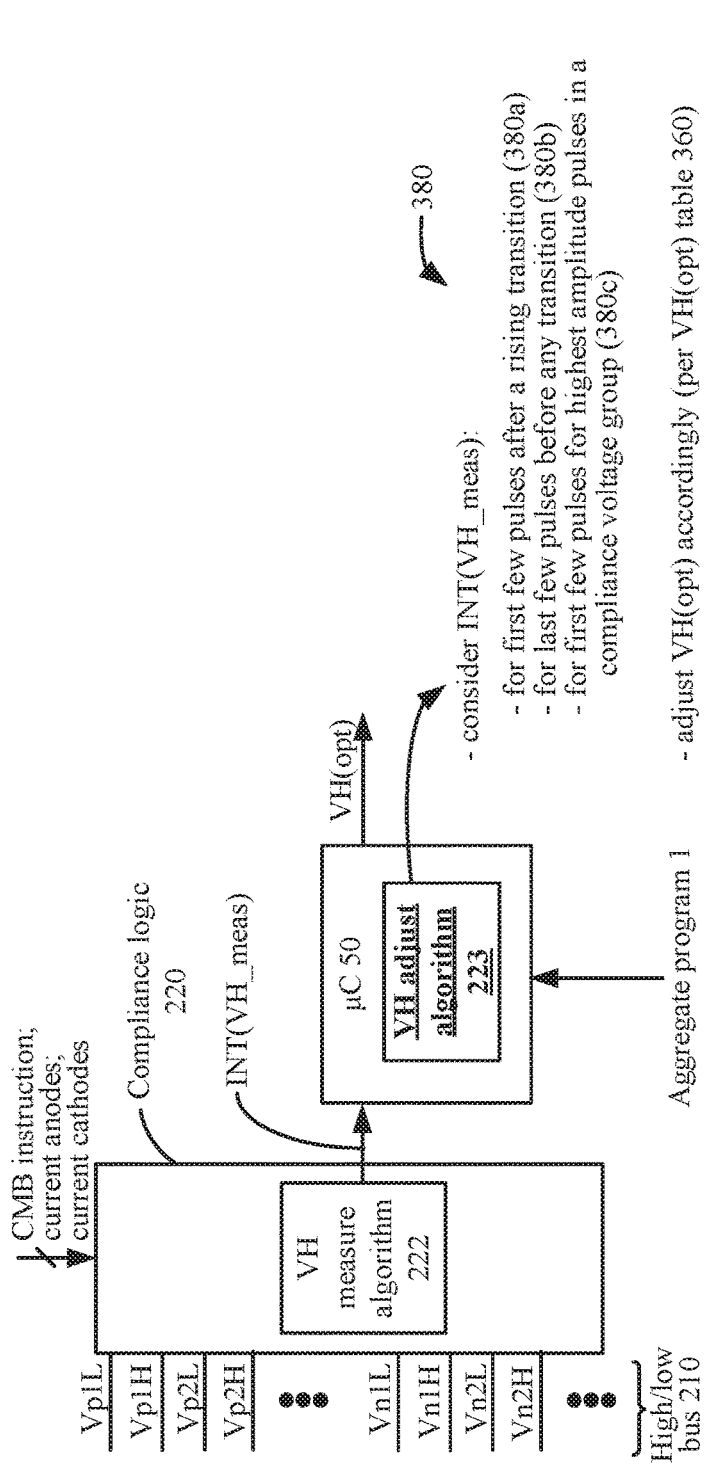

In next step 373, a VH adjust algorithm 223 (FIG. 21C) is compiled or enabled. As shown in FIG. 21C, the VH adjust algorithm 223 can operate in the IPG's control circuitry 50, and functions to consider only relevant ones of the compliance voltage measurements, i.e., to consider INT (VH_meas) only for certain pulses. In other words, even though the IPG is instructed to always measure the compliance voltage (step 270), the VH adjust algorithm 223 will only consider certain of those measurements. In effect then, the VH adjust algorithm 233 dictates the timing of when compliance voltage measurements are made.

VH adjust algorithm 223 may programmed with one or more rules 380 to assist in deciding which compliance voltage measurements to consider, as shown in FIG. 21C. Preferably such rules 380 are set to only consider compliance voltage measurements taken during pulses in which VH is expected to be constant, and not rising or falling. Rules 380 may be applied based on an analysis of the waveform 299, or more specifically the aggregate program (e.g., FIG. 18) defining the waveform, which as described earlier informs as to when VH(opt) is to be changed, and during which pulses VH should be constant or changing.

In one example, rules 380 may cause VH adjust algorithm 223 to consider all compliance voltage measurements whenever VH is constant. In effect, such an approach mimics the results discussed earlier with respect to FIGS. 20D and 20E. This may be a reasonable rule to apply when the waveform 299 is first executed at the IPG 10, as this will allow the values for VH(opt) to be adjusted quickly and thoroughly. However, once appropriate VH(opt) values have been determined, different rules 380 may be applied by VH adjust algorithm 223 to consider fewer measurements, or consider measurements less frequently.

For example, rule 380*a* specifies that the VH adjust algorithm 223 should consider compliance voltage measurements (as reflected in INT(VH_meas)) for one or more pulses after the occurrence of a rising transition. Rule 380*a* may consider measurements taken for three such pulses for example, as this would allow the VH adjust algorithm 223 to average such results. Consideration of such measurements pursuant to rule 380*a* is shown in FIG. 21A. Rule 380*a* is useful as it allows VH to be measured, and VH(opt) levels adjusted, for higher-amplitude pulses. Again, the VH adjust algorithm 223 can understand which pulses occur after a rising transition by its understanding of the IPG's programming, as explained above. For example, the VH adjust algorithm 223 can know via the aggregate program that when VH is increased for compliance voltage group 2*b* (Z+2), it should consider the first few pulses at the start of the next aggregate instructions (Z+3) within this group. If consideration of these measurements reveals that VH is too low, VH adjust algorithm 223 can increase VH_G2*b*; if too high, algorithm 223 can decrease VH_G2*b*.

Rule 380*b* is similar, but instructs the VH adjust algorithm 223 to consider one or more last pulses before any transition, and consideration of such measurements pursuant to rule 380*b* are shown in FIG. 21A. Rule 380*a* is useful as is allows VH to be measured, and VH(opt) levels adjusted, for lower-amplitude pulses, or whenever VH(opt) is set to decrease. For example, consideration of compliance voltage measurements for the last few pulses in compliance voltage group 2*a* can allow the VH adjust algorithm 223 to determine whether VH_G2*a* requires adjustment. Note that reviewing pulses just before a VH transition may be sensible as it would be more likely that VH is stable at such times.

Rule 380*c* instructs the VH adjust algorithm 223 to consider one or more pulses for the highest-amplitude pulses within a compliance voltage group. Rule 380*c* is useful to ensure that such highest-amplitude pulses (e.g., block 9 in group 6*b*) are being accurately formed, and to allow VH_G6*b* to be adjusted up or down if necessary.

VH adjust algorithm 223 and its associated rules 380 can be compiled by the VH algorithm 250, or the VH management algorithm 250 can enable the use of the VH adjustment algorithm 223 in the IPG if it has already determined.

At this point, IPG programming instructions are complete and include the necessary information to the IPG 10 to produce the waveform 299 (the aggregate program, and the pulse and steering programs it references), to adjust VH when needed (e.g., by setting INT(VH_adj) and compiling VH(opt) table 360), and to measure VH (e.g using VH adjust algorithm 223). Assuming that VH management algorithm 250 has been operating in the external device 160, such programming instructions can then be transmitted to the IPG 10 in step 375 for storage and execution. When the IPG 10 executes the aggregate program (step 380), compliance voltage measurements will be taken as dictated by VH adjust algorithm 223, which allows relevant values for VH(opt) to be raised or lowered as needed.

While VH management algorithm 250 can specify the taking of compliance voltage measurements in various manners (e.g., steps 355 to 380), note that such measurements, and resulting adjustments to the VH(opt) levels, may not need to occur continuously as the IPG. Instead, VH measurement and adjustment in the IPG 10 can occur on a schedule, such as every minute or so. This can be desirable to simplify IPG operation, and may be reasonable because while compliance voltage needs may change over time, it may not be necessary to change the compliance voltage instantly.

Because the compliance voltage can be measured (FIGS. 20A-21C) with such measurements used to update the optimal compliance voltage values VH(opt) for each compliance voltage group, it is not necessarily required that values for the VH(opt) variables are initially determined for the waveform 299. For example, and referring to FIG. 22, the algorithm 250 can provide an initial VH(opt) table 360 that specifies when VH(opt) needs to be changed (during particular aggregate instructions Z, Z+1, etc.), but which otherwise does not provide pre-determined particular optimal voltage values. As the waveform 299 is executed and compliance voltage measurements are taken, these optimal values can eventually be determined for the waveform 299 and populated in VH(opt) table 360, as shown in FIG. 22, and thereafter updated in the future as warranted. Because pre-determined optimal voltages are initially not known, the VH generator 76 may initially set to a maximum voltage (e.g., VH(opt)=18V) for each of the compliance voltage groups VH_Gx. Then as the waveform 299 is executed and compliance voltage measurements are taken, the compliance voltage can be lowered until optimal values for each VH_Gx are determined, stored in VH(opt) table 360, and thereafter such values are used to control programming of the VH generator 76.

FIGS. 23A-23E shows further details concerning how algorithm 250 can group pulses into different compliance groups and automate compliance voltage measurements with each compliance voltage group, depending on the stimulation parameters used for the pulses.

Figure 23A:
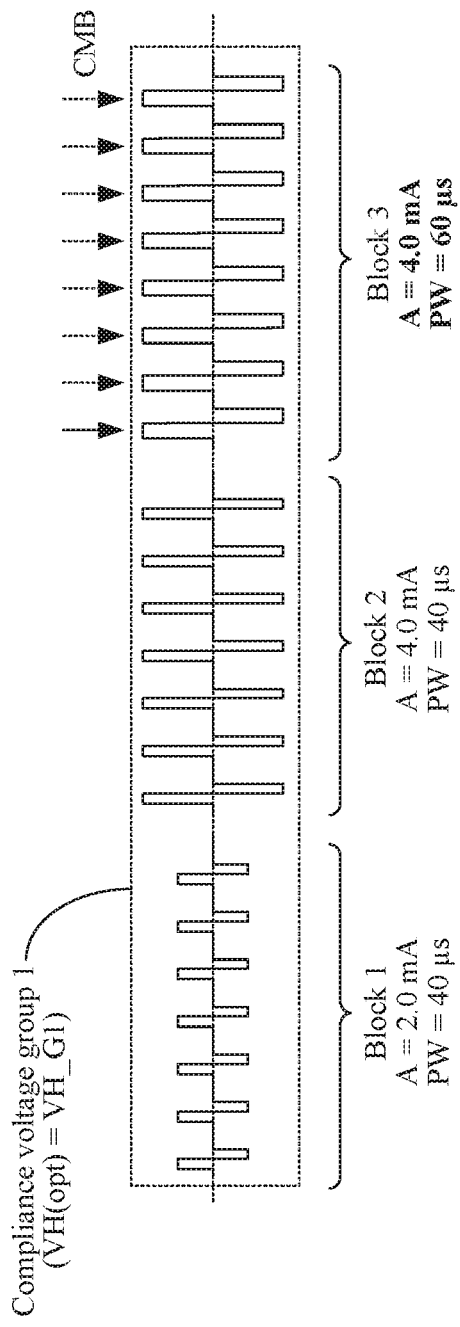
FIGS. 23A-23E shows different examples of how the algorithm can group blocks of pulses, and decide when compliance voltage measurement should be made within each group.

In FIG. 23A, a single compliance voltage group 1 has been defined (elsewhere in the algorithm 250) as including the pulses of blocks 1, 2, and 3, which group will be governed by compliance voltage variable VH_G1. The value of this variable may be known or specified in advance, but preferably its value will eventually set or adjusted in the IPG 10 using compliance voltage measurements. The algorithm 250 assesses the stimulation parameters for the pulses in this group to determine which pulses will require the highest compliance voltage, and hence which pulses should be measured to govern the value of VH_G1. In this example, such "worst case" pulses are those in block 3, because they have the highest energy, i.e., the highest amplitudes and pulse widths. Compliance voltage measurement instructions (e.g., setting CBM) are thus provided for during at least some of the pulses in this block 3. Preferably, CBM is set for at least the first pulse in block 3 to allow for immediate verification and adjustment of VH_G1, although CBM could also be set for additional pulses in block 3, or for all of its pulses.

Figure 23B:
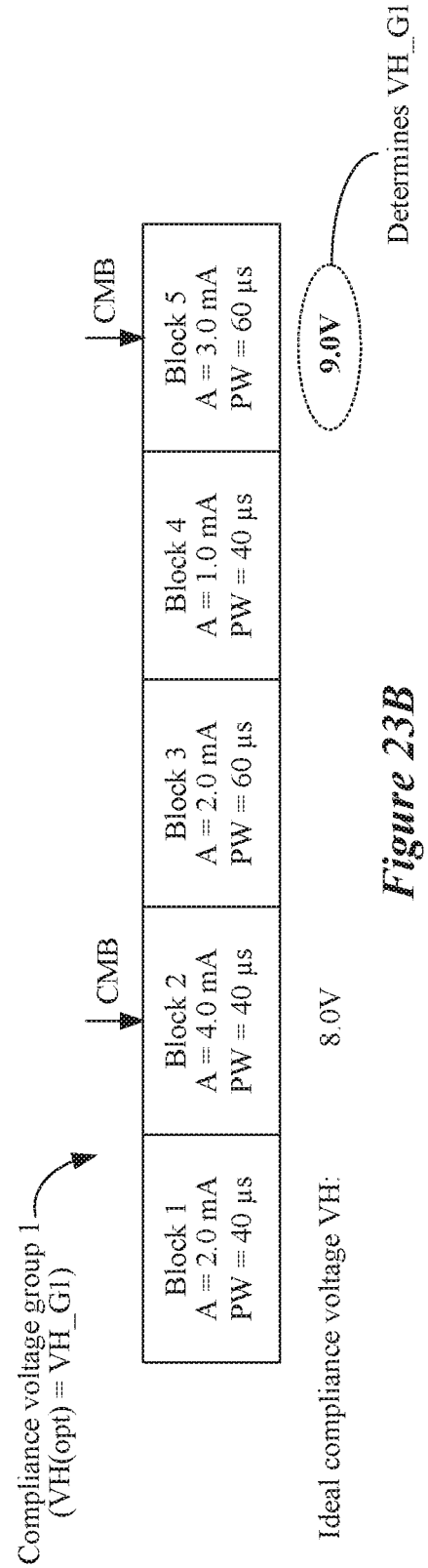

The algorithm 250 may not be able to readily determine a single block within a compliance voltage group that should be measured and used to govern the compliance voltage for that block, as illustrated in FIG. 23B. in this example, a compliance voltage group is defined having five blocks. Blocks 1, 2, and 4 have pulse widths of 40 microseconds, and for these blocks the algorithm 250 can conclude that block 2 would be a worst case because the pulses in this block have the highest amplitude (energy) (4.0 mA). Blocks 3 and 5 by contrast have pulse widths of 60 microseconds, and for these blocks the algorithm 250 can conclude that block 3 would be a worst case because the pulses in this block have the highest amplitude (energy) (3.0 mA). However, it may not be possible for the algorithm 250 to determine the worst case as between blocks 2 and 5. Comparing these two blocks, block 2 has a higher amplitude (4.0 mA) and a smaller pulse width (40 μs), while block 5 has a higher pulse width (60 μs) and a lower amplitude (3.0 mA). Given this, it may be difficult for the algorithm 250 to determine which of pulses of blocks 2 or 5 will require the highest compliance voltage: block 2's higher amplitude will cause a larger voltage drop (Vrt) across the tissue resistance Rt (see FIG. 8A), while block 5's higher pulse width could cause larger voltage drops (VC1, VC2) across the blocking capacitors. Because it may be difficult in this instance for the algorithm 250 to know a priori which of these conditions will require the highest compliance voltage, the algorithm 250 can set in the IPG's programming instructions compliance voltage monitoring instructions (e.g., CBM) in both of blocks 2 and 5, as shown in FIG. 23B. During operation when the IPG 10 measures the compliance voltage, it will eventually become clear which of the blocks will require the highest compliance voltage, with the measurements taken during that block governing the value to which VH_G1 is set. For example, assume that the ideal compliance voltage is 8.0 for the pulses during block 2 and 9.0V for the pulses during block 5. In this case, the compliance voltage measurements made during the block 5 pulses will dictate the value to which VH_G1 is ultimately set (which in this example would be 9.0V or higher).

Figure 23C:
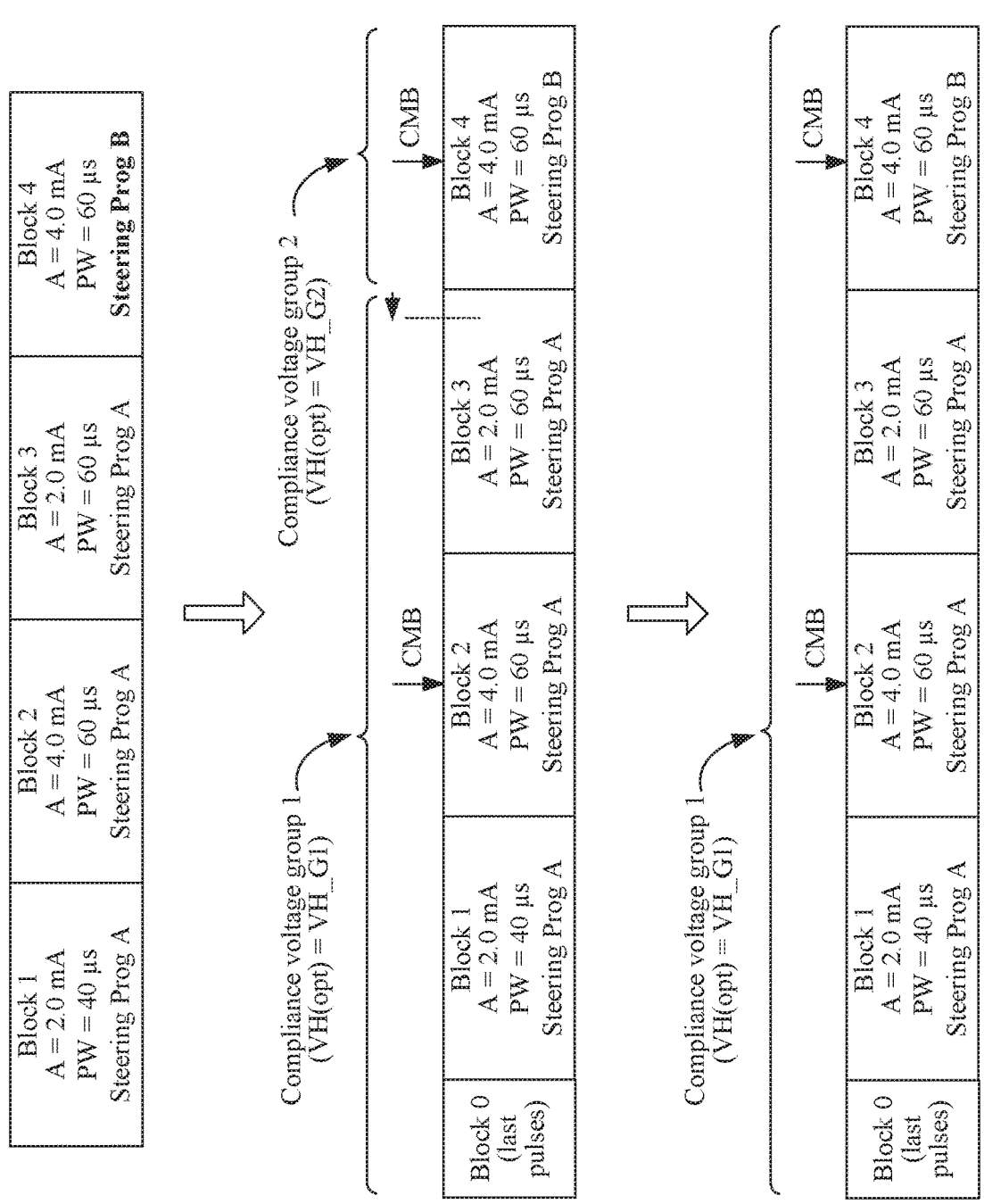

FIG. 23C shows another example by which the algorithm 250 can assess the stimulation parameters of the prescribed waveform and divide the pulses into compliance voltage groups, and set compliance voltage measurement instructions. In this example, the blocks have different steering programs, and hence the pulses are provided to different electrodes. For example, blocks 1, 2, and 3 are governed by steering program A, which may for example prescribe issuing pulses to electrode E1 as an anode and E2 as a cathode. Block 4 is governed by steering program B, which may for example prescribe issuing pulses to electrode E2 as an anode and E4 as a cathode. Note that issuing pulses to different electrodes involves different tissue resistances between those electrodes, which will affect the compliance voltage required to form the pulses. In this regard, the algorithm 250 may decide to place contiguous groups of pulses with the same steering program (i.e., involving the same electrodes) into their own compliance voltage groups. Thus, as shown in the middle of FIG. 23C, a first compliance voltage group 1 is formed including contiguous blocks 1, 2, and 3 governed by steering program A and optimal compliance voltage variable VH_G1. A second compliance voltage group 2 is formed including block 4 governed by steering program B and optimal compliance voltage variable VH_G2. Within compliance voltage group 1, the algorithm 250 determines the worst case block (block 2 with the highest amplitude for the highest pulse width), and sets CBM during one or more pulses in this block to measure the compliance voltage and thus set and adjust VH_G1 for this group. As compliance voltage group 2 contains only a single block 4, CBM is also set during this block to govern VH_G2 for this group.

Note as explained earlier that algorithm 250 may actually include pulses from other blocks within the compliance voltage groups. For example, some last pulses in block 0 may be included in compliance voltage group 1 to allow time to set the VH generator 76 to VH_G1 in advance to ensure that VH_G1 is at the proper value once the pulses in block 1 are formed (see, e.g., FIG. 17D). Compliance voltage group 2 can include some last pulses in block 3 for the same reason. Further, although two different compliance voltage groups have been defined by the algorithm 250 at least initially, remember that the algorithm 250 may eventually consolidate different groups together. See, e.g., FIGS. 15C and 16B. It is therefore possible that compliance voltage group 2, depending on the algorithm 250's programming, could be consolidated into group 1 despite the difference in steering programs used within this consolidated group. For example, if block 4 is of short duration, and/or contains pulses of significantly low energies, such consolidation could be logical despite the difference in steering programs used. Furthermore, the user may simply decide unilaterally use GUI 170 to consolidate certain pulses into a common compliance voltage group (see, e.g., FIG. 13C) despite the difference in steering programs.

The algorithm 250 need not necessarily (initially or otherwise) define compliance voltage groups to include pulses having the same steering program. For example, and as shown in the bottom of FIG. 23C, algorithm 250 has decided to place all of blocks 1-4 into a single compliance voltage group to be governed by VH_G1, despite the different steering programs used. When providing compliance voltage monitoring instructions, the algorithm will preferably identify the highest energy pulses associated with each steering program—i.e., block 2 for steering program A, and block 4 for steering program B. Note in this example that the pulses in these blocks have the same stimulation parameters with the exception of the active electrodes—i.e., both blocks have pulses with amplitudes of 4.0 mA and pulse widths of 60 µs. However, because the different steering programs will involve different tissue resistances, potentially requiring different compliance voltages, the algorithm 250 may not know which of blocks 2 and 4 compromise a worst case from a compliance voltage perspective. Therefore, CBM is set in both of blocks 2 and 4, with the measurements from either dictating VH_G1 for the group.

Figure 23D:
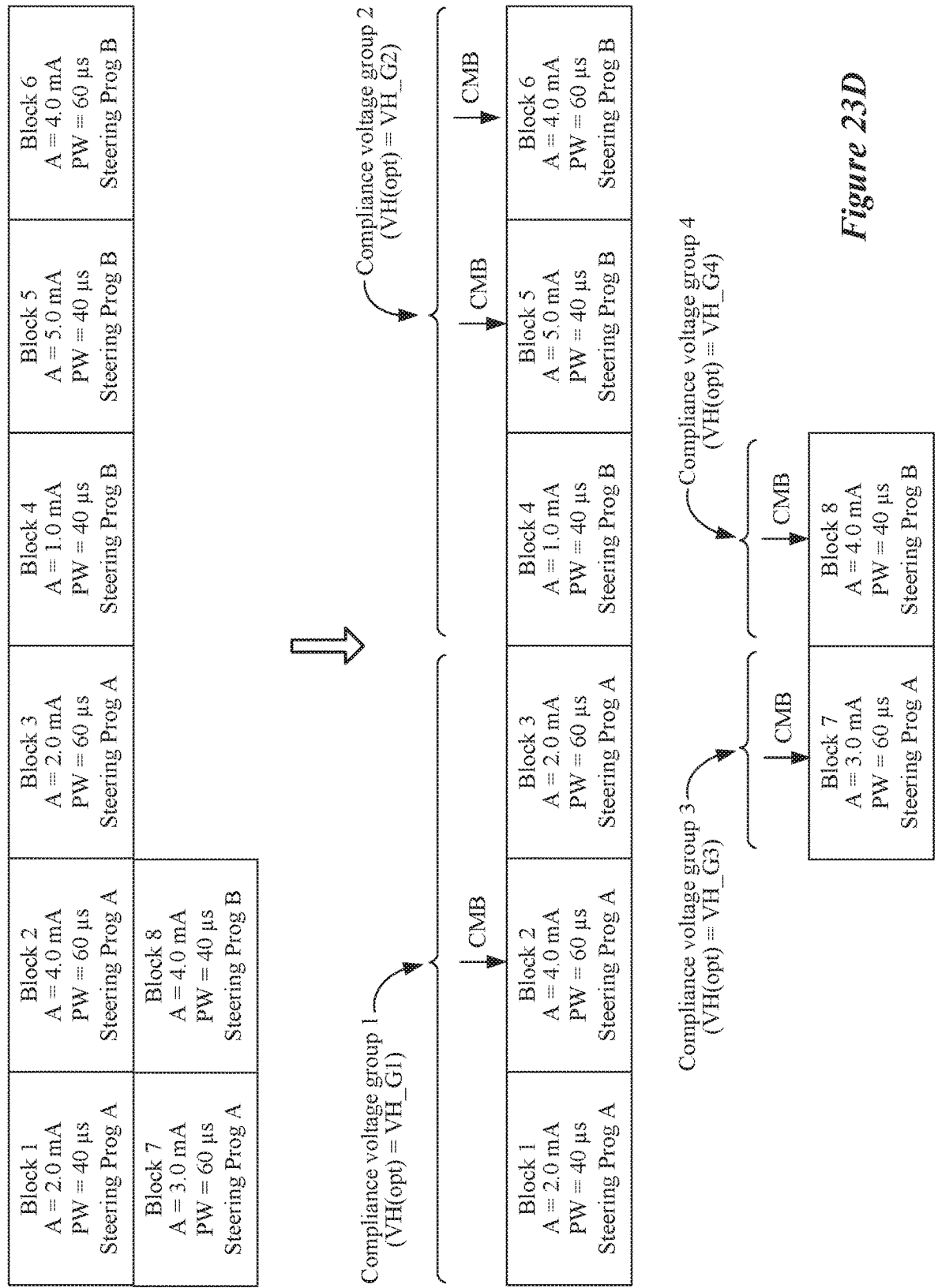
Figure 23E:
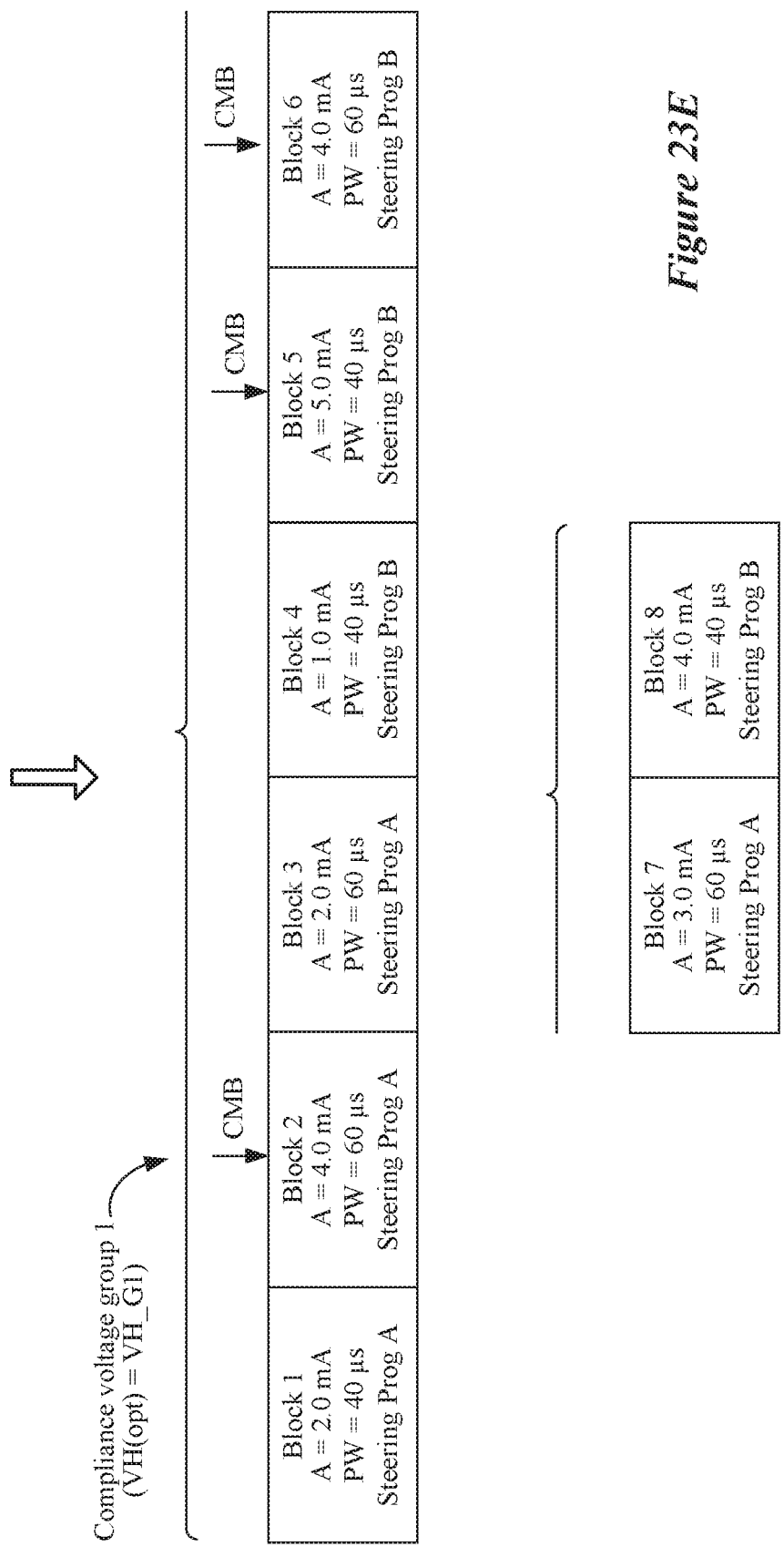

FIGS. 23D and 23E show a more complicated example with different blocks having different amplitudes, pulse widths, and steering programs. In FIG. 23D, contiguous blocks are grouped first in accordance with their steering programs, resulting in four compliance voltage groups: 1 (blocks 1-3) governed by steering program A and VH_G1; 2 (blocks (4-6) governed by steering program B and VH_G2; 3 (block 7) governed by steering program A and VH_G3; and 4 (block 8) governed by steering program B and VH_G4. Within each group, one or more worst case (highest energy) blocks are identified, with CBM set during those blocks to allow VH_Gx to be set for the group. Notice in group 2 that compliance voltage measurements are made during both of blocks 5 and 6. This is because the algorithm 250 may not necessary know as between these two blocks (one having a higher amplitude, the other a higher pulse width) which presents a worst case from a compliance voltage standpoint. Therefore, measurements taken during either of these blocks can be used to dictate VH_G2 for group 2.

FIG. 23E shows the same blocks as used FIG. 23D, but in this case the algorithm 250 (or the user) has decided to place all of blocks 1-8 into a single compliance voltage group govern by VH_G1. As in the other examples, the algorithm 250 preferably automatically identifies one or more worst case blocks whose measurements will be used to govern setting of VH_G1 for the group. In this example, blocks having the same steering program are identified, such as blocks 4, 5, 6, and 8 (steering program B), and blocks 1, 2, 3, 4, and 7 (steering program A). One or more worst-case blocks are identified that are associated with each of these steering programs, and CMB is set during these blocks. For example, block 2 has the highest pulse width and amplitude of the blocks associated with steering program A, and thus CBM is set for this block. As regards the blocks associated with steering program B, blocks 4, 5, and 8 all have a pulse width of 40 µs, with block 5 having the highest amplitude. Block 6 has the highest pulse width (60 µs), but a smaller amplitude than block 5. Therefore, CBM is set during both of blocks 5 and 6, because, as discussed earlier, the algorithm 250 may not necessary know as between these two blocks which presents a worst case from a compliance voltage standpoint. Measurements taken during any of blocks 2, 5, or 6 can be used to dictate VH_G1 for the group.

While the disclosure to this point has focused on use of the invention in conjunction with an IPG 10, the invention may also be used in conjunction with pulse generator devices that are not fully implantable. For example, the invention can also be used in conjunction with an External Trial Stimulator (ETS), which generally mimics operation of a fully implantable pulse generator in a trial setting. See, e.g., U.S. Pat. No. 9,259,574 (describing an ETS). An ETS generally include the same circuitry as in the IPG 10, including DAC and VH generation circuitry, and so the invention can also be used to manage VH in these devices.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for programming a stimulator device, the stimulator device comprising a plurality of electrodes and current generation circuitry configured to provide pulses at selected ones of the electrodes, wherein the current generation circuitry is powered by a time-varying compliance voltage produced at an output of a compliance voltage generator, the method comprising:
   receiving information defining a waveform comprising a sequence of pulses at the selected ones of the electrodes;
   determining a plurality of groups, wherein each group comprises a plurality of contiguous pulses in the waveform;

prior to producing the waveform at the selected ones of the electrodes, associating each group with a compliance voltage variable; and determining programming instructions configured to:
- program the current generation circuitry to produce the groups thereby producing the waveform at the selected ones of the electrodes, and
- program the compliance voltage generator to produce the time-varying compliance voltage at the output, wherein the compliance voltage generator is programmed with the compliance voltage variable associated with the group being produced by the current generation circuitry.

2. The method of claim 1, further comprising determining a compliance voltage value for each compliance voltage variable, wherein each compliance voltage value is determined to be suitable to produce the pulses in their associated group at prescribed amplitudes.

3. The method of claim 2, wherein the compliance voltage values are determined by taking measurements in the stimulator device.

4. The method of claim 1, wherein the method further comprises use of an external device in communication with the stimulator device,
- wherein the information defining the waveform is received at the external device,
- wherein each group is associated with a compliance voltage variable at the external device, and
- wherein the programming instructions are determined at the external device; and
- further comprising transmitting the programming instructions from the external device to the stimulator device.

5. The method of claim 4, further comprising
- determining a compliance voltage value for each compliance voltage variable at the stimulator device, and
- transmitting the determined compliance voltages values to the external device, wherein the programming instructions are configured to program the compliance voltage generator with the compliance voltage values to produce the time-varying compliance voltage at the output,
- wherein the compliance voltage generator is programmed with the compliance voltage value associated with the group being produced by the current generation circuitry.

6. The method of claim 5, wherein the compliance voltage values are determined by taking measurements in the stimulator device.

7. The method of claim 4, wherein the programming instructions are further configured to cause the stimulator device to determine a compliance voltage value for each compliance voltage variable by taking measurements in the stimulator device.

8. The method of claim 1,
- wherein the information defining the waveform is received at the stimulator device;
- wherein each group is associated with a compliance voltage variable at the stimulator device, and
- wherein the programming instructions are determined at the stimulator device.

9. The method of claim 8, further comprising determining a compliance voltage value for each compliance voltage variable at the stimulator device, wherein the compliance voltage values are determined by taking measurements in the stimulator device.

10. The method of claim 1, wherein the plurality of groups are automatically determined using a computer-implementable algorithm, wherein the computer-implementable algorithm is configured to automatically determine the plurality of contiguous pulses in each group by applying one or more rules that identify that at least some of the plurality of contiguous pulses have similar compliance voltage requirements.

11. The method of claim 10, wherein the one or more rules identify that the plurality of contiguous pulses have amplitudes or energies that are within a specified range.

12. The method of claim 1, wherein the method further comprises use of an external device in communication with the stimulator device, wherein at least one of the plurality of groups is determined at least in part based on input received from a user at the external device.

13. The method of claim 1, wherein a first of the groups is produced during a time period comprising a first time period followed by a second time period, wherein the compliance voltage generator is programmed with a first of the compliance voltage variables during the first group.

14. The method of claim 13, wherein the first compliance voltage variable is higher than a preceding compliance voltage variable, wherein the time-varying compliance voltage rises over the first time period, and wherein the time-varying compliance voltage equals the first compliance voltage variable during the second time period.

15. The method of claim 13, wherein the first compliance voltage variable is lower than a preceding compliance voltage variable, wherein the time-varying compliance voltage falls over the first time period, and wherein the time-varying compliance voltage equals the first determined compliance voltage during the second time period.

16. The method of claim 1, wherein the time-varying compliance voltage rises or falls over time periods when the compliance voltage variables to which the compliance voltage generator is programmed change.

17. The method of claim 1, wherein the compliance voltage variables are determined such that the time-varying compliance voltage is always high enough to form the sequence of pulses in the waveform at prescribed amplitudes.

18. The method of claim 1, wherein the information defining the waveform comprises a plurality of blocks of the pulses in the sequence, wherein each of the blocks comprise pulses of the same amplitude, pulse width, energy, or shape.

19. The method of claim 1, wherein the programming instructions are further configured to program the stimulator device to make measurements to assess the time-varying compliance voltage at different points in time, wherein the stimulator device is configured to adjust values of the compliance voltage variables using the measurements.

20. The method of claim 19, wherein if the measurements indicate during production of a particular group that the time-varying compliance voltage is too low, the stimulator device is configured to adjust the compliance voltage variable associated with that group to a higher value, and wherein if the measurements indicate during production of a particular group that the time-varying compliance voltage is too high, the stimulator device is configured to adjust the compliance voltage variable associated with that group to a lower value.

* * * * *